US006348574B1

(12) United States Patent
Godiska et al.

(10) Patent No.: US 6,348,574 B1
(45) Date of Patent: *Feb. 19, 2002

(54) SEVEN TRANSMEMBRANE RECEPTORS

(75) Inventors: Ronald Godiska, Bothell; Patrick W. Gray; Vicki Louise Schweickart, both of Seattle, all of WA (US)

(73) Assignee: ICOS Corporation, Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/088,337

(22) Filed: Jun. 1, 1998

Related U.S. Application Data

(60) Division of application No. 08/245,242, filed on May 17, 1994, now abandoned, and a continuation of application No. 08/153,848, filed on Nov. 17, 1993, now Pat. No. 5,759,804, which is a continuation-in-part of application No. 07/977,452, filed on Nov. 17, 1992, now abandoned.

(51) Int. Cl.$^7$ ........................ C07K 14/72; C07K 14/705
(52) U.S. Cl. .................. 530/350; 530/388.22; 536/23.5
(58) Field of Search ............................ 435/6; 536/23.5; 530/350, 388.22, 387.9

(56) References Cited

FOREIGN PATENT DOCUMENTS

| WO | WO 92/17497 | 10/1992 |
|---|---|---|
| WO | WO 92/18641 | 10/1992 |
| WO | WO 94/12635 | 6/1994 |

OTHER PUBLICATIONS

Allen et al., "G–Protein–Coupled Receptor Genes as Protooncogenes: Constitutively Activating Mutation of the $\alpha_{1B}$–Adrenergic Receptor Enhances Mitogenesis and Tumorigenicity," *Proc. Natl. Acad. Sci., USA*, 88:11354–11358 (1991).
Alper, "Oligonucleotides Surge into Clinical Trials," *Bio/Technology*, 11:1225 (1993).
Arai et al., "Cloning and Expression of a cDNA Encoding an Endothelin Receptor," *Nature*, 348:730–732 (1991).
Benoist et al., "The Ovalbumin Gene—Sequence of Putative Control Regions," *Nucleic Acids Research*, 8:127–142 (1980).
Birkenbach et al., "Epstein–Barr Virus–Induced Genes: First Lymphocyte–Specific G Protein–Coupled Peptide Receptors," *Journal of Virology*, 67(4):2209–2220 (1993).
Blin et al., "A General Method for Isolation of High Molecular Weight DNA from Eukaryotes," *Nucleic Acids Research*, 3(9):2303–2308 (1976).
Boulay, "Synthesis and Use of a Novel N–Formyl Peptide Derivative to Isolate a Human N–Formyl Peptide Receptor cDNA," *Biochem. Biophys. Res. Commun.*, 168:1103–1109 (1990).
Burbach et al., "The Structure of Neuropeptide Receptors," *European Journal of Pharmacology*, 227:1–18 (1992).
Cherif et al., "Detection of Single–Copy Genes by Nonisotopic in Situ Hybridization of Human Chromosomes," *Hum. Genet.*, 81:358–362 (1989).
Chirgwin et al., "Isolation of Biologically Active Ribonucleic Acid from Sources Enriched in Ribonuclease," *Biochemistry*, 18(24):5294–5299 (1979).
Chomczynski, "Single–Step Method of RNA Isolation by Acid Guanidinium Thiocyanate–Phenol–Chloroform Extraction," *Analytical Biochemistry*, 162:156–159 (1987).
Cotecchia et al., "Regions of the $\alpha_1$–Adrenergic Receptor Involved in Coupling to Phosphatidylinositol Hydrolysis and Enhanced Sensitivity of Biological Function," *Proc. Natl. Acad. Sci., USA*, 87:2896–2900 (1990).
Crooke et al., "Therapeutic Applications of Oligonucleotides," *Bio/Technology*, 10:882–886 (1992).
Dohlman et al., "Model Systems for the Study of Seven–Transmembrane Segment Receptors," *Ann. Rev. Biochem.*, 60:653–688 (1991).
Downes et al., "The Polyphosphoinositide Phosphodiesterase of Erythrocyte Membranes," *Biochem. J.*, 198:133–140 (1981).
EMBL 44 Data Bank Accession No. M99293, Aug. 19, 1992 (rel. 33, created) Federsppiel et al.
EMBL 44 Data Bank Accession No. L01639, Sep. 14, 1992 (rel. 33, created), Janzin et al.
EMBL 44 Data Bank Accession No. D10924, Jul. 16, 1992 (rel. 32, created), Nomura et al.
Fan et al., "Mapping Small DNA Sequences by Fluorescence in situ Hybridization Directly on Banded Metaphase Chromosomes," *Proc. Natl. Acad. Sci., USA*, 87:6223–6227 (1990).
Federsppiel et al., "Molecular Cloning of the cDNA and Chromosomal Localization of the Gene for a Putative Seven–Transmembrane Segment (7–TMS) Receptor Isolated from Human Spleen," *Genomics*, 16:707–712 (1993).
Findeis et al., "Targeted Delivery of DNA for Gene Therapy via Receptors," *TIBTECH*, 11:202–205 (1993).
Gerard, "The Chemotactic Receptor for Human C5a Anaphylatoxin," *Nature*, 349:614–617 (1991).
Hall et al., "Linkage of Early–Onset Familial Breast Cancer to Chromosome 17q21," *Science*, 250:1684–1689 (1990).
Higuchi, R., "Using PCR to Engineer DNA," in *PCR Technology*, Chapter 6, Erlich, Ed., Stockton Press, New York, pp. 61–70 (1989).
Hirata et al., "Cloning and Expression of cDNA for a Human Thromboxane A$_2$ Receptor," *Nature*, 349:617–620 (1991).

(List continued on next page.)

*Primary Examiner*—Scott W. Houtteman
(74) *Attorney, Agent, or Firm*—Marshall, O'Toole, Gerstein, Murray & Borun

(57) ABSTRACT

DNA sequences encoding seven novel seven transmembrane receptors and variants thereof are disclosed as well as materials and methods for production of the same by recombinant techniques. Antibody substances specific for each of the seven transmembrane receptors are disclosed as useful for the modulation of the ligand/receptor binding reactions of the receptors.

17 Claims, 2 Drawing Sheets

OTHER PUBLICATIONS

Holmes et al., "Structure and Functional Expression of a Human Interleukin–8 Receptor," *Science*, 253:1278–1280 (1991).

Honda et al., "Cloning by Functional Expression of Platelet–activating Factor Receptor from Guinea–pig Lung," *Nature*, 349:342–346 (1991).

Jazin et al., "A proposed bovine neuropeptide Y (NPY) receptor cDNA clone, or its human homologue, confers neither NPY binding sites not NPY responsiveness on transfected cells," *Regulatory Peptides*, 47:247–258 (1993).

Julius et al., "Ectopic Expression of the Serotonin 1c Receptor and the Triggering of Malignant Transformation," *Science*, 244:1057–1062 (1989).

Khorana, "Rhodospin, Photoreceptor of the Rod Cell," *J. Biol. Chem.*, 267:1–4 (1992).

Kozak, "Compilation and Analysis of Sequences Upstream from the Translational Start Site in Eukaryotic mRNAs," *Nucleic Acids Research*, 12(2):857–872 (1984).

Lefkowitz, "Turned on to I11 Effect," *Nature*, 365:603–604 (1993).

Libert, "Selective Amplification and Cloning of Four New Members of the G Protein–Coupled Receptor Family," *Science*, 244:569–572 (1989).

Linder et al., "G Proteins: Tucked into the Internal Surface of the Cell's Outer Membrane, These Versatile Molecules Coordinate Cellular Responses to a Multitude of Signals that Impinge from Without," *Scientific American*, 267:56–65 (1992).

Mitani et al., "Delivering Therapeutic Genes—Matching Approach and Application," *TIBTECH*, 11:162–166 (1993).

Murphy et al., "Cloning of Complementary DNA Encoding a Functional Human Interleukin–8 Receptor," *Science*, 253:1280–1283 (1991).

Murphy et al., "Isolation of a cDNA encoding the vascular type–1 angiotensin II receptor," *Nature*, 351:233–236 (May, 1991).

Naylor et al., "Human Immune Interferon Gene is Located on Chromosome 12," *J. Exp. Med.*, 57:1020–1027 (1983).

Neote et al., "Molecular Cloning , Functional Expression, and Signaling Characteristics of a C–C Chemokine Receptor," *Cell*, 72:415–425 (1993).

Nomura et al., "Molecular cloning of cDNAs encoding a LD78 receptor and putative leukocyte chemotactic peptide receptors," *International Immunology*, 5(10):12389–1249 (1993).

Nomura et al., "Molecular Cloning of Complementary DNAs for Putative Chemotactic Polypeptide Receptor Family," *8th International Congress of Immunology*, Budapest, Hungary (Aug. 23–28, 1992).

O'Brien, Ed., in *Genetic Maps: Locus Maps of Complex Genomes*, Sixth Edition, Book 5, Human Maps, Cold Spring Harbor Laboratory Press, Plainview, New York, pp. 5.108–5.109 (1993).

Parma et al., "Somatic Mutations in the Thyrotropin Receptor Gene Cause Hyperfunctioning Thyroid Adenomas," *Nature*, 365:649–651 (1993).

Probst et al., "Sequence Alignment of the G–Protein Coupled Receptor Superfamily," *DNA and Cell Biology*, 11(1):1–20 (1992).

Raport et al., "The orphan G–protein–coupled receptor–encoding gene V28 is closely related to genes for chemokine receptors and is expressed in lymphoid and neural tissues," *Gene*, 163:295–299 (1995).

Robinson et al., "Constitutively Active Mutants of Rhodopsin," *Neuron*, 9:719–725 (Oct., 1992).

Rosenthal et al., "Nephrogenic Diabetes Insipidus: A V2 Vasopressin Receptor Unable to Stimulate Adenylyl Cyclase," *J. Biol. Chem.*, 268:13030–13033 (1993).

Ruat et al., "Molecular Cloning, Characterization, and Localization of a High–Affinity Serotonin Receptor (5–HT$_7$) Activating cAMP Formation," *Proc. Natl. Acad. Sci., USA*, 90:8547–8551 (1993).

Sasaki et al., "Cloning and Expression of a Complementary DNA Encoding a Bovine Adrenal Angiotensin II Type–1 Receptor," *Nature*, 351:230–233 (1991).

Shenker et al., "A Constitutively Activating Mutation of the Lutenizing Hormone Receptor in Familial Male Precocious Puberty," *Nature*, 365:652–654 (1993).

Sikora, "Gene Therapy for Cancer," *TIBTECH*, 11:197–201 (1993).

Smith et al., "Single–step Purification of Polypeptides Expressed in *Escherichia coli* as Fusions with Glutathione S–transferase," *Gene*, 67:31–40 (1988).

Stryer, "Visual Excitation and Recovery," *J. Biol. Chem.*, 266(17):10711–10714 (1991).

Thomas et al., "Molecular Cloning of the fMet–Leu–Phe Receptor from Neutorphils," *J. Biol. Chem.*, 265(33):20061–20064 (1990).

Vu et al., "Molecular Cloning of a Functional Thrombin Receptor Reveals a Novel Proteolytic Mechanism of Receptor Activation," *Cell*, 64:1057–1068 (1991).

Wada et al., "Codon usage tabulated from the GenBank genetic sequence data," *Nucl. Acids Res.*, 19S:1981–1986 (1991).

Yamada et al., "Cloning and Functional Characterization of a Family of Human and Mouse Somatostatin Receptors Expressed in Brain, Gastrointestinal Tract, and Kidney," *Proc. Natl. Acad. Sci., USA*, 89:251–255 (1992).

"HUGO Statement on Patenting of DNA Sequences," Human Genome Organisation, Genome Digest, p. 6 (Apr., 1995).

SEVEN TRANSMEMBRANE RECEPTORS

This application is a divisional of U.S. patent application Ser. No. 08/245,242 filed on May 17, 1994, now abandoned, and is a continuation-in-part of U.S. patent application Ser. No. 08/153,848 filed on Nov. 17, 1993 now U.S. Pat. No. 5,759,804 which is in turn a continuation-in-part of U.S. patent application Ser. No. 07/977,452 filed on Nov. 17, 1992 now abandoned.

FIELD OF THE INVENTION

The present invention relates generally to a family of cellular receptors involved in signal transduction, the seven transmembrane receptors, and more particularly to the cloning and expression of DNA sequences encoding seven novel seven transmembrane receptors.

BACKGROUND

The seven transmembrane receptors (also known as heptahelical, serpentine, or G protein-coupled receptors) comprise a superfamily of structurally related molecules. Possible relationships among seven transmembrane receptors (7TM receptors) for which amino acid sequence had previously been reported are reviewed in Probst et al., *DNA and Cell Biology*, 11(1): 1–20 (1992). Briefly, the 7TM receptors exhibit detectable amino acid sequence similarity and all appear to share a number of structural characteristics including: an extracellular amino terminus; seven predominantly hydrophobic α-helical domains (of about 20–30 amino acids) which are believed to span the cell membrane and are referred to as transmembrane domains 1–7; approximately twenty well-conserved amino acids; and a cytoplasmic carboxy terminus. The amino acid similarity among different 7TM receptors ranges from 10% to more than 80% and receptors which recognize similar or identical ligands generally exhibit high levels of homology. The 7TM receptors can be grouped based on their homology levels and/or the ligands they recognize. For example, the interleukin-8 receptor, the angiotensin II receptor, the thrombin receptor, the endothelin receptors, the N-formyl peptide receptor and the C5a receptor all bind peptide ligands and share 20–30% amino acid similarity.

7TM receptors recognize a great diversity of ligands (for example, light, odorants, neurotransmitters, peptide hormones and small molecules) and transduce their signals via heterotrimeric guanine nucleotide-binding proteins (G-proteins) effecting a broad array of biological activities (including visual excitation, olfactory reception, and neurotransmission) through various intracellular enzymes, ion channels and transporters. Signal transduction pathways have been elucidated for rhodopsin [Khorana, *J. Biol. Chem.*, 267: 1–4 (1992) and Stryer, *J. Biol. Chem.*, 266: 10711–10714 (1991)] and the beta-adrenergic receptors [Dohlman et al., *Ann. Rev. Biochem.*, 60: 653–688 (1991)] and are thought to illustrate the pathways utilized by other 7TM receptors. Each 7TM receptor is predicted to associate with a particular G protein at the intracellular surface of the plasma membrane. The binding of the receptor to its ligand is thought to result in activation (i.e., the exchange of (GTP for GDP on the α-subunit) of the G protein which in turn stimulates specific intracellular signal-transducing enzymes and channels. Thus, the function of each 7TM receptor is to discrimnate its specific ligand from the complex extracellular milieu and then to activate G proteins to produce a specific intracellular signal. Cotecchia et al., *Proc. Natl. Acad. Sci, USA*, 87: 2896–2900 (1990) reports that the intracellular loop of the third transmembrane domain of the 7TM receptors comprises important determinants for receptor coupling to specific G proteins, however, Lefkowitz, *Nature*, 265: 603–604 (1993) summarizes reports that other regions of 7TM receptors may also be essential in maintaining 7TM receptors in a constrained, inactive conformation until ligand binding occurs.

Recently, several 7TM receptors have been identified which recognize ligands important for immunological and hemostatic activities. Holmes et al., *Science*, 253: 1278–1280 (1991) describes the interleukin 8 receptor (IL8R1) as involved in neutrophil chemotaxis and Sasaki et al., *Nature*, 351: 230–233 (1991) reports the angiotensin II receptor (AT2R) is involved in vascular hemostasis. Similarly, the endothelin receptors [Arai et al., *Nature*, 348: 730–732 (1990)] regulate vasoconstriction and smooth muscle tone. The C5a receptor mediates chemotaxis, granule enzyme release and superoxide generation in vitro and appears to be involved in anaphylaxis and septic shock in vivo [Gerard and Gerard, *Nature*, 349: 614–617 (1991)]. Thrombin is also recognized by a 7TM receptor and is a potent activator of platelet aggregation, monocyte chemotaxis, lymphocyte mitogenesis and mediates inflammatory responses to vascular injury. The N-formyl peptide (f-met-leu-phe) receptor is responsible for neutrophil chemotaxis and activation [Thomas et al., *J. Biol. Chem.*, 265: 20061 (1990)]. While these 7TM receptors all have peptide ligands, other 7TM receptors that recognize small organic compounds also mediate proinflammatory activities. For example, the Platelet Activating Factor receptor recognizes a bioactive phospholipid [Honda et al., *Nature*, 349: 342–346 (1991)] which causes platelet aggregation and endotoxic shock. The thromboxane $A_2$ receptor recognizes an arachidonate metabolite which also stimulates vasoconstriction and platelet aggregation and is implicated in stroke and bronchial asthma [Hirata et al., *Nature*, 349: 617–620 (1991)].

Mutations in the third intracellular loop of one 7TM receptor (the thyrotrin receptor) and in the adjacent sixth transmembrane domain of another 7TM receptor (the luteinizing hormone receptor) have been reported to be the genetic defects responsible for an uncommon form of hyperthyroidism [Parma et al., *Nature*, 365: 649–451 (1993)] and for familial precocious puberty [Shenker et al., *Nature*, 365: 652–654 (1993)], respectively. In both cases the mutations result in constitutive activation of the 7TM receptors. Previously, other studies have shown that mutations that prevent the activation of 7TM receptors are responsible for states of hormone resistance which are responsible for diseases such as congenital nephrogenic diabetes insipidus. See Rosenthal et al., *J. Biol. Chem.*, 268: 13030–13033 (1993). Still other studies have shown that several 7TM receptors can function as protooncogenes and be activated by mutational alteration. See, for example, Allen et al., *Proc. Natl. Acad. Sci. USA*, 88: 11354–11358 (1991) which suggests that spontaneously occuring mutations in some 7TM receptors may alter the normal function of the receptors and result in uncontrolled cell growth associated with human disease states such as neoplasia and atherosclerosis. Therefore, mutations in 7TM receptors may underlie a number of human pathologies.

Because a variety of therapeutic uses may be projected for 7TM receptors involved in immunological processes in both health and disease states and because it is generally believed that numerous proteins are involved in immunological processes, there continues to exist a need in the art for the identification of additional 7TM receptors that participate in such processes and especially a need for information specifically identifying and characterizing such proteins in terms of their amino acid sequence. Isolation of DNA encoding a novel 7TM receptor also provides the basis for determination of the role of receptor in health and disease states. To the extent that such receptors might form the basis for the development of therapeutic and/or diagnostic agents, it is essential that the DNA encoding them be isolated. The isolated DNA would, for example, provide for the large scale production of the 7TM proteins, allow for the identification of cells naturally producing them, and permit the preparation/identification of antibody substances and/or other novel binding substances (including natural ligands, agonists and antagonists) which are specifically reactive with a particular 7TM receptor (or group of receptors) and which have the capacity to modulate the biological activities of the receptor(s).

SUMMARY OF THE INVENTION

The present invention provides purified and isolated polynucleotides (i.e., DNA sequences and RNA transcripts thereof) encoding seven novel 7TM rectors designated V28, V31, V112, R20, R2, R12, and RM3 as well as polypeptide variants (including fragments and analogs) thereof which possess at least one ligand/receptor binding activity or immunological property specific to one of the seven 7TM receptors. Fragments of a 7TM receptor of the invention which correspond to the N-terminal extracellular domain; the transmembrane domains; the individual extracellular and intracellular loops connecting the transmembrane domains; the C-terminal cytoplasmic domain and fusions thereof are specifically contemplated. Preferred DNA sequences of the invention include genomic and cDNA sequences as well as wholly or partially chemically synthesized DNA sequences.

Specifically illustrating polynucleotide sequences of the present invention are the DNA inserts encoding the V28, V31, V112, R2, R12 and R20 7TM receptors in plasmids which were deposited with the American Type Culture Collection (ATCC), 12301 Parklawn Drive, Rockville, Md. 20852, on Oct. 12, 1992 and were respectively assigned ATCC Accession Nos. 75330, 75327, 75326, 75329, 75331 and 75328. Also illustrating polynucleotide sequences of the invention is the DNA insert encoding the RM3 7TM receptor in a plasmid which was deposited with the ATCC on Nov. 2, 1992 and was assigned ATCC Accession No. 75340.

According to another aspect of the invention, biologically active plasmid and viral DNA vectors incorporatng DNA sequences of the invention are provided as well as vectors wherein the DNA encoding a 7TM receptor or 7TM receptor variant is operatively linked to an endogenous or heterologous expression control sequence. Also provided by the invention are procaryotic or eucaryotic host cells stably transformed or transfected with a DNA sequence of the invention so that the 7TM receptor polypeptide or variant polypeptide encoded by the DNA sequence is expressed in the host cell. Host cells expressing such 7TM products can serve a variety of purposes. To the extent that the expressed products are "displayed" on host cell surfaces, the cells may constitute a valuable immunogen for the development of antibody substances specifically immunoreative with 7TM receptors or 7TM recptor variants. Host cells of the invention are conspicuously useful in methods for the large scale production of 7TM receptors when the cells are grown in a suitable culture medium and the 7TM receptor polypeptide products are isolated from the cells or from the medium in which the cells are grown. Host cells expressing the novel 7TM receptors are also useful in assays for identifying antagonists or agonists of 7TM receptor binding.

Novel 7TM receptors of the invention may be obtained as isolates from natural cell sources, but are preferably produced by recombinant procedures involving host cells of the invention. The products may be obtained in fully or partially glycosylated, partially or wholly de-glycosylated, or non-glycosylated forms, depending on the host cell selected for recombinant production and/or post-isolation processing. 7TM receptor variants of the invention may comprise water soluble and insoluble polypeptide or peptide fragments, and may also comprise polypeptide analogs wherein one or more of the naturally specified amino acids is deleted or replaced: (1) without loss, and preferably with enhancement, of one or more biological activities or immunological characteristics specific for the 7TM receptor; or (2) with specific disablement of a particular ligand/receptor binding function. Analog polypeptides including additional amino acid (e.g., lysine) residues that facilitate multimer formation are contemplated.

Also comprehended by the present invention are antibody substances (e.g., monoclonal and polyclonal antibodies, single chain antibodies, chimeric antibodies, CDR-grafted antibodies and the like) or other binding proteins which are specifically reactive with 7TM receptor or 7TM receptor variants of the invention. Antibody substances can be developed using isolated natural or recombinant 7TM receptor products (including peptides) or cells expressing such products on their surfaces. The antibody substances are useful, in turn, in complexes for immunization to generate anti-idiotypic antibodies as well as for purifying polypeptides of the invention and for identifying cells producing the polypeptides on their surfaces. Assays for the detection and quantification of 7TM receptors on cell surfaces and in fluids such a serum may involve a single antibody substance or multiple antibody substances in a "sandwich" assay format. The antibody substances as well as agonists or antagonists of 7TM receptor binding (e.g., small molecules or peptides) are also manifestly useful in modulating (i.e., blocking, inhibiting or stimulating) ligand/receptor binding reactions of 7TM receptors of the invention, especially those reactions involved in immunological and/or inflammatory events in vivo.

The scientific value of the information contributed through the disclosures of DNA and amino acid sequences of the present invention is manifest. As one series of examples, knowledge of the sequence of a cDNA for a 7TM receptor makes possible the isolation by DNA/DNA hybridization of genomic DNA sequences encoding the 7TM receptor and specifying the 7TM receptor gene expression control regulatory sequences such as promoters, operators and the like. DNA/DNA hybridization procedures carried out with DNA sequences of the invention and under stringent conditions are likewise expected to allow the identification of DNAs encoding allelic variants of a 7TM receptor, mutant forms of a 7TM receptor associated with a particular disease state, other structurally related proteins sharing the biological and/or immunological specificity of the 7TM receptor, and non-human species proteins homologous to the 7TM receptor. DNAs of the invention are useful in DNA/RNA hybridization assays to detect the capacity of cells to synthesize a 7TM receptor.

Also made available by the provision of DNA sequences of the invention are therapeutically useful oligonucleotides (e.g., antisense oligonucleotides, oligonucleotides for triplex formation or aptamers) relevant to regulating expression of a 7TM receptor by those cells which ordinarily express the same [as is described for other oligonucleotides in Crooke et al., *BIO/TECHNOLOGY*, 10: 882–886 (1992) and in Alper, BIO/TECHNOLOGY, 11: 1225 (1993)]. DNA sequences of the invention may also be used in vectors which have been developed for gene therapy such as those described in Mitani et al., TIBECH, 11: 162–166 (1993) (delivering therapeutic genes); Sikora, TIBTECH, 11: 197–201 (1993) (gene therapy for cancer); and Findeis et al., TIBTECH, 11: 202–205 (1993) (gene therapy via receptors).

Numerous aspects and advantages of the present invention will be apparent upon consideration of the following drawings and detailed description.

DETAILED DESCRIPTION

Figure 1A:
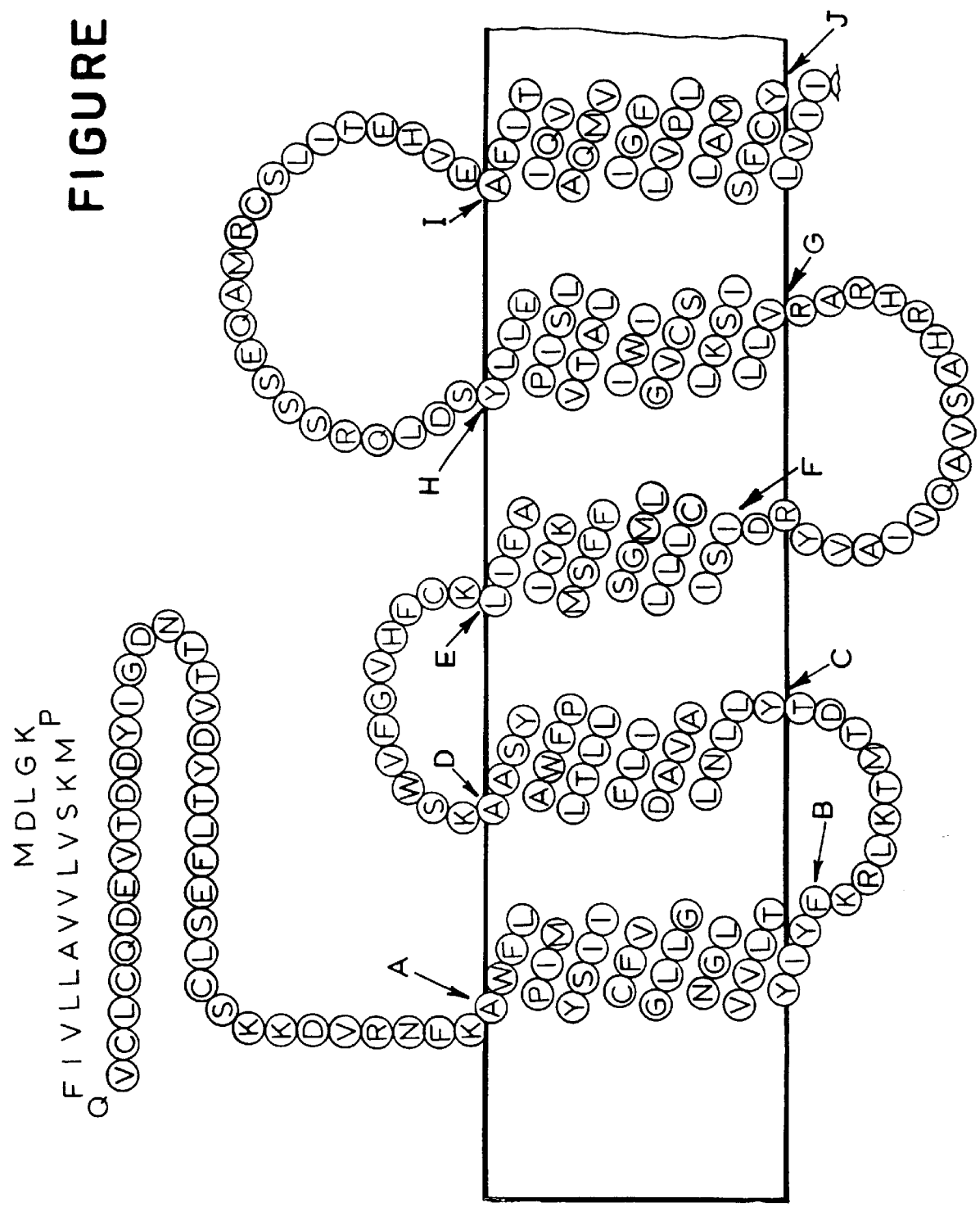
FIGS. 1A and 1B (referred to herein collectively as FIG. 1) are a schematic illustration of a possible conformation of the V31 7TM receptor in a cell membrane wherein transmembrane domain 1 is between points A and B, transmembrane domain 2 is between points C and D, transmembrane domain 3 is between points E and F, transmembrane domain 4 is between points G and H, transmembrane domain 5 is between points I and J, transmembrane domain 6 is between points K and L, and transmembrane domain 7 is between points M and N.

The present invention is illustrated by the following examples relating to the isolation of human genomic and cDNA sequences encoding the novel 7TM receptors herein designated V28, V31, V112, R20, R2, R12 and RM3. More particularly, Example 1 describes the isolation of PCR fragments encoding portions of the R20, V31, V28 and V112 7TM receptors. Example 2 describes the isolation of a full length human V31 genomic clone. Example 3 describes the isolation of a V31 human cDNA clone and further characterization of the V31 genomic clone. Example 4 describes the cloning of a full length murine V31 genomic clone. The cloning of a full length, human genomic clones for V28 is described in Example 5. Example 6 describes the isolation of a full length human V28 cDNA. Example 7 sets out a description of a human V112 cDNA. Example 8 describes the isolation of a full length genomic DNA encoding human R20. Example 9 presents experiments which reveal the chromosomal location of the human V31, V28 and R20 genes. The isolation of full length R2 and R12 7TM receptor genes from a human genomic fetal liver library is detailed in Example 10. Example 11 describes the cloning of a cDNA encoding the RM3 7TM receptor. Example 12 presents a comparison of the amino acid sequences of 7TM receptors of the invention with amino acid sequences of previously described 7TM receptors. The transfection of human cells with genomic and cDNA sequences encoding the 7TM receptor V31 and the phenotype of the transfected cells are detailed in Example 13. Expression of 7TM receptors of invention in various human tissues and hematopoietic cell lines as assayed by Northern blot and in situ hybridization is described in Example 14. Examples 15 and 16 respectively describe the expression of V31 and R20 genomic sequences as fusion proteins with Glutathione-S-Transferase in E. coli, while Example 17 describes the expression of V31 and V28 cDNA sequences as fusion proteins with Glutathione-S-Transferase in E. coli. Example 18 describes the generation of polyclonal sera reactive with the V31 fusion proteins and V31 peptides useful for generating monoclonal and polyclonal antibodies specific for V31. Example 19 presents various methods for identifying extracellular and intracellular ligands of the 7TM receptors of the invention.

EXAMPLE 1

The polymerase chain reaction (PCR) was chosen as a method for identifying new members of the 7TM receptor superfamily.

Design and Synthesis of PCR Primers

Initially, eight different degenerate oligonucleotide primer pools were designed based on the amino acid sequence of the Platelet Activating Factor receptor. PCR with the eight primer pools failed to amplify any new 7TM receptor sequences although several Platelet Activating Factor rector clones were amplified.

A second set of degenerate primers was then designed from regions of amino acid sequence high similarity between IL8R1 and AT2R which have an overall amino acid similarity of 30%. The first region of high similarity occurs in the second transmembrane domain and contains 16 of 20 residues that are identical in both receptors. A 5' degenerate primer pool (where each primer was 45 nucleotides in length plus a cloning site, a longer primer than typically is used for PCR) was synthesized based on this sequence. The sequence of the upstream primer is set out in IUPAC nomenclature below, wherein the underlined nucleotides represent a BamHI site introduced to facilitate cloning.

Primer pool 1 (SEQ ID NO: 1) GAC <u>GGA TCC</u> GTT TTT CTG TTG AAT TTG GCT CTG GCT GAC YTA YKC TTT KYM CTG ACY TTG CCM MTS TGG This oligonucleotide pool was degenerate at ten positions to account for multiple codon choices and the four amino acid differences between IL8R1 and AT2R. Ten positions were not degenerate, but were designed instead with a single 'best guess' nucleotide based on human codon frequency tables in Wada et al., Nucl. Acids Res., 195: 1981–1986 (1991).

A second region of extended identity between IL8R1 and AT2R occurs in the putative second cytoplasmic domain where eight identical adjacent residues are shared. This region was utilized to design a downstream antisense PCR primer pool (21 nucleotides in length plus a restriction site). The sequence of the downstream primer is set out in IUPAC nomenclature below, wherein the underlined nucleotides represent a HindIII site introduced to facilitate cloning.

Primer pool 2 (SEQ ID NO: 2) GGC <u>TAA GCT TGI</u> ACI ATI GC(Y or I) AGR TAI CGR TC This oligonucleotide contained the nucleotide inosine at several of the degenerate positions because of its ability to base pair with multiple nucleotides.

Isolation of Genomic DNA Sequences Encoding Novel 7TM Receptors by PCR

Oligonucleotide primer pools 1 and 2 were used to amplify human genomic DNA purified from leukocytes by the method of Blin and Stafford, Nucl. Acids Res., 3: 2303–2308 (1976). PCR was performed in a Perkin-Elmer-Cetus machine with the following thermocycling parameters: an initial four minutes to bring the reaction to 94° C., followed by 25 cycles of (1) 94° C. denaturation step for 30 seconds, (2) 50° C. annealing step for 45 seconds, and (3) 72° C. extension step for two minutes. The reaction mixture contained 1×PCR buffer, 0.25 mM dGTP, 0.25 mM dATP, 0.25 mM dCTP, 0.25 mM TTP, 0.01 µg/µl primer pool 1, 0.01 µg/µl primer pool 2, 0.125 mg/ml human genomic DNA, and 2.5 units Taq polymerase in a total reaction volume of 40 µl. The predominate PCR product observed was the predicted size of 192 base pairs (bp) as determined by electrophoresis on a 1.2% agarose gel. Eight different PCR reactions were performed with increasing amounts of MgCl$_2$ ranging from 0.5 mM to 2.25 mM. The concentration of MgCl$_2$ did not appear to change the quantity of PCR product so all eight reactions were pooled, extracted with phenol and chloroform, ethanol precipitated, and then digested with restriction endonucleases BamHI and HindIII. The digested DNA was electrophoresed on 1.2% agarose and the 192 bp band was excised and eluted from the gel. The recovered DNA was then ligated into BamHI-HindIII digested plasmid Bluescript SK– (Stratagene Cloning Systems, La Jolla, Calif.) and transformed into bacterial host XL-1Blue. Several thousand clones were obtained and most appeared to be recombinants as determined by blue-white color selection.

Twenty different clones were chosen for DNA sequence analysis. Plasmid DNA was prepared and sequenced by the dideoxy chain termination method. Most of the plasmids contained sequences corresponding to IL8R1 or AT2R, but two of the twenty clones contained a unique sequence which encoded a peptide with 28% similarity to IL8R1 and 46% similarity to AT2R. This novel sequence was termed R20 and encoded a series of amino acids consistent with a 7TM receptor: the first 17 residues were generally hydrophilic and contained a highly conserved cysteine residue and the last 22 residues were hydrophobic, corresponding to the third transmembrane domain.

In order to identify additional novel sequences, the clones obtained by PCR using primer pools 1 and 2 were screened by hybridization to eliminate IL8R1, AT2R and R20 clones. Approximately 1000 clones were individually isolated and grown in microtitre wells. With the aid of a pronging device, the colonies were stamped onto plates, grown overnight, and transferred to nitrocellulose. DNA on the blots was denatured and prepared by standard methods. Hybridization was then performed with $^{32}$P-labelled probes specific for IL8R1, A72R, and R20. Clones which did not hybridize were then chosen for sequence analysis. Three new clones were identified that appeared to encode 7TM receptor segments. The inserts of the clones were designated V31, V28, and V112. The sequence of the insert encoding V112 (ATCC 75326) is set out in SEQ ID NO: 3. Entire genes encoding the putative 7TM receptor genes designated V31, V28 and R20 were isolated from human genomic DNA libraries cloned in lambda phage as described below in Examples 2, 5 and 8, respectively.

EXAMPLE 2

A V31 genomic clone was isolated by PCR using the specific primers set out below.

Primer V31-forward (SEQ ID NO: 4) TGG GCC TAC AGC GCG GCC AA

Primer V31-reverse (SEQ ID NO: 5) TC AAT GCT GAT GCA AAG AAG

A human genomic DNA lambda library (ATCC 37333) was fractionated into 150 pools of approximately 3000 clones each. The 150 pools were divided into 15 groups, each containing ~30,000 phage. PCR with the V31 specific primers was performed with the following parameters: an initial four minutes to bring the reaction to 94° C., followed by 30 cycles of (1) 94° C. denaturation step for 30 seconds, (2) 50° C. annealing step for 45 seconds, and (3) 72° C. extension step for two minutes. The reaction mixture contained 1× PCR buffer, 0.25 mM dGTP, 0.25 mM dATP, 0.25 mM dCTP, 0.25 mM TTP, 0.01 µg/µl V31 forward primer, 0.01 µg/µl V31 reverse primer, 1 µl phage pool lysate, and 2.5 units Taq polymerase in a total reaction volume of 50 µl. One of the 15 groups yielded a PCR fragment of the predicted size of 114 bp, and a single pool of this group also produced the same fragment when subjected to the same PCR conditions. Hybridization was then used to identify the V31 coding phage. Approximately 6000 phage were plated on five 15 cm plates. Duplicate filters were absorbed to each plate and processed for hybridization by standard methods. A $^{32}$P labeled probe was prepared from the V31 segment plasmid by incorporating $^{32}$P-dCTP into a PCR reaction with the V31 specific primers. Hybridization with this radiolabled probe and washing of filters was performed under conditions of reduced stringency. The hybridization solution was 20% formamide, 5×SSC (0.75 M sodium chloride, 0.075 M sodium citrate), 5× Denhardt's solution [1% polyvinyl pyrolidone (Sigma, St. Louis, Mo.), 1% ficoll, 1% bovine serum albumin-fraction V], 0.05 M sodium phosphate, pH 6.5, and 50 ng/ml sonicated salmon sperm DNA (Sigma). After overnight hybridization at 42° C., the filters were washed extensively in 2×SSC at 42° C. A hybridizing clone was chosen for plaque purification, DNA isolation, and restriction endonuclease analysis. Hybridizing EcoRI and KpnI fragments were subcloned and subjected to DNA sequence analysis. The sequence demonstrated that the V31 coding sequence had indeed been isolated and matched completely the 114 bp sequence cloned by PCR. However, the sequence did not contain the entire 5' end of the coding region.

Consequently, more V31 genomic sequences were isolated from a different human placenta genomic library in vector lambda-Fix-II (Stratagene). Approximately 600,000 phage were screened by hybridization with the 5' end of the V31 coding sequence (EcoRI-PstI fragment). The probe was pared by labeling approximately 100 ng of the denatured V31 DNA fragment in a reaction containing $^{32}$P-dCTP, $^{32}$P-dTTP, dGTP, dATP, random hexamer primers, and the Klenow fragment of DNA Polymerase I. Unincorporated nucleotides were removed by passing the reaction mixture over a G-25 Sephadex Quick Spin Column (Boehringer Mannheim). The probe was denatured by boiling and then incubated with the phage filters overnight at 42° C. in hybridization solution (50% formnamide, 5×SSC, 5× , Denhardt's, 0.05 M sodium phosphate, pH 6.5) and 50 ng/ml sonicated salmon sperm DNA. Filters were washed three times in 0.2×SSC, 0.1% SDS at 42° C. for 10 minutes. Filters were air dried and then autoradiographed. Six independently hybridizing clones were chosen for plaque purification and restriction endonuclease analysis. Four of these clones produced hybridization patterns identical with genomic Southern blots using the V31 coding sequence probe. The hybridizing 1.9 Kb PstI fragment from one of these phage was isolated and subcloned into the PstI site of plasmid Bluescript SK+ (Stratagene). The resulting plasmid was subjected to DNA sequence analysis and was found to contain the entire V31 coding sequence. The predicted ATG initiation codon was preceded immediately by nucleotides agreeing with the Kozak census sequence for translation initiation [Kozak, *Nucl. Acids Res.*, 12: 857–872 (1984)]. The DNA and amino acid sequences of the V31 genomic clone (ATCC 75327) are respectively presented in SEQ ID NOS: 6 and 7. The sequence of the V31 clone is more homologous to the IL8R1 (31%) and AT2R (27%) than to other members of the 7TM receptor superfamily (e.g., rhodopsin, the adrenergic receptors or the olfactory receptors).

EXAMPLE 3

Isolation of a Human V31 cDNA

A human cDNA encoding the 7TM receptor V31 was isolated. First, a partial cDNA clone was amplified by PCR from a human tonsil cDNA library made by standard methods in vector pCDM8 [Invitrogen, San Diego, Calif.]. The primers utilized in the PCR reaction were:

Primer V31-G+ (SEQ ID NO: 8) GGT GAATTCAGGTTTAAAGTTCCGCAC

Primer CDM8-Down (SEQ ID NO: 9) GCAGAACTG-GTAGGTATGGA

Primer V31-G+ corresponds to the complement of nucleotides 418 to 437 of SEQ ID NO: 6 and includes an EcoRI site (underlined) and three additional nucleotides at its 5' end to facilitate cloning. Primer CDM8-Down annealed to the polylinker of the vector pCDM8. The resulting PCR products were blotted to nitrocellulose and probed with a radioactive V31-specific probe. The radioactive probe was produced by annealling two oligonucleotides, the sequences of which are set out in SEQ ID NOS: 10 and 11, and filling in the ends of the annealled oligonucleotides with $^{32}$P-labelled nucleotides. A hybridizing band was isolated from the gel and cloned in Bluescript (SK−) (Stratagene). The resulting clone was named pV31-5' end and its DNA sequence is set out in SEQ ID NO: 12. Nucleotides 58–117 of pV31-5' end comprise coding sequences that are different from the orignal genomic clone set out in SEQ ID NO: 6, while nucleotides 118–232 are identical to nucleotides 322 to 437 of SEQ ID NO: 6.

A full length cDNA clone was isolated from a peripheral blood mononuclear cell cDNA library. PCR using V31-specific oligonucleotide primers was performed to identify fractions of the library containing V31 clones. The primers utilized were:

Primer V31-B1 (SEQ ID NO: 13) GCACAGCCTTCCT-GTGTGG

Primer V31-reverse (SEQ ID NO: 5)

Primer V31-B1 corresponds to nucleotides 18 to 36 of SEQ ID NO: 12. Individual fractions positive for V31 were plated out and probed with the V31-specific radioactive probe described above for isolation of the V31-5' end clone. Clone PBMC75 was isolated and included a poly-A tail but was five nucleotides shorter at the 5' end than the partial tonsil cDNA set out in SEQ ID NO: 12. The V31 cDNA insert in clone PBMC75, which includes the complete coding sequences for the V31 7TM receptor, was named cDNA V31-B.

Figure 1B:
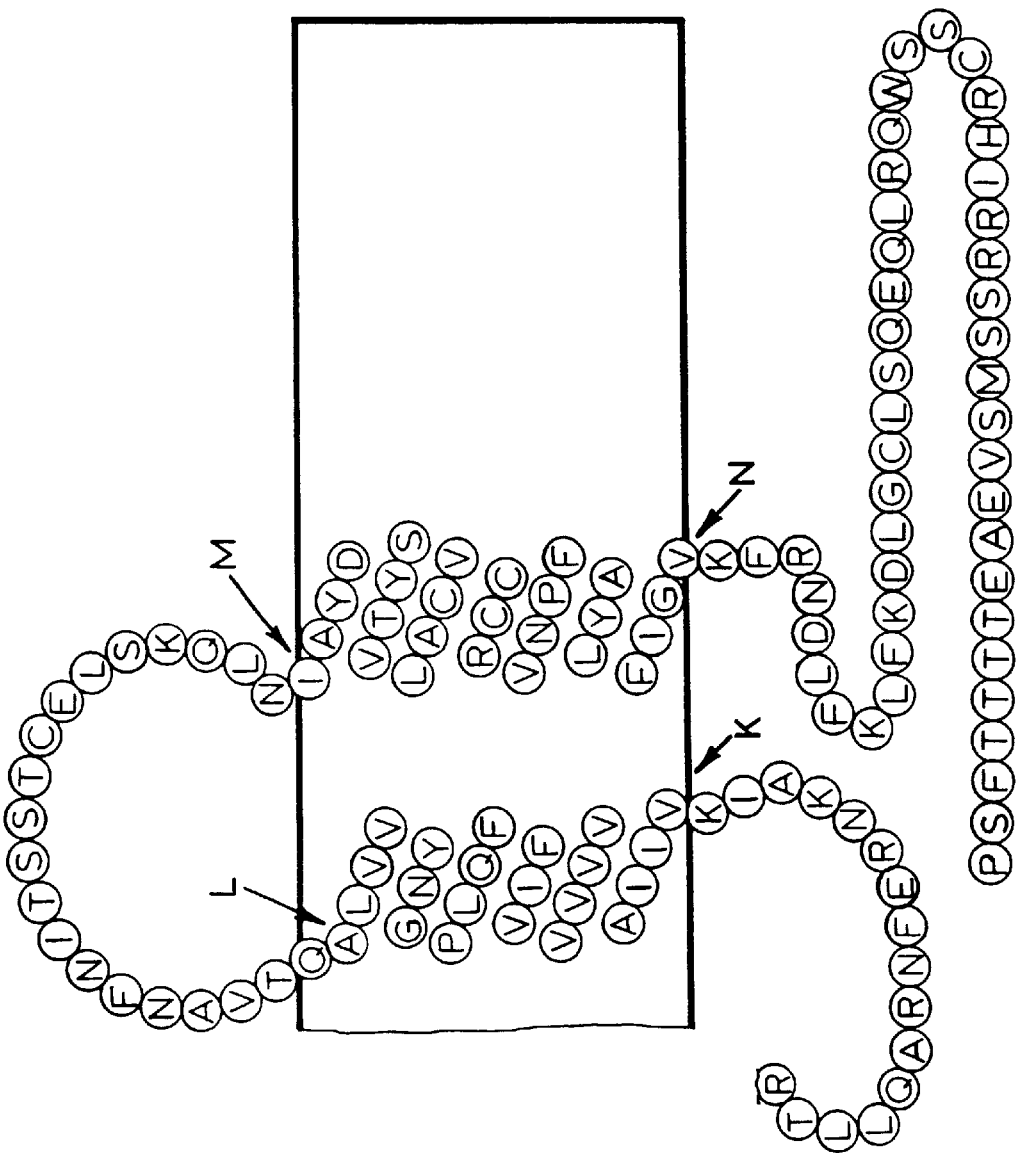

RACE PCR performed using a 5'-Amplifinder RACE kit (Clonetech) was used to amplify and clone the 5' end of the V31 cDNA. Primers V31-F (SEQ ID NO: 52) and V31-G+ (SEQ ID NO: 8) were utilize in the reactions along with primers included in the kit to clone cDNAs which included seventeen additional noncoding nucleotides (five of which were the same as the additional five identified in the original tonsil clone) upstream of the V31-B cDNA. A composite sequence including the seventeen nucleotides and the V31-B cDNA sequence is presented in SEQ ID NO: 14 and in GenBank under Accession No. 131581. The amino acid sequence deduced from the cDNA is presented in SEQ ID NO: 15. The predicted seven transmembrane domains of the V31 7TM receptor (schematically marked in FIG. 1 as regions A to B, C to D, E to F, G to H, I to J, K to L, and M to N) correspond to amino acid residues 58 to 86, 96 to 119, 131 to 152, 171 to 196, 219 to 247, 264 to 285 and 306 to 331 of SEQ ID NO: 15.

Recharacterization of the Human V31 Genomic Clone

A comparison of the amino acid sequence deduced from V31-B with the amino acid sequence deduced from the V31 genomic clone described in Example 2 revealed that the two sequences differed at the amino terminus. The first fifty-two amino acids deduced from the genomic clone (residues 1 to 52 of SEQ ID NO: 7) were not present in the amino acid sequence deduced from V31-B cDNA and were replaced instead with twenty different amino acids (residues 1–20 of SEQ ID NO: 15). This result indicated that that the 5' end of the genomic clone was likely to contain an intron or introns.

Consequently, the V31-B cDNA sequence was used to identify three exons in the human V31 genomic clone described in Example 2. The DNA and deduced amino acid sequences of exons 1 and 3 (along with partial intron sequences) of the V31 genomic clone are set out in SEQ ID NOs: 16 and 17, and 18 and 19, respectively. The DNA sequence of exon 2 of V31 as well as intron sequences flanking the exon are set out in SEQ ID NO: 21 while the deduced amino acid sequence of exon 2 is set out in SEQ ID NO: 22. Nucleotides 151–156 of SEQ ID NO: 16 (exon 1) comprise a putative TATA box while nucleotide 180 appears to be the site of transcription initiation and nucleotides 243–245 appear to comprise the start codon. Another promoter region, a CAAT box, which is thought to modulate transcription by RNA polymerase II [Benoist et al., *Nuc. Acids. Res.*, 8: 127–142 (1980)] has the consensus sequence GG(C/T)CAATCT (SEQ ID NO: 20). A similar sequence sequence is found at nucleotides 104–113 of SEQ ID NO: 16. Amino acids 6–15 of SEQ ID NO: 22 (exon 2) comprise a hydrophobic sequence shorter than, but similar to, that identified in a corresponding region of the serotonin receptor [Ruat et al., *Proc. Natl. Acad. Sci. USA*, 90: 8547–8551 (1993)] as a possible additional transmembrane domain or a cleavable signal sequence. The intron sequences set out in SEQ ID NO: 18 (exon 3) include a stretch of nucleotides encoding an alu repeat.

The sequences of the human V31 exons are also deposited with GenBank as Accession Nos. L31582 (exon 1), L31583 (exon 2) and L31584 (exon 3).

EXAMPLE 4

A murine V31 genomic clone was isolated from a genomic library library made by standard methods from a mouse cell line named C6VL using the 1.9 Kb human V31 gene as a probe. The library was probed at reduced stringency (30% formamide at 42° C.). The DNA and deduced amino acid sequences of the murine V31 genomic clone isolated are set out in SEQ ID NOs: 23 and 24, respectively. The murine cDNA sequence is also deposited in GenBank as Accession No. L31580.

A murine V31 cDNA was also isolated. A mouse thymus cDNA library (Stratagene #935303) was screened using a 1 kb probe generated by PCR with primers specific to the mouse V31 genomic clone:

Nucleotides 692 to 711 of SEQ ID NO: 23
5'-GTGTGCTTCTGCCAAGATGA-3'

Nucleotides 1736 to 1719 of SEQ ID NO: 23
5'-TGCTCACCGACGCGTrCC-3'

The nucleotide and deduced amino acid sequences of the murine V31 cDNA are set out in SEQ ID NOs: 65 and 66.

Both the mouse and human cDNA clones have open reading frames of 1134 nucleotides and encode proteins of 378 amino acids. The deduced amino acid sequences of the two proteins are 86% identical. These proteins contain many of the features common to members of the G protein-coupled receptor family: seven hydrophobic stretches that could serve as transmembrane domains, a pair of cysteines in the second and third extracellular domains, potential N-linked glycosylation sites in the amino terminal extracellular domain, potential phosphorylation sites in the carboxy terminal cytoplasmic domain, and key amino acids conserved among members of the family.

The mouse cDNA clone is 2084 nucleotides in length and contains 175 nucleotides of 5' untranslated sequence and 775 nucleotides 3' untranslated sequence in addition to the coding region of the gene. The mouse and human clones are 85% identical throughout the coding region of the gene, but untranslated sequences 5' and 3' of the coding sequence diverge significantly. The mouse cDNA clone contains two polyadenylation signals at positions 1985–1992 and 2036–2042.

EXAMPLE 5

The PCR fragment, the isolation of which is described in Example 1, encoding the 7TM receptor V28 was used to design synthetic oligonucleotides probes specific for V28. Two overlapping oligonucleotides were synthesized as shown below which represented coding and non-coding strands of the fragment with a 9 bp overlap in the center.

Primer V28L (SEQ ID NO: 25) TGG ACT CAC TAT TTG ATA AAT GAA AAG GGC CTC CAC AAT GCC ATG TGC AAA TTC ACT ACC Primer V28R (SEQ ID NO: 26) AAT GCT GAT GAC GGT GAT GAA GAA TAT GCT TCC AAA AAA GCC GAT GAA GAA GAA GGC GGT AGT GAA The two synthetic DNAs were annealed, and Klenow polymerase was used to incorporate $^{32}$P radiolabeled nucleotides into the resulting V28 specific probe (114 bp in length following reaction). The reaction contained 0.76 µg of each V28 oligonucleotide, 1× Klenow Buffer, 0.015 mM dATP, 0.015 mM dGTP, 10 µl $^{32}$P-dCTP (Amersham), 10 µl α-$^{32}$P-dTTP (Amersham) and 1.5 µl Klenow polymerase. The reaction was incubated at room temperature for 15 minutes and unincorporated counts were removed with the aid of a Quick-Spin G25 column.

The V28 probe (46×10$^6$ cpm) was denatured by boiling for 2 minutes and hybridized to the human placenta genomic library (Stratagene). The library contained 360,000 phage on 12 nitrocellulose filters and hybridization was performed overnight at 42° C. in the hybridization solution described above containing 30% formamide. Filters were washed extensively in 2×SSC at 32° C. and then exposed three days. Several strongly hybridizing signals were observed and plaque purified. The V28 probe hybridized to single restriction endonuclease fragments in Southern blots of the phage DNA and human genomic DNA. Both HindIII (about 2 kbp) and Pst I (about 3.5 kbp) fragments were isolated, subcloned in pBluescript and sequenced. The DNA and deduced amino acid sequences of the full length V28 genomic clone (ATCC 75330) are respectively set out in SEQ ID NOs: 27 and 28. The gene contained the exact V28 sequence isolated by PCR. The encoded amino acid sequence predicts a structure consistent with typical 7TMR structure: there are seven hydrophobic domains separated by hydrophilic domains and highly conserved residues are found in their typical positions. The predicted seven transmembrane domains of the V28 7TM receptor correspond to amino acid residues 26 to 56, 68 to 92, 107 to 125, 146 to 167, 197 to 219, 232 to 253, and 273 to 297 of SEQ ID NO: 28. The V28 coding sequence is 29% homologous with IL8R1 and 27% homologous to AT2R.

EXAMPLE 6

A human V28 cDNA was isolated from a peripheral blood mononuclear cell cDNA library generated by standard methods in vector pRc/CMV (Stratagene). PCR using V28-specific oligonucleotide primers was performed to identify fractions of the library containing V28 clones. The primers utilized were:

Primer V28F (SEQ ID NO: 29) TGG ACT CAC TAT TTG ATA AA

Primer V28X (SEQ ID NO: 30) AAG ATT TGA GAG TCA GAG

Primer V28F corresponds to nucleotides 852 to 871 of SEQ ID NO: 27, while primer V28X corresponds to the complement of nucleotides 2047 to 2064 of SEQ ID NO: 27. The PCR reaction produced a 1.2 Kb DNA product that was labelled with $^{32}$P by random priming and then used as a probe to identify individual V28 clones. Hybridization and washing conditions were similar to the stringent methods described in Example 2.

The DNA and deduced amino acid sequences of the V28 cDNA clone are set out in SEQ ID NOS: 31 and 32, respectively. A comparison of the V28 genomic and cDNA clones revealed that there is an intron in the 5' untranslated portion of the V28 gene, the splice junction for which appear at nucleotides 84 to 85 of SEQ ID NO: 31.

EXAMPLE 7

A human V112 cDNA corresponding to the V112 genomic fragment described in Example 1 was isolated from a macrophage cDNA library made by standard procedures in vector pRc/CMV (Stratagene). PCR using V112-specific oligonucleotide primers was performed to identify fractions of the library containing V112 clones. The primers utilized were:

Primer V112-F (SEQ ID NO: 33) TGGGTGGATAAA-GAAGCATCTC

Primer V112-R (SEQ ID NO: 34) AACACRCATG-CAAGTGAGCA

Primer V112-F corresponds to nucleotides 1 to 19 of SEQ ID NO: 3, while primer V112-R corresponds to the complement of nucleotides 101 to 120 of SEQ ID NO: 3. The PCR reaction produced a 123 bp DNA product that was labeled with $^{32}$P by random priming and then used as a probe to identify individual V112 clones. Hybridization and washing conditions were similar to the reduced stringency methods described in Example 2.

Partial DNA and deduced amino acid sequences of the approximately 850 bp V112 cDNA clone are set out in SEQ ID NOS: 35 and 36, respectively. The partial sequence presented in SEQ ID NO: 35 contains V112 5' untranslated sequence and encodes the amino terminal portion of V112 up to the fourth transmembrane domain. The predicted seven transmbrane domains 1–3 of the V112 7TM receptor correspond to amino acid residues 36 to 58, 70 to 90, and 108 to 127 of SEQ ID NO: 36.

EXAMPLE 8

The R20 sequence isolated by PCR as described in Example 1 was used to screen a genomic library for the entire gene. A probe specific for R20 was prepared by amplifying the R20 partial sequence by PCR using the specific primer sequences set out below and $^{32}$P-labeled nucleotides, wherein primer R20-61 corresponds to the first 21 bases of the coding strand and primer R20-153RC corresponds to the first 20 bases of the non-coding strand.

Primer R20-61 (SEQ ID NO: 37) CTA CAC GTA CCG GGA CTA TGA

Primer R20-53RC (SEQ ID NO: 38) AGA AGA CGC TGG CGT ACA TG

The PCR reaction contained 0.07 µg R20 target sequence (HindIII—Bam fragment isolated from the R20 plasmid cloned in pBlueript SK−), 0.25 mM dATP, 0.25 mM dGTP, 0.25 mM dTTP, 1 µM dCTP, 4 µl $^{32}$P-dCTP (Amersham), 0.01 mg/ml R20 specific primers, 1×PCR buffer, and 0.5 µl Taq polymerase in a volume of 40 µl. The PCR was performed with the following thermocycling parameters: an initial four minutes to bring the reaction to 94° C., followed by 12 cycles of (1) 93° C. denaturation step for 30 seconds, (2) 50° C. annealing step for 30 seconds, and (3) 72° C. extension step for one minute. The unincorporated counts were removed with a Quick-Spin G25 column.

The probe was denatured by boiling for 2 minutes and then used to screen the human plecenta genomic DNA library (Stratagene). Filters were hybridized overnight at 42° C. in hybridization solution containing 40% formamide, washed at 42° C. in 0.2×SSC and exposed overnight. Four strongly hybridizing signals were plaque purified, subcloned and sequenced. The R20 sequence identified by PCR was present in the isolated gene. The gene encodes a protein that has a structure similar to other 7TM receptors. The DNA and deduced amino acid sequences of the full length genomic R20 clone (ATCC 75328) are respectively set out in SEQ ID NOs: 39 and 40. The predicted seven transmembrane domains of the R20 7TM receptor correspond to amino acid residues 28 to 54, 66 to 90, 107 to 125, 146 to 167, 208 to 232, 246 to 267, and 285 to 312 of SEQ ID NO: 40. The R20 gene product is 28% homologous with the IL8R1 and 29% homologous with the AT2R.

EXAMPLE 9

The chromosomal position of the V31 gene was determined by Southern blot analysis of human-murine somatic cell hybrids [Naylor et al., *J. Exp. Med.*, 57: 1020–1027 (1983)] and in situ hybridization of metaphase chromosomes [Cherif et al., Hum. Genet., 81: 358–362 (1989) and Fan et al., *Proc. Natl. Acad. Sci. USA*, 87: 6223–6227 (1990)]. The chromosomal positions of the V28 and R20 genes were also determined by Southern blot analysis of human-murine somatic cell hybrids.

Localization of the V31 Gene

DNA was isolated from human-mouse somatic cell hybrids, digested with EcoRI, and hybridized on Southern blots using the human V31 gene (the 1.9 Kb PstI fragment described in Example 2) as a probe. Hybridization of the V31 gene consistently segregated with human chromosome 17. To localize the V31 gene more specifically, in situ hybridization was performed on human metaphase chromosomes with a fluorescently labelled V31 gene probe (again the 1.9 Kb PstI fragment described in Example 2). Fluorescent in situ hybridization to metaphase chromosomes was used to localize the V31 genomic clone to the q12-q21.2 region of chromosome 17. Metaphase chromosomes were prepared from 5-bromodeoxyuridine synchronized lymphocyte cultures. The probe was biotinylated, hybridized to the chromosome spreads and detected by fluorescein-conjugated avidin (Vector Labs). Slides were evaluated with a Nikon fluorescence microscope. Forty-five metaphase preparations were examined. Q- (DAPI counterstaining) and R-banding (propidium iodide counterstaining) were used to confirm the identity of the chromosome. Fluorescent signal was detected at 17q12-21.2 on both chromatids of chromosome 17 in eighteen out of the forty-five cells. This is the same chromosomal localization identified for inherited familial breast cancer [Hall et al., *Science*, 250: 1684–1689 (1990)].

Localization of the V28 Gene

DNA was isolated from human-mouse somatic cell hybrids, digested with EcoRI, and hybridized on Southern blots using the coding region of the human V28 gene (Example 5) as a probe. Hybridization of the V28 gene consistently segregated with human chromosome 3. To localize the V28 gene specifically, hybridization was observed to a cell line with a 17/3 translocation containing 17qter-17p13::3p21-3pter. This hybrid scored positive and localizes the V28 gene to the p21-ter region of chromosome 3. This region of chromosome 3 has been implicated in the following conditions: von Hippel-Lindau syndrome, thyroid hormone resistance, small cell cancer of lung, Pseudo-Zellweger syndrome, GM1-gangliosidosis and Morquio syndrome (type B). See, O'Brien, Ed., *Genetic Maps: Locus Maps of Complex Genomes*, Sixth Edition, Book 5, pp. 5.108–5.109, Cold Spring Harbor Laboratory Press, Plainview, N.Y. (1993). Interestingly, the gene encoding the CC chemokine receptor, to which the V28 polypeptide exhibits 41% sequence similarity, localizes to the same region of chromosome 3. The CC chemokine receptor recognizes beta chemokines which appear to participate in signalling pathways affecting lymphocytes and macrophages. The 7TM receptor V28 may recognize ligands similar to those recognized by the CC chemokine receptor.

Localization of the R20 Gene

DNA was isolated from human-mouse somatic cell hybrids, digested with EcoRI, and hybridized on Southern blots using the human R20 coding region (Example 8) as a probe. Hybridization of the R20 gene consistently segregated with human chromosome 11. Seven hybrids with chromosome 11 translocations (and no intact chromosome 11) further localize R20 to the p11-p13 region of chromosome 11. This region of chromosome 11 has been implicated in the following conditions: hypoprothrobinemia and dysprothrombinemia (O'Brien et al., supra).

EXAMPLE 10

During the isolation of the R20 gene, two weakly hybridizing sequences were identified which have significant homology to other 7TM receptor genes. The R20 specific probe (described in Example 8) was used to screen a human genomic fetal liver DNA library (ATCC 37333) by the methods described in Example 8. While the R20 gene could not be identified in this library, several weakly hybridizing clones were plaque purified, subcloned, and sequenced. The two clones were designated R2 (ATCC 75329) and R12 (ATCC 75331). The full length DNA and deduced amino acid sequences of R2 and R12 (which are respectively presented in SEQ ID NOS: 41 and 42, and 43 and 44) exhibit homology with other 7TM receptors. The predicted seven transmembrane domains of the R2 7TM receptor correspond to amino acid residues 41 to 69, 77 to 104, 120 to 138, 161 to 186, 207 to 226, 247 to 270, and 294 to 318 of SEQ ID NO: 42, while the predicted seven transmembrane domains of the R12 7TM receptor correspond to amino acid residues 33 to 57, 68 to 90, 106 to 127, 145 to 168, 193 to 217, 233 to 251, and 290 to 312 of SEQ ID NO: 44. R2 is 25% homologous to the IL8R1 and 24% homologous to the AT2R, while R12 is 26% homologous to the IL8R1 and 19% homologous to the AT2R.

EXAMPLE 11

Another novel 7TM receptor was identified by methods similar to those described in Example 1. The two degenerate primer pools (having SEQ ID NOS: 1 and 2, respectively) were used in a PCR reaction containing a human macrophage cDNA library in plasmid pRc/CMV (Stratagene). The reaction mixture contained 1×PCR buffer, 0.25 mM dGTP, 0.25 mM dCTP, 0.25 mM dATP, 0.25 mM TTP, 0.01 μg/μl primer pool 1, 0.01 μg/μl primer pool 2, 0.2 μg human macrophage cDNA library and 2.5 μl Taq polymerase in a reaction volume of 40 μl. When the PCR products were subjected to agarose electrophoresis a faint band of 180–200 bp was observed. To facilitate cloning, this DNA was eluted from the gel and re-amplified by PCR under the same conditions. Substantially more DNA was isolated following the second PCM The re-amplified material was digested with BamHI and HindIII and cloned into the plasmid Bluescript SK–, as described in Example 1. Of sixteen clones sequenced, fourteen corresponded to R20 and two contained a unique sequence termed RM3. Specific primers for the partial RM3 clone were used to identify a full length RM3 cDNA clone by the PCR methods described in Example 2. The DNA and deduced amino acid sequence of the RM3 cDNA are respectively presented in SEQ ID NOs: 45 and 46. The predicted seven transmembrane domains of the RM3 7TM receptor correspond to amino acid residues 48 to 69, 82 to 100, 115 to 136, 159 to 179, 198 to 220, 246 to 274, and 287 to 311 of SEQ ID NO: 46. The sequence of the RM3 partial clone (ATCC 75340) is represented in SEQ ID NO: 45 as nucleotides 438 to 551. The RM3 deduced amino acid sequence exhibits 34% identity to the IL-8R and 32% identity to the AT2R.

EXAMPLE 12

Amino acid identity values among five of the seven novel 7TM receptors described in Examples 1 to 6 as well as values in comparison to various previously identified 7TM receptors are presented in Table 1 below, wherein fMLP is the N-formyl peptide receptor and ThrR is the thrombin receptor. The amino acid sequences of the previously identified 7TM receptors have been published as follows: IL8R1 in Holmes et at., supra; IL8R2 receptor in Murphy et al., *Science*, 253: 1280–1283 (1991); AT2R in Saski et al., supru; C5aR in Gerard and Gerard, supra; fMLPR in Boulay, *BBRC*, 168: 1103–1109 (1990); ThrR in Vu et al., *Cell*, 64: 1057–1068 (1991); and PAFR in Honda et al., supra.

TABLE 1

|       | V31-B | V28 | RM3 | R20 | R12 | R2 |
|-------|-------|-----|-----|-----|-----|----|
| IL8R1 | 33    | 30  | 35  | 28  | 25  | 23 |
| IL8R2 | 34    | 32  | 34  | 30  | 27  | 27 |
| AT2R  | 28    | 28  | 32  | 29  | 28  | 24 |
| C5aR  | 27    | 24  | 26  | 25  | 26  | 27 |
| fMLPR | 25    | 24  | 29  | 24  | 23  | 29 |
| ThrR  | 19    | 25  | 20  | 21  | 29  | 21 |
| PAFR  | 27    | 25  | 23  | 24  | 27  | 20 |
| R2    | 27    | 24  | 24  | 24  | 25  | —  |
| R12   | 23    | 25  | 25  | 29  | —   | —  |
| R20   | 25    | 25  | 26  | —   | —   | —  |
| RM3   | 32    | 33  | —   | —   | —   | —  |
| V28   | 31    | —   | —   | —   | —   | —  |

EXAMPLE 13

V31 genomic DNA was transfected into CHO/DHFR cells (ATCC CRL9096) and 293 cells (ATCC CRL1573) and the cells were assayed for expression of V31 by Northern blot. V28 coding sequences were also transfected into and expressed in 293 cells.

Vector Constructs for Expression of V31 and V28 in Mammalian Cells

The V31 coding sequence was excised from the full length lambda genomic clone described in Example 2 (λS-V31-3) as a 1.9 kb PstI fragment and ligated into commercial plasmid Bluescript SK+ (Stratagene) cut with PstI, to create an intermediate construct designated pV31-Pst. The entire V31 fragment plus 60 bp of flanking polylinker sequence was then cut out of pV31-Pst with HindIII and XbaI and ligated into commercial mammalian expression plasmid pRc/CMV (Invitrogen Corporation, San Diego, Calif.) cut with HindIII and XbaI to generate the expression construct pV31XP.

By standard PCR methods, the entire coding sequence of the V28 gene was isolated from the genomic clone described in Example 5. The coding sequences were then cloned into the expression plasmid pRc/CMV to generate the expression construct 293/V28-L.

Transfection of CHO and 293 Cells

The V31 and V28 expression constructs were transfected into CHO or 293 cells by lipofection using the commercial transfection reagent DOTAP (Boehringer Mannheim Corporation, Indianapolis, Ind.). Following selection for G418 resistance, individual V31 and V28 transfectants were subcloned.

Northern Blot Analysis

Specific expression of the V31 mRNA in transfected cells was assayed by Northern blot hybridization with a $^{32}$P-labelled V31 probe. Transfectants were grown to log phase, then centrifuged and washed one time with Phosphate Buffered Saline. mRNA was isolated from cells using the commercial Micro-Fast Track mRNA isolation kit (Invitrogen Corporation). mRNA species were separated by electrophoresis through 1% agarose gels with 2.2 M form-aldehyde. Samples were first denatured by incubating 15 minutes at 65° C. in 50% formamide and 2.2 M formaldehyde, then bromphenol blue and ethidium bromide were added prior to loading the gel. mRNA was electrophoresed at 50 V for approximately 4 hours. After visualizing by UV trans-illumination and photography, mRNA in the gel was transferred to nitrocellulose (Schleicher & Schuell, Keene, N.H.) by capillary action overnight in 20×SSC. Nitrocellulose blots were baked at 80° C. in a vacuum oven for 1–2 hours prior to hybridizing with probes.

To generate the radiolabelled V31 probe, template DNA (1.9 kb HindIII-XbaI fragment containing entire V31 coding sequence) was denatured by boiling, then annealed to a mixture of random hexamer primers. Primers were extended for 30 minutes at room temperature using Klenow enzyme and a mixture of $^{32}$P-dCTP, $^{32}$P-dTTP, dATP, and dGTP. Unincorporated nucleotides were removed by passing the reaction mixture over a G25 Sephadex Quick Spin Column (Boehiringer Mannheim). Incorporation of $^{32}$P was assessed by Cherenkov counting. The probe was denatured by boiling and then incubated with the mRNA blot overnight at 42° C. in hybridization solution (50% formamide, 5×SSC, 5×Denhardts, 50 mM NaPO4, 10 ug/ml denatured salmon DNA). Blots were washed in 2×SSC, 0.1% SDS at room temperature 2 times for 10 minutes each, and then in 0.1×SSC at 50° C. 3–4 times for 10 minutes each. Blots were air dried and then exposed to X-ray film for varying lengths of time.

Only one of twelve transfected CHO clones expressed V31 mRNA as determined by hybridization. This cell line was designated CHO-V31-10. The signal from this cell line was observable within eight hours, while the other lines failed to produce significant amounts of signal.

Of the nine transfected 293 cell lines, two expressed V31 mRNA at very high levels (designated 293-V31-1 and 293-V31-6), three expressed at moderate levels (designated 293-V31-5, 293-V31-7, and 293-V31-9) and four failed to express significantly.

Also by Northern blot analysis, ten out of twelve 293 clones transfected with V28 coding sequences expressed V28 mRNA. The clone designated V28-k expressed V28 mRNA at the highest levels.

Phenotype of Transfected 293 Cells Expressing V31 mRNA

The phenotype of transfected 293 cells expressing V31 mRNA is altered in comparison to parental 293 cells. Parental 293 cells contain processes which protrude from the cellular surface. Such protrusions (or "spikes") are a common feature of many transformed cell types. The cells do not flatten out onto plastic but show a high profile with localized points of adhesion (thus the spikey description) and do not form a smooth epithelial sheet. In contrast, 293 transfectants expressing high levels of V31 mRNA (293-V31-1 and 293-V31-6) appear flat and smooth in culture. The cells make close and continuous contact with each other to form a smooth epithelial sheet with a cobbled appearance. The V31 transfected 293 cells also exhibit a marked decrease in their growth rate compared with the parental 293 cell line. These morphological and growth rate differences are consistent with a "less transformed" phenotype for V31 gene expression. These results are in marked contrast to other 7TM receptor-transfected cells. For example, the serotonin receptor confers a more transformed phenotype when transfected into mammalian cells [Julius et al., *Science*, 244: 1057 (1989)].

Expression of V31 cDNA in Mammalian Cells

The V31-B cDNA was also engineered for mammalian cell expression in pRc/CMV by methods similar to those described above. The resulting expression plasmid was designated pRcV31-B. The 293 clones transfected with the expression plasmid which were expressing V31-B mRNA exhibited a phenotype similar to parental 293 cells rather than to 293 cells transfected with the V31 genomic DNA constructs. The 293 clone expressing V31 mRNA at the highest levels was V31B-i.

EXAMPLE 14

Expression of mRNA of the novel 7TM receptors V31, V28 and R20 was assayed by Northern blot analysis and in sing hybridization with radio-labelled probes in a variety of human tissues and hematopoietic cell lines.

Hybridization of V31 Probes to Human Tissues in situ

Frozen sections from various human tissues were hybridized in situ with radiolabelled single-stranded RNA probes derived from V31. Tissue samples obtained from lymph node, spleen, thymus, and tonsil were frozen in OTC blocks and stored at −70° C. Blocks were cut into 6 micron sections using a cryostat 2800M (Leica) and applied to slides coated in Vectabond (Vector Laboratories, Burlingame, Calif.). Slides were air dried overnight at room temperature than place at −70° C. for storage. Prior to use, slides were removed from 70° C. and placed at 55° C. for 5 minutes. Sections were then fixed in 4% paraformaldehyde for 20 minutes at 4° C., rinsed 3 times in PBS, dehydrated (70-95-100% ethanol, one minute each at room temperature), and then allowed to dry for 30 minutes. Sections were denatured in 70% formamide, 2×SSC for 2 minutes at 70° C., rinsed in 2×SSC, dehydrated, and then air dried for 30 minutes. The sections were then incubated in prehybridization solution (50% formamide, 0.3 M NaCl, 20 mM Tris pH 8.0, 10% dextran sulfate, 1× Denhardt's solution, 100 mM DTT and 5 mM EDTA) for 2 hours at 42° C., radiolabelled probe was added to the solution ($6\times10^5$ cpm/section) and the sections allowed to hybridize for 12–16 hours at 50° C. To generate sense and anti-sense V31 probes, T7 and T3 RNA polymerases were used to synthesize $^{35}$S-labeled transcripts from a linearized, gel purified plasmid containing a 727 bp HincII fragment of V31.

After hybridization, sections were washed in 4×SSC, 10 mM DTT for 1 hour at room temperature, then in 50% formamide, 1×SSC, 10 mM DTT for 40 minutes at 60° C., and finally in 2×SSC and 0.1×SSC for 30 minutes each at room temperature. After alcohol dehydration, the air dried slides were dipped in Kodak NTB2 Nuclear Emulsion (heated to 42° C.) and allowed to dry for 2 hours at room temperature in complete darkness until time of development. Slides were then placed in Kodak D19 developer for 4 minutes at 4° C., dipped 4 times in Acid Stop (1 ml Glacial acetic acid/500 ml distilled water) and then placed in Kodak fixer for 4 minutes at 4° C. The slides were rinsed 3 times in tap water and then counterstained with hematoxylin/eosin.

The V31 antisense probe hybridized intensely with each of the four human tissue samples (lymph node, spleen, thymus, and tonsil). In contrast, the control probe produced from the V31 sense strand did not hybridize significantly to these tissues.

Northern Blot Analysis of V31 Expression in Human Tissues

Specific expression of of V31 mRNA in normal human tissues was also assayed by Northern blot hybridization. RNA was prepared from human tissues by standard methods [see, for example, Chirgwin et al., *Biochemistry*, 18: 5294–5299 (1979)] and fractionated on oligo-dT cellulose for enrichment of mRNA. The mRNA samples were separated on a formaldehyde-agarose gel, transferred to nitrocellulose and hybridized to the V31 $^{32}$P-labeled probe as described in Example 3. The V31 probe clearly hybridized to the human lymphoid tissues, tonsil, lymph node and spleen. No hybridization was observed to adrenal gland, brain, heart, kidney, liver, lung, pancreas or testis. Small amounts of hybridization were observed to small intestine, which may represent lymphoid projections into this tissue.

Northern Blot Analysis of V31 Expression in Hematopoietic Cell Lines

Cells from several hematopoietic cell lines were grown to log phase, harvested by centrifugation, washed two times with 150 mM NaCl, and the pellets stored frozen at −70° C. To extract RNA, pellets were resuspended in guanidinium isothiocyanate buffer (GIT) and sheared in a polytron mixer for 20 seconds. RNA/GIT mixtures were layered on top of CsCl and centrifuged at 35,000 rpm (179,000×g) for 21 hours. RNA pellets were resuspended in $H_2O$, ethanol precipitated, and treated with Proteinase K to remove any RNase contamination. After a phenol/chloroform extraction, the RNA was reprecipitated, resuspended in $H_2O$ and quantitated spectrophotometrically.

10 ug of each RNA sample was used for northern blot analysis. Samples were denatured and electrophoresed through a formaldehyde/agarose gel, transferred to nitrocellulose and hybridized to the $^{32}$P-labelled V31 probe essentially as described in Example 3.

The V31 probe hybridized strongly to the T cell line Hut 78 and the B cell lines Raji and Jijoye. The T cell line CEM also hybridized with V31, but less intensely. In contrast the T cell lines SKW3 and Molt4 failed to hybridize to V31, as did the myeloid lines KG1, K562, HL-60, and U937. These results confirm the Northern and in situ hybridization results on human tissues; V31 is expressed specifically in lymphoid cells and tissues. Results of Northern blot assays for expression of V31 mRNA in other hematopoietic cell lines are presented below in Table 2.

TABLE 2

|  | V31 Northern Blot Signal |
|---|---|
| T Cell Lines |  |
| H9 | ++ |
| MOLT3 | − |
| JurkatE6-1 | − |
| J.RT3-T3.5 | − |
| CCRF-HSB-2 | + |
| B Cell Lines |  |
| MC116 | + |
| Ramos | − |
| Daudi | − |
| CA46 | − |
| HS602 | ++++ |

Northern Blot Analysis of V28 Expression in Human Tissues and Cell Lines

Expression of V28 mRNA in a variety of human tissues was assayed by northern blot analysis using $^{32}$P-labelled V28 probes. Frozen tissue samples were pulverized in liquid nitrogen using mortar and pestle, and RNA was isolated following the APGC protocol of Chomczynski and Sacchi, *Analytical Biochemistry*, 162: 156–159 (1986). Briefly, samples were homogenized in a 4 M guanidium thiocyanate buffer and then subjected to several rounds of acid phenol extraction and isopropanol precipitation. RNA samples were treated with RNase-free DNase (Stratagene Cloning Systems, La Jolla, Calif.) for 30 minutes at 37° C. to remove any containing DNA, then phenol/chloroform extracted twice, ethanol precipitated, resuspended in DEPC-treated H$_2$O and stored at −70° C. until further use. RNA from cell lines was prepared as described above for the analysis of V31.

Ten to 30 µg of each RNA sample were denatured by incubating in 50% formamide and 3.5 M formaldehyde for 10 minutes at 60° C.; bromphenol blue and ethidium bromide were added prior to electrophoresis. Samples were electrophoresed through 1.2% agarose gels containing 2% formaldehyde for 4 hours at 90 volts. After visualizing by UV trans-illumination and photography, RNA was transferred from the gel to nitrocellulose (Schleicher and Schuell) by capillary action overnight in 20×SSC. Nitrocellulose blots were baked at 80° C. in a vacuum over for 1–2 hours prior to hybridization.

A 1.5 kb Eco RI fragment containing the entire V28 coding sequence was used as a template to generate the radiolabelled V28 probes. Details of the labeling, hybridization and washing are exactly as described in Example 2. Results of the Northern blot analysis are presented in Table 3 below.

TABLE 3

| Tissue or Cell Line | V28 Northern Blot Signal |
|---|---|
| Spleen | + |
| Thymus | + |
| Tonsil | + |
| Lymph Node | +/− |
| Placenta | + |
| Ovary | + |
| Testis | + |
| Kidney | +/− |
| Liver | − |
| Brain | − |
| Heart | − |
| H9 (T cell line) | − |
| MOLT3 (T cell line) | − |
| Daudi (B cell line) | − |
| HL60 (Promyelocytic cell line) | + |
| U937 (Promyelocytic cell line) | + |
| THP.1 (Promyelocytic cell line) | ++++ |

Northern Blot Analysis of R20 in Human Tissues

Expression of the R20 gene in various human tissues was assayed by Northern blot analysis. Poly-A mRNA was isolated from various human tissues, fractionated by denaturing agarose gel electrophoresis, and blotted onto a nitrocellulose membrane.

A probe was prepared from the 1.5 kb HindIII-PstI fragment of R20 as follows. Fifty ng of gel-purified fragment was annealed to 1 µg of random hexamers. The sample was treated with Klenow enzyme in the presence of Klenow buffer (See Example 2), dATP, dGTP, $^{32}$P-dCTP, and $^{32}$P-TTP at room temperature for 75 minutes. The labelled fragment was separated from unincorporated nucleotides by passage through a G-25 Quickspin column (Boehringer Mannheim), denatured by boiling, and cooled on ice. This probe was hybridized to the filter for 16 hours at 42° C. in a solution of 5×SSC, 50 mM NaPO$_4$, 5×Denhardt's solution, and 10 µg/ml salmon sperm DNA. The filter was subsequently washed in 0.1×SSC at 50° C. Hybridization was visualized by autoradiography.

Of the tissues analyzed, the strongest signal was detected in placental RNA. A weaker band of the same apparent molecular weight was also visible in RNA from lymph nodes, kidney, and thymus. No hybridization to liver, ovary, or testis RNA was evident.

EXAMPLE 15

The coding sequence for V31 (and fragments thereof) were engineered for expression in *E. coli* as a fusion protein with Glutathione-S-Transferase (GST) [Smith et al., *Gene*, 67: 31–40 (1988)]. Fusion proteins with GST are generally expressed at high levels and can often be easily purified on glutathione-agarose beads. These fusions are useful for providing material for biochemical studies and as immunogens for the preparation of antibodies.

The entire coding sequence of V31 was engineered for expression in the plasmid pGEX-2T such that a fusion protein was produced containing GST at the amino terminal end and V31 at the carboxyl terminal end. The plasmid pGEX-2T contains a lac promoter which drives the expression of GST. The 3' end of the GST gene contains BamHI and EcoRI sites and encodes a thrombin cleavage site. The V31 gene was cloned into pGEX-2T digested with BamHI and EcoRI by first introducing a BamHI site at the 5' end of the V31 gene and an EcoRI site at its 3' end by PCR directed mutagenesis. A 5' oligonucleotide (V31-A, SEQ ID NO: 47) contained a BamHI site encoding residues 225 and 226 of pGEX-2T and 17 bases of the V31 gene, staring with the methionine initiation codon (ATG). The downstream, antisense oligonucleotide (V31-B, SEQ ID NO: 48) contained an EcoRI site and 17 bases of the 3' end of the V31 coding sequence including the natural stop codon. PCR was performed in a Perkin Elmer Cetus machine with the following thermocycling protocol: an initial four minutes to bring the reaction to 94° C., followed by 25 cycles of (1) 94° C. denaturation step for 30 seconds, (2) 60° C. annealing step for 30 seconds, and (3) 72° C. extension step for 30 seconds. The reaction mixture contained 1×PCR buffer, 0.25 mM dGTP, 0.25 mM dATP, 0.25 mM dCTP, 0.25 mM TTP, 0.01 $\mu g/\mu l$ of each primer, $3\times10^{-7}$ mg template DNA and 2.5 units Taq polymerase in a total reaction volume of 50 $\mu l$. Following PCR, the reaction was extract with phenol and chloroform and ethanol precipitated. The DNA was then digested at 37° C. with BamHI and EcoRI and electrophoresed on 1% agarose/2% Nusieve agarose gel. The predominant PCR product exhibited an electrophoretic mobility consistent with the predicted size of 1241 bp. This DNA was electroluted and then ligated to a pGEX-2T DNA fragment that had been treated with BamHI and EcoRI and isolated by electrophoresis. The ligated DNA was transformed into competent *E. coli* and a clone containing the plasmid designated pGEX-V31-F4 was chosen for analysis. The insert DNA coding for the V31 fusion protein was sequenced by the dideoxy chain termination technique.

A shorter fusion protein, containing only the first 90 amino acids of V31 (the predicted first extracellular domain), was also prepared with GST. Similar to the above example, BamHI and EcoRI sites were introduced into the V31 coding sequence by PCR directed mutagenesis. The 5' oligonucleotide (V31-A) was identical to that utilized for the first GST fusion and contained a BamHI site for the GST gene and 17 bases of the V31 gene. The downstream antisense oligonucleotide (V31-C, SEQ ID NO: 49) contained 18 bases of the V31 gene and introduced a stop codon (after V31 amino acid 90) followed by an EcoRI site. PCR conditions were performed exactly as above for the first GST fusion. The PCR products were phenol/chloroform extracted and digested with BamHI and EcoRI. The DNA was electrophoresed on a 1% agarose/2% Nusieve agarose gel and exhibited a mobility consistent with a predicted size of 281 bp. This DNA was electroeluted and also ligated into pGEX-2T. The insert of the resulting plasmid, pGEX-V31-N1, was confirmed by sequence analysis.

A third fusion protein was prepared which contained GST fused to all of the four putative extracellular domains. Regions of the V31 amino acid sequence were defined as domains based on their predicted hydrophillicity and contained one to five hydrophobic residues at each end (forming portions of transmembrane segments); this design provides some separation between domains and yet does not change the general hydrophilic nature of the fusion protein. Four separate PCR reactions were performed to amplify DNA encoding each separate domain. The method used to then fuse the domain coding sequences is outlined in Erlich, Ed., pp. 61–70 in *PCR Technology*, Stockton Press, New York, (1989). The most 5' oligonucleotide (V31-A) used was identical to that used in the two V31 fusions described in the foregoing paragraphs and contained the BamHI site for ligation to the GST gene sequence. The most 3' oligonucleotide (V31-J, SEQ ID NO: 56) contained 17 bases of the V31 gene and introduced a stop codon after V31 amino acid 343, followed by an EcoRI site.

Oligonucleotide V31-D (SEQ ID NO: 50) was paired with the upstream oligonucleotide V31-A to amplify a 294 bp fragment that coded for the first extracellular domain; the V31-A oligonucleotide also contains 12 bases which are homologous with the second extracellular domain oligonucleotide (V31-E, SEQ ID NO: 51). The second extracellular domain was amplified with oligonucleotides V31-E and V31-F (SEQ ID NO: 52). Oligonucleotide V31-E contains 12 bases of first extracellular domain followed by 17 bases of second extracellular domain sequence. Consequently the 3' end of the first extracellular domain PCR product contains 24 identical nucleotides when compared with the 5' end of the second extracellular domain PCR product allowing the two PCR products to be annealed together and reamplified as a fused DNA fragment (using PCR and oligonucleotides V31-A and V31-F). This strategy was also applied to the third and fourth extracellular domains: the third extracellular domain was amplified using oligos V31-G (SEQ ID NO: 53) and V31-H (SEQ ID NO; 54) and the fourth extracellular domain was amplified using oligos V31-I (SEQ ID NO: 55) and V31-J, and the resulting PCR fragments were annealed and reamplified using oligos V31-G and V31-J. Finally, the two DNA fragments containing the first/second and third/fourth extracellular domains were fused together by annealing the fragments and amplifying with oligonucleotides V31-A and V31-J in a tertiary PCR reaction. PCR conditions and digestion with BamHI and EcoRI were performed as as described for the first two V31 fusion proteins. Products of the initial four PCR reactions were electrophoresed on 1% agarose/2% Nusieve agarose and each reaction yielded the predicted size fragment (294 bp, 75 bp, 105 bp, and 111 bp for extracellular domains one through four, respectively). Secondary reamplification reactions were performed with the same PCR conditions, but the target sequences came from the electrophoresed gels which had been excised by stabbing the appropriate band with a micropipetor tip. The captured agarose (two or three microliters in volume) was then extruded into the secondary PCR reaction. These reactions produced the predicted size DNA fragments of 345 bp (first/second extracellular domains) and 192 bp (third/fourth extracellular domains). These DNA fragments once aneealed were similarly used as template DNA in the final PCR reaction using oligos V31-A and V31-J. The final PCR product was digested with BamHI and EcoRI and exhibited a mobility consistent with the expected 513 bp. The DNA was electroeluted and ligated into pGEX-2T. The resulting plasmid was designated pGEX-V31-X10 and was confirmed to have the predicted DNA sequence.

The amplified sequences and junctions with the GST gene were sequenced to determine that all three designed genes were properly constructed. The three GST/V31 fusion genes were grown in *E. coli* and their synthesis was induced with IPTG. Cultures were grown to late exponential phase and harvested by centrifugation. Cells were resuspended in PBS and disrupted by sonication. Cellular debris was removed by centrifugation and the supernatant was mixed with Glutathione-agarose beads (Sigma). The beads were then extensively washed in PBS. Proteins bound to the beads were eluted with reduced glutathione (Sigma). Aliquots from each stage of purification were analyzed for protein by SDS-polyacrylamide gel electrophoresis. GST is easily purified by this method and represents the major (greater than 90%) protein eluted from glutathione agarose. The GST fusion prote in containing the full length V31 coding sequence produced several protein bands of lower molecular weight (1000, 2500, and 4000 Da larger than GST)

than that predicted for the full length fusion protein. These products were eluted from glutathione-agarose beads, but were expressed at lower levels than GST. These proteins may be the products of the fusion proteolysis (see below). No protein band was observed at the predicted molecular weight for the full length V31-GST fusion protein.

The GST fusion protein containing the first extracellular domain (pGEX-V31-N1) produced several protein bands that were purified on glutathione-agarose. One of these corresponded with the approximate predicted size (10,000 Da larger than GST) and three smaller bands exhibited mobilities identical with the GST fusion protein containing full length V31.

Purification of the GST fusion protein containing all four extracellular domains (pGEX-V31-X10) was also attempted. Only small amounts of protein were eluted from glutathione-agarose beads, and these had the same mobility as the PGEX-V31-F4 bands and the smaller pGEX-V31-X10 bands. However, a large amount of protein remained associated with the cell pellet and exhibited a mobility consistent with the predicted fusion protein size. Amino terminal amino acid sequencing was performed on this electrophoretically purified material, and the sequence was determined to be the amino terminal sequence of GST. This protein may thus represent the GST fusion protein with the four V31 extracellular domains which may form inclusion bodies during synthesis and therefore be insoluble and associated with the cell pellet.

There are several observations that suggest that V31 may recognize a protease The structure of V31 is very similar to the thrombin receptor. V31 shares 30% similarity to the thrombin receptor and both molecules have unusually long first extracellular domains (89 residues for V31, 100 for thrombin). The thrombin receptor contains a thrombin cleavage site in this first extracellular domain and the receptor becomes activated following proteolysis. V31 contains a prominent proteolytic recognition sequence including five adjacent lysines (amino acid positions 18–22) that should be a good target for a protease specific for basic residues (several such proteases exist, such as trypsin). Moreover, experimental observations with GST-V31 fusion proteins suggest that the first extracellular domain is an obvious target for an E. coli protease. During the isolation of each of the three fusion proteins, some of the material was found to be partially degraded as described in the foregoing paragraphs. The sites of proteolysis are presumably in the first extracellular domain since that is the only sequence common to the three fusion proteins. The size (2500 Da larger than GST) of at least one of these potential degradation products is consistent with cleavage at or near adjacent lysines. This result suggests that the first extracellular domain is accessible to cleavage by E. coli proteases; such accessibility to a human protease may result in cleavage and subsequent V31 signal transduction events in vivo.

EXAMPLE 16

The extracellular domains of the R20 sequence were also engineered for expression in E. coli as a fusion protein with GST. As described in Example 15 for V31 domains, the R20 domains were chosen by their predicted hydrophillicity. Four independent PCR reactions were performed to amplify each domain.

The 5' oligonucleotide (R2X1, SEQ ID NO: 57) encodes a BamHI site for ligation to the GST gene, followed by 15 nucleotides of the R20 gene (beginning with the methionine initiation codon). The most 3' oligonucleotide (R20-Y4, SEQ ID NO: 64) contained 18 residues of the R20 gene (fourth extracellular coding segment), introduced a stop codon after R20 amino acid 286, and was followed by an EcoRI site. The first extracellular domain coding sequence was prepared by PCR with oligonucleotides R20-X1 and R20-Y1 (SEQ ID NO: 58) using conditions described in Example 15. Similarly, the second, third, and fourth extracellular domain coding sequences were amplified with primer pairs R2-X2 (SEQ ID NO: 59) and R20-Y2 (SEQ ID NO: 60); R20-X3 (SEQ ID NO: 61) and R20-Y3 (SEQ ID NO: 62); and R20-X4 (SEQ ID NO: 63) and R20-Y4, respectively. The first and second extracellular domain coding sequences were fused together by a secondary PCR reaction, similar to that described in Example 15 (primers R20-Y1 and R20-X2 share 30 overlapping nucleotides which allow the two primary PCR products to anneal together for the amplification of a fused DNA fragment; the PCR reaction contains the two primary PCR products and primers R20-X1 and R20-Y2). The third and fourth extracellular domain coding sequences were similarly fused together in a PCR reaction with primers R20-X3 and R20-Y4. Finally, the PCR products from the secondary reactions were annealed and amplified in a tertiary PCR with primers R20-X1 and R20-Y4; this reaction produced a DNA which encoded the four extracellular domains. The DNA was digested with BamHI and EcoRI and then ligated into pGEX-2T as described in Example 15. The resulting plasmid was designated pGEX-RDF6 and the insert was confirmed by DNA sequence analysis.

As described in Example 15, E. coli harboring this plasmid were grown and analyzed for production of a GST-R20 domain fusion protein. A protein band of the appropriate mobility was observed on SDS-PAGE of glutathione agarose purified material. Several lower molecular weight species (about 1000 Da smaller) were also observed which may represent proteolytic cleavage products. All of these bands could be cleaved with thrombin to yield a band which co-migrated with GST. This result suggests that the E. coli cultures produce GST fusion proteins with R20 extracellular domain sequences. The material purified on glutathione agarose was directly used for immunization of mice for the preparation of antibodies as described below in Example 18.

EXAMPLE 17

By methods similar to those described in Examples 15 and 16, V31-B and V28 coding sequences were engineered to be expressed as GST fusion proteins.

The coding sequence of interest (from the V31-B cDNA described in Example 3 or the V28° cDNA described in Example 6) was cloned into the BamHI and EcoRI sites of pGEX-2T. Single bacterial colonies containing the resulting V31-B or V28 $\mu$plasmids were used to inoculate 50 ml L broth/carbenicillin and was grown overnight at 37° C. The overnight cultures were diluted 10-fold to 500 ml with L broth/carbenicillin and incubated for 1.5 hours at 37° C. IPTG was added to 1 mM and the culture was incubated for 3.5 hours at 37° C. Bacteria were pelleted, resuspended in 15 ml PBS/1% Triton X-100 and sonicated with five 45-second bursts while keeping ice cold. Homogenate was aliquoted and spun in a microfuge at full speed for 5 minutes. Pellets were resuspended in a total of 3 ml PBS/1% Triton X-100. Half of the sample was brought to 10 ml with 3.5 ml $H_2O$, 4.5 ml 2×sample buffer and 0.5 ml 2M DTT. The sample was boiled for 3 minutes and spun before loading on two 10% acrylamide SDS preparative gels. Gels were run at 30 mA for approximately 15 hours then incubated in ice cold 0.4 M KCl to visualize protein bands. The induced band was cut out and electroeluted for 4 hours at 50 mA into approximately 10 ml Tris-glycine buffer (no SDS) in dialysis tubing. When necessary, the eluted fusion protein was concentrated in Amicon microconcentrators with 30 kD moleculear weight cut-off.

EXAMPLE 18

Generation of Antibodies to V31 and V28 Fusion Proteins

The GST-V31 fusion proteins V31-N1 and V31-X10 described in Example 15 were purified on glutathione-agarose and emulsified with an equal volume of Freunds adjuvant (complete for the first injection and incomplete for all subsequent injections). Two Balb/c mice were initially immunized subcutaneously with approximately 200 µl of each construct. Subsequent boosts were made at two week intervals and the mice were bled retro-orbitally after three boosts.

Immunological reactivity was assessed by Western blot analysis. Approximately 25 µg of either the immunizing protein or GST was resolved on a 10% polyacrylamide gel and transferred to nitrocellulose. The filter was blocked in PBS containing 5% non-fat dried milk and 1% BSA for 2–15 hours at 4° C. The sera (either pre-immune or immune) was diluted 1:50 in blocking buffer in a final volume of 2 ml, incubated with the filter strip for 1 hour at 4° C. and washed three times with 50 ml of PBS. Sheep anti-mouse Ig conjugated to horseradish peroxidase (Amersham) was diluted 1:500 in PBS and incubated with each filter for 1 hour at 4° C. The filters were washed 3 times in 100 ml of PBS and placed in 5 ml of 3,3' diaminobenzidine (0.6 mg/ml in 10 mM Tris-HCl; 0.6% $NiCl_2$; 0.06% $H_2O_2$). Immunoreactivity to V31 fusion proteins was observed from sera of mice immunized to V31-N1 and V31-X10. In addition, immunoreactivity was observed to the thrombin cleaved V31-N1 products (both GST and the V31 amino terminal domain).

The extracellular domains of V31-B and V28 were also used to immunize rabbits as GST fusion proteins. Antibodies raised in rabbits recognized the respective fusion protein on Western blots. In addition, the antiserum also recognized the respective fusion protein on Western blots and the thrombin cleaved fusion proteins including the fragments corresponding to the extracellular domains of V31B or V28.

Generation of Antibodies to V31 Peptides

V31 peptides to be used to generate V31 specific antibodies include, for example:

Peptide ECDN-B (Amino acids 1 to 15 of SEQ ID NO: 15) MDLGKPMKSVLC

Amino acid residue 12 (a cysteine) was added to the peptide to facilitate conjugation of the peptide to an immunogen carrier. Another peptide is:

Peptide ECD2 (Amino acids 116 to 129 of SEQ ID NO: 15) YSAAKSWVFGVHFC

Peptide ECDN-B corresponds to the amino terminal end of the first extracellular domain of V31 while peptide ECD2 corresponds to a region of the second extracellular domain of V31.

EXAMPLE 19

Various methods may be used to identify extracellular and intracellular ligands for the 7TM receptors of the invention. For example, because 7TM receptors are coupled to G proteins to effect biological responses, the secondary signal transduction events [reviewed by Linder et al., *Sci. Am.*, 267: 56–65, (1992)] that are utilized by G proteins can be utilized to assay for recombinant 7TM receptor function. Assays for the activity of G protein effector molecules (e.g., adenylyl cyclase, phospholipase C, ion channels, and phosphodiesterases) have previously been described. For example, concentration of cyclic AMP can be measured by a commercial radioimmunoassay; phosphoinositide production can easily be monitored [Downes et al., *Biochem. J.*, 198: 133–140 (1981)]; and the transient release of intracellular calcium ion stores can be observed with spectrofluorimetry. These assays can be performed on mammalian cells expressing 7TM receptors of the invention in the presence and absence of test compounds to identify or purify potential ligands of the 7TM receptors and such assays may also be used for the identification or purification of agonists or antagonists of 7TM receptors.

As another example, a calcium flux assay can be used to identify solutions or cellular extracts containing ligands for 7TM recpetors of the invention. Specifically, 293 cells transfected with DNA sequences of the invention encoding a 7TM receptor are grown in a 10 cm dish to ~90% confluence in MEM+10% serum. Cells are washed with CMF-PBS and loaded with Fura-2 by incubating in 4 ml MEM+10% serum+1 uM Fura-2 AM (Molecular Probes—1 mM stock made in DMSO and frozen in aliquots) for 30 minutes at room temperature. Cells are again washed and removed from plate with versene. Cells are pelleted, washed in D-PBS (containing 1 mM $Ca^{++}$) and resuspended in ~500 ul D-PBS for a concentration of ~$10^7$/ml. Fluorescence changes are monitored in a Hitachi F-4010 fluorescence spectrophotometer. Approximately $10^6$ cells are suspended in a total of 1.8 ml D-PBS with stirring in a cuvette maintained at 37° C. Excitation wavelengths alternate between 340 nm and 380 nm at 4 second intervals while emission is monitored at 510 nm. Test compounds are added through an injection port. At the end of the experiment, ionomycin is added to measure the maximal $Ca^{++}$ flux.

A transient $Ca^{++}$ flux is indicative of the presence of a ligand for the 7TM receptor in the solution being tested.

Transfected 293 cell line expressing V28 or V31 RNA (Example 13) were examined in the $Ca^{++}$ flux assay using several chemokines as potential ligands for the 7TM receptors. None of the tested ligands stimulated a $Ca^{++}$ flux through either V28 or V31. The chemokines tested were: EL8, NAP-2, GRO/MGSA, IP-10, M1P-1α, M1P-1β, MCP-1, and RANTES. There were two controls for the assay. First, untransfected 293 cells express the thrombin receptor and treatment of untransfected 293 cells with thrombin resulted in an observable $Ca^{++}$ flux. Second, 293 cells were transfected with sequences encoding the IL-8 receptor and treatment of transfected cells with IL-8 also resulted in an observable $Ca^{++}$ flux.

The foregoing illustrative examples relate to presently preferred embodiments of the invention and numerous modifications and variations thereof will be expected occur to those in the art. Thus only such limitations as appear in the appended claims should be placed upon the scope of the present invention.

What is claimed is:

1. An antibody that specifically binds a polypeptide comprising the R2 seven transmembrane receptor amino acid sequence in SEQ ID NO: 42.

2. A hybridoma that produces a monoclonal antibody according to claim 12.

3. An antibody according to claim 1 that is a humanized antibody.

4. An antibody according to claim 1 that specifically binds an extracellular epitope of the R2 seven transmembrane receptor.

5. An antibody according to claim 1 that specifically binds to the amino-terminal extracellular domain of the R2 seven transmembrane receptor.

6. A composition comprising polyclonal antibodies, wherein at least one of said antibodies is an antibody according to claim 1.

7. A polypeptide comprising a fragment of an antibody according to claim 1, wherein said fragment and said polypeptide bind to the R2 seven transmembrane receptor.

8. A polypeptide according to claim 7 that is selected from the group consisting of single chain antibodies and CDR-grafted antibodies.

9. A composition comprising a polypeptide according to claim 7 and a pharmaceutically-acceptable diluent or carrier.

10. An antiserum produced by a process comprising the steps of:

immunizing a mammal with a composition comprising a R2 seven transmembrane receptor polypeptide having the amino acid sequence set forth in SEQ ID NO: 42 or fragment thereof, wherein said fragment comprises at least one R2 extracellular or intracellular domain; and obtaining antiserum from said mammal after said immunizing step, said antiserum containing antibodies that bind to the R2 seven transmembrane receptor.

11. An antiserum according to claim 10 wherein the mammal is immunized multiple times prior to obtaining antiserum from said mammal.

12. An antiserum according to claim 10 wherein said R2 polypeptide or fragment is purified prior to said immunizing step, and wherein said composition further includes an adjuvant.

13. Polyclonal antibodies purified from an antiserum according to claim 10, said polyclonal antibodies comprising antibodies that bind to said R2 polypeptide.

14. A method of modulating ligand/antiligand binding of a R2 seven transmembrane receptor comprising the step of contacting said R2 seven transmembrane receptor with a polypeptide according to claim 7.

15. A purified and isolated polynucleotide comprising a nucleotide sequence encoding the amino acid sequence of R2 seven transmembrane receptor set out in SEQ ID NO: 42.

16. A host cell stably transformed or transfected with a polynucleotide according to claim 15 in a manner allowing the expression in said host cell of the R2 seven transmembrane receptor polypeptide encoded by the polynucleotide.

17. A purified and isolated R2 seven transmembrane receptor comprising the amino acid sequence set out in SEQ ID NO: 42.

* * * * *

SEQUENCE LISTING (1) GENERAL INFORMATION:

(iii) NUMBER OF SEQUENCES: 66

(2) INFORMATION FOR SEQ ID NO: 1:

(i) SEQUENCE CHARACTERISTICS:
       (A) LENGTH: 69 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 1:

GACGGATCCG TTTTTCTGTT GAATTTGGCT CTGGCTGACY TAYKCTTTKY MCTGACYTTG      60

CCMMTSTGG                                                             69

(2) INFORMATION FOR SEQ ID NO: 2:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: modified_base
       (B) LOCATION: 12
       (D) OTHER INFORMATION: /note= "The modified base at this
           position is an inosine."

(ix) FEATURE:
       (A) NAME/KEY: modified_base
       (B) LOCATION: 15
       (D) OTHER INFORMATION: /note= "The modified base at this
           position is an inosine."

(ix) FEATURE:
       (A) NAME/KEY: modified_base
       (B) LOCATION: 18
       (D) OTHER INFORMATION: /note= "The modified base at this
           position is an inosine."

(ix) FEATURE:
       (A) NAME/KEY: misc_difference
       (B) LOCATION: replace(21, "")
       (D) OTHER INFORMATION: /note= "The nucleotide at this
           position may be a Y(C or T or U) or may be an inosine."

(ix) FEATURE:
       (A) NAME/KEY: modified_base
       (B) LOCATION: 27
       (D) OTHER INFORMATION: /note= "The modified base at this
           position is an inosine."

(xi) SEQUENCE DESCRIPTION: SEQ ID NO: 2:

GGCTAAGCTT GNACNATNGC NAGRTANCGR TC                                   32

(2) INFORMATION FOR SEQ ID NO: 3:

(i) SEQUENCE CHARACTERISTICS:
       (A) LENGTH: 120 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 3:

```
GTGGATAAAG AAGCATCTCT AGGACTGTGG AGGACGGGCT CCTTCCTGTG CAAAGGGAGC    60

TCCTACATGA TCTCCGTCAA TATGCACTGC AGTGTCCTCC TGCTCACTTG CATGAGTGTT   120
```

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

```
TGGGCCTACA GCGCGGCCAA                                                 20
```

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

```
TCAATGCTGA TGCAAAGAAG                                                 20
```

(2) INFORMATION FOR SEQ ID NO: 6:

(i) SEQUENCE CHARACTERISTICS:
        (A) LENGTH: 2058 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 166..1395

(xi) SEQUENCE DESCRIPTION: SEQ ID NO: 6:

```
GATGAACCAC TATTCCTCCG CCTGGGCAAC ATGGCAGAAT CCCATCTCTA CTAAAAATAC    60

AAAAATTCGC TGGGGTGTGG TGGCATAAGG CTGTGGTCCC AGCTACTCAG GAGGCTGAAG   120

TGGAAGGATC ACCTGAGCCT GGAGAGGCCG AGGCTGCAGG GAGCC ATG ATT GCA       174
                                                  Met Ile Ala
                                                    1

CCA CTG CAC TCC AGC CTG GGC AAC AGA GTG AGA CCA TGT CTC AAG AAA    222
Pro Leu His Ser Ser Leu Gly Asn Arg Val Arg Pro Cys Leu Lys Lys
      5                  10                  15

AAA AAA AAA GAA AGA AAC CAC TGC TCT AGG CTA AAT CCC AGC CAG AGT    270
Lys Lys Lys Glu Arg Asn His Cys Ser Arg Leu Asn Pro Ser Gln Ser
 20                  25                  30                  35

TGG AGC CAC CCA GCT AAA CTG GCC TGT TTT CCC TCA TTT CCT TCC CCG    318
Trp Ser His Pro Ala Lys Leu Ala Cys Phe Pro Ser Phe Pro Ser Pro
                 40                  45                  50

AAG GTA TGC CTG TGT CAA GAT GAG GTC ACG GAC GAT TAC ATC GGA GAC    366
Lys Val Cys Leu Cys Gln Asp Glu Val Thr Asp Asp Tyr Ile Gly Asp
             55                  60                  65

AAC ACC ACA GTG GAC TAC ACT TTG TTC GAG TCT TTG TGC TCC AAG AAG    414
```

```
                Asn Thr Thr Val Asp Tyr Thr Leu Phe Glu Ser Leu Cys Ser Lys Lys
                             70                  75                  80

GAC GTG CGG AAC TTT AAA GCC TGG TTC CTC CCT ATC ATG TAC TCC ATC                462
Asp Val Arg Asn Phe Lys Ala Trp Phe Leu Pro Ile Met Tyr Ser Ile
         85                  90                  95

ATT TGT TTC GTG GGC CTA CTG GGC AAT GGG CTG GTC GTG TTG ACC TAT                510
Ile Cys Phe Val Gly Leu Leu Gly Asn Gly Leu Val Val Leu Thr Tyr
100                 105                 110                 115

ATC TAT TTC AAG AGG CTC AAG ACC ATG ACC GAT ACC TAC CTC CTC AAC                558
Ile Tyr Phe Lys Arg Leu Lys Thr Met Thr Asp Thr Tyr Leu Leu Asn
                    120                 125                 130

CTG GCG GTG GCA GAC ATC CTC TTC CTC CTG ACC CTT CCC TTC TGG GCC                606
Leu Ala Val Ala Asp Ile Leu Phe Leu Leu Thr Leu Pro Phe Trp Ala
                135                 140                 145

TAC AGC GCG GCC AAG TCC TGG GTC TTC GGT GTC CAC TTT TGC AAG CTC                654
Tyr Ser Ala Ala Lys Ser Trp Val Phe Gly Val His Phe Cys Lys Leu
            150                 155                 160

ATC TTT GCC ATC TAC AAG ATG AGC TTC TTC AGT GGC ATG CTC CTA CTT                702
Ile Phe Ala Ile Tyr Lys Met Ser Phe Phe Ser Gly Met Leu Leu Leu
165                 170                 175

CTT TGC ATC AGC ATT GAC CGC TAC GTG GCC ATC GTC CAG GCT GTC TCA                750
Leu Cys Ile Ser Ile Asp Arg Tyr Val Ala Ile Val Gln Ala Val Ser
180                 185                 190                 195

GCT CAC CGC CAC CGT GCC CGC GTC CTT CTC ATC AGC AAG CTG TCC TGT                798
Ala His Arg His Arg Ala Arg Val Leu Leu Ile Ser Lys Leu Ser Cys
                    200                 205                 210

GTG GGC ATC TGG ATA CTA GCC ACA GTG CTC TCC ATC CCA GAG CTC CTG                846
Val Gly Ile Trp Ile Leu Ala Thr Val Leu Ser Ile Pro Glu Leu Leu
                215                 220                 225

TAC AGT GAC CTC CAG AGG AGC AGC AGT GAG CAA GCG ATG CGA TGC TCT                894
Tyr Ser Asp Leu Gln Arg Ser Ser Ser Glu Gln Ala Met Arg Cys Ser
            230                 235                 240

CTC ATC ACA GAG CAT GTG GAG GCC TTT ATC ACC ATC CAG GTG GCC CAG                942
Leu Ile Thr Glu His Val Glu Ala Phe Ile Thr Ile Gln Val Ala Gln
245                 250                 255

ATG GTG ATC GGC TTT CTG GTC CCC CTG CTG GCC ATG AGC TTC TGT TAC                990
Met Val Ile Gly Phe Leu Val Pro Leu Leu Ala Met Ser Phe Cys Tyr
260                 265                 270                 275

CTT GTC ATC ATC CGC ACC CTG CTC CAG GCA CGC AAC TTT GAG CGC AAC               1038
Leu Val Ile Ile Arg Thr Leu Leu Gln Ala Arg Asn Phe Glu Arg Asn
                    280                 285                 290

AAG GCC ATC AAG GTG ATC ATC GCT GTG GTC GTG GTC TTC ATA GTC TTC               1086
Lys Ala Ile Lys Val Ile Ile Ala Val Val Val Val Phe Ile Val Phe
                295                 300                 305

CAG CTG CCC TAC AAT GGG GTG GTC CTG GCC CAG ACG GTG GCC AAC TTC               1134
Gln Leu Pro Tyr Asn Gly Val Val Leu Ala Gln Thr Val Ala Asn Phe
            310                 315                 320

AAC ATC ACC AGT AGC ACC TGT GAG CTC AGT AAG CAA CTC AAC ATC GCC               1182
Asn Ile Thr Ser Ser Thr Cys Glu Leu Ser Lys Gln Leu Asn Ile Ala
325                 330                 335

TAC GAC GTC ACC TAC AGC CTG GCC TGT GTC CGC TGC TGC GTC AAC CCT               1230
Tyr Asp Val Thr Tyr Ser Leu Ala Cys Val Arg Cys Cys Val Asn Pro
340                 345                 350                 355

TTC TTG TAC GCC TTC ATC GGC GTC AAG TTC CGC AAC GAT CTC TTC AAG               1278
Phe Leu Tyr Ala Phe Ile Gly Val Lys Phe Arg Asn Asp Leu Phe Lys
                    360                 365                 370

CTC TTC AAG GAC CTG GGC TGC CTC AGC CAG GAG CAG CTC CGG CAG TGG               1326
Leu Phe Lys Asp Leu Gly Cys Leu Ser Gln Glu Gln Leu Arg Gln Trp
                375                 380                 385
```

```
TCT TCC TGT CGG CAC ATC CGG CGC TCC TCC ATG AGT GTG GAG GCC GAG    1374
Ser Ser Cys Arg His Ile Arg Arg Ser Ser Met Ser Val Glu Ala Glu
        390                 395                 400

ACC ACC ACC ACC TTC TCC CCA TAGGCGACTC TTCTGCCTGG ACTAGAGGGA       1425
Thr Thr Thr Thr Phe Ser Pro
        405             410

CCTCTCCCAG GGTCCCTGGG GCGGGGATAG GGAGNAGATG CAATGACTCA GGACATCCCC  1485

CCGCCAAAAG CTGCTCAGGG AAAAGCAGCT CTCCCCTCAG AGTGCAAGCC CTGCTCCAGA  1545

AGTTAGCTTC ACCCCAATCC CAGCTACCTC AACCAATGCC GAAAAGACA GGGCTGATAA   1605

GCTAACACCA GACAGACAAC ACTGGGAAAC AGAGGCTATT GTCCCCTAAA CCAAAAACTG  1665

AAAGTGAAAG TCCAGAAACT GTTCCCACCT GCTGGAGTGA AGGGGCCAAG GAGGGTGAGT  1725

GCAAGGGGCN GTGGGAGTGG CCTGAAGAGT CCTCTGAATG AACCTTCTGG CCTCCCACAG  1785

ACTCAAATGC TCAGACCAGC TCTTCCGAAA ACCAGGCCTT ATCTCCAAGA CCAGAGATAG  1845

TGGGGAGACT TCTTGGCTTG GTGAGGAAAA GCGGACATCA GCAGCTGGTC AAACAAACTC  1905

TCTGAACCCC TCCCTCCATC GTTTTCTTCA CTGTCCTCCA AGCCAGCGGG AATGCAGCTG  1965

CCACGCCGCC CTAAAAGCAC ACTCATCCCC TCACTTGCCG CGTCGCCCTC CCAGGCTCTC  2025

AACAGGGGAG AGTGTGGTGT TTCCTTCCTG CAG                              2058
```

(2) INFORMATION FOR SEQ ID NO: 7:

(i) SEQUENCE CHARACTERISTICS:
        (A) LENGTH: 410 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Ile Ala Pro Leu His Ser Ser Leu Gly Asn Arg Val Arg Pro Cys
 1               5                  10                  15

Leu Lys Lys Lys Lys Glu Arg Asn His Cys Ser Arg Leu Asn Pro
            20                  25                  30

Ser Gln Ser Trp Ser His Pro Ala Lys Leu Ala Cys Phe Pro Ser Phe
        35                  40                  45

Pro Ser Pro Lys Val Cys Leu Cys Gln Asp Glu Val Thr Asp Asp Tyr
    50                  55                  60

Ile Gly Asp Asn Thr Thr Val Asp Tyr Thr Leu Phe Glu Ser Leu Cys
65                  70                  75                  80

Ser Lys Lys Asp Val Arg Asn Phe Lys Ala Trp Phe Leu Pro Ile Met
                85                  90                  95

Tyr Ser Ile Ile Cys Phe Val Gly Leu Leu Gly Asn Gly Leu Val Val
                100                 105                 110

Leu Thr Tyr Ile Tyr Phe Lys Arg Leu Lys Thr Met Thr Asp Thr Tyr
            115                 120                 125

Leu Leu Asn Leu Ala Val Ala Asp Ile Leu Phe Leu Leu Thr Leu Pro
        130                 135                 140

Phe Trp Ala Tyr Ser Ala Ala Lys Ser Trp Val Phe Gly Val His Phe
145                 150                 155                 160

Cys Lys Leu Ile Phe Ala Ile Tyr Lys Met Ser Phe Phe Ser Gly Met
                165                 170                 175

Leu Leu Leu Leu Cys Ile Ser Ile Asp Arg Tyr Val Ala Ile Val Gln
                180                 185                 190

Ala Val Ser Ala His Arg His Arg Ala Arg Val Leu Leu Ile Ser Lys
```

```
                195                 200                 205
Leu Ser Cys Val Gly Ile Trp Ile Leu Ala Thr Val Leu Ser Ile Pro
    210                 215                 220
Glu Leu Leu Tyr Ser Asp Leu Gln Arg Ser Ser Glu Gln Ala Met
225                 230                 235                 240
Arg Cys Ser Leu Ile Thr Glu His Val Glu Ala Phe Ile Thr Ile Gln
                245                 250                 255
Val Ala Gln Met Val Ile Gly Phe Leu Val Pro Leu Leu Ala Met Ser
            260                 265                 270
Phe Cys Tyr Leu Val Ile Ile Arg Thr Leu Leu Gln Ala Arg Asn Phe
        275                 280                 285
Glu Arg Asn Lys Ala Ile Lys Val Ile Ala Val Val Val Val Phe
    290                 295                 300
Ile Val Phe Gln Leu Pro Tyr Asn Gly Val Val Leu Ala Gln Thr Val
305                 310                 315                 320
Ala Asn Phe Asn Ile Thr Ser Ser Thr Cys Glu Leu Ser Lys Gln Leu
                325                 330                 335
Asn Ile Ala Tyr Asp Val Thr Tyr Ser Leu Ala Cys Val Arg Cys Cys
            340                 345                 350
Val Asn Pro Phe Leu Tyr Ala Phe Ile Gly Val Lys Phe Arg Asn Asp
        355                 360                 365
Leu Phe Lys Leu Phe Lys Asp Leu Gly Cys Leu Ser Gln Glu Gln Leu
    370                 375                 380
Arg Gln Trp Ser Ser Cys Arg His Ile Arg Arg Ser Ser Met Ser Val
385                 390                 395                 400
Glu Ala Glu Thr Thr Thr Thr Phe Ser Pro
                405                 410

(2) INFORMATION FOR SEQ ID NO: 8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

GGTGAATTCA GGCTTTAAAG TTCCGCAC                                28

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

GCAGAACTGG TAGGTATGGA                                        20

(2) INFORMATION FOR SEQ ID NO: 10:

(i) SEQUENCE CHARACTERISTICS:
        (A) LENGTH: 60 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO: 10:

GTATGCCTGT GTCAAGATGA GGTCACGGAC GATTACATCG GAGACAACAC CACAGTGGAC        60

(2) INFORMATION FOR SEQ ID NO: 11:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 11:

TTAAAGTTCC GCACGTCCTT CTTGGAGCAC AAAGACTCGA ACAAAGTGTA GTCCACTGTG        60

(2) INFORMATION FOR SEQ ID NO: 12:

(i) SEQUENCE CHARACTERISTICS:
            (A) LENGTH: 238 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 12:

GAATTCTGCG AGGCCGGGCA CAGCCTTCCT GTGTGGTTTT ACCGCCCAGA GAGCGTCATG        60

GACCTGGGGA AACCAATGAA AAGCGTGCTG GTGGTGGCTC TCCTTGTCAT TTTCCAGGTA       120

TGCCTGTGTC AAGATGAGGT CACGGACGAT TACATCGGAG ACAACACCAC AGTGGACTAC       180

ACTTTGTTCG AGTCTTTGTG CTCCAAGAAG GACGTGCGGA ACTTTAAAGC CTGAATTC         238

(2) INFORMATION FOR SEQ ID NO: 13:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 13:

GCACAGCCTT CCTGTGTGG                                                     19

(2) INFORMATION FOR SEQ ID NO: 14:

(i) SEQUENCE CHARACTERISTICS:
            (A) LENGTH: 2160 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 64..1197

(xi) SEQUENCE DESCRIPTION: SEQ ID NO: 14:

AGACAGGGGT AGTGCGAGGC CGGGCACAGC CTTCCTGTGT GGTTTTACCG CCCAGAGAGC        60

GTC ATG GAC CTG GGG AAA CCA ATG AAA AGC GTG CTG GTG GTG GCT CTC        108
    Met Asp Leu Gly Lys Pro Met Lys Ser Val Leu Val Val Ala Leu

-continued

```
         1                   5                   10                  15
CTT GTC ATT TTC CAG GTA TGC CTG TGT CAA GAT GAG GTC ACG GAC GAT      156
Leu Val Ile Phe Gln Val Cys Leu Cys Gln Asp Glu Val Thr Asp Asp
                    20                  25                  30

TAC ATC GGA GAC AAC ACC ACA GTG GAC TAC ACT TTG TTC GAG TCT TTG      204
Tyr Ile Gly Asp Asn Thr Thr Val Asp Tyr Thr Leu Phe Glu Ser Leu
                35                  40                  45

TGC TCC AAG AAG GAC GTG CGG AAC TTT AAA GCC TGG TTC CTC CCT ATC      252
Cys Ser Lys Lys Asp Val Arg Asn Phe Lys Ala Trp Phe Leu Pro Ile
            50                  55                  60

ATG TAC TCC ATC ATT TGT TTC GTG GGC CTA CTG GGC AAT GGG CTG GTC      300
Met Tyr Ser Ile Ile Cys Phe Val Gly Leu Leu Gly Asn Gly Leu Val
        65                  70                  75

GTG TTG ACC TAT ATC TAT TTC AAG AGG CTC AAG ACC ATG ACC GAT ACC      348
Val Leu Thr Tyr Ile Tyr Phe Lys Arg Leu Lys Thr Met Thr Asp Thr
 80              85                  90                  95

TAC CTG CTC AAC CTG GCG GTG GCA GAC ATC CTC TTC CTC CTG ACC CTT      396
Tyr Leu Leu Asn Leu Ala Val Ala Asp Ile Leu Phe Leu Leu Thr Leu
                100                 105                 110

CCC TTC TGG GCC TAC AGC GCG GCC AAG TCC TGG GTC TTC GGT GTC CAC      444
Pro Phe Trp Ala Tyr Ser Ala Ala Lys Ser Trp Val Phe Gly Val His
            115                 120                 125

TTT TGC AAG CTC ATC TTT GCC ATC TAC AAG ATG AGC TTC TTC AGT GGC      492
Phe Cys Lys Leu Ile Phe Ala Ile Tyr Lys Met Ser Phe Phe Ser Gly
        130                 135                 140

ATG CTC CTA CTT CTT TGC ATC AGC ATT GAC CGC TAC GTG GCC ATC GTC      540
Met Leu Leu Leu Cys Ile Ser Ile Asp Arg Tyr Val Ala Ile Val
    145                 150                 155

CAG GCT GTC TCA GCT CAC CGC CAC CGT GCC CGC GTC CTT CTC ATC AGC      588
Gln Ala Val Ser Ala His Arg His Arg Ala Arg Val Leu Leu Ile Ser
160                 165                 170                 175

AAG CTG TCC TGT GTG GGC ATC TGG ATA CTA GCC ACA GTG CTC TCC ATC      636
Lys Leu Ser Cys Val Gly Ile Trp Ile Leu Ala Thr Val Leu Ser Ile
                180                 185                 190

CCA GAG CTC CTG TAC AGT GAC CTC CAG AGG AGC AGC AGT GAG CAA GCG      684
Pro Glu Leu Leu Tyr Ser Asp Leu Gln Arg Ser Ser Ser Glu Gln Ala
            195                 200                 205

ATG CGA TGC TCT CTC ATC ACA GAG CAT GTG GAG GCC TTT ATC ACC ATC      732
Met Arg Cys Ser Leu Ile Thr Glu His Val Glu Ala Phe Ile Thr Ile
        210                 215                 220

CAG GTG GCC CAG ATG GTG ATC GGC TTT CTG GTC CCC TTG CTG GCC ATG      780
Gln Val Ala Gln Met Val Ile Gly Phe Leu Val Pro Leu Leu Ala Met
    225                 230                 235

AGC TTC TGT TAC CTT GTC ATC ATC CGC ACC CTG CTC CAG GCA CGC AAC      828
Ser Phe Cys Tyr Leu Val Ile Ile Arg Thr Leu Leu Gln Ala Arg Asn
240                 245                 250                 255

TTT GAG CGC AAC AAG GCC ATC AAG GTG ATC ATC GCT GTG GTC GTG GTC      876
Phe Glu Arg Asn Lys Ala Ile Lys Val Ile Ile Ala Val Val Val Val
                260                 265                 270

TTC ATA GTC TTC CAG CTG CCC TAC AAT GGG GTG GTC CTG GCC CAG ACG      924
Phe Ile Val Phe Gln Leu Pro Tyr Asn Gly Val Val Leu Ala Gln Thr
            275                 280                 285

GTG GCC AAC TTC AAC ATC ACC AGT AGC ACC TGT GAG CTC AGT AAG CAA      972
Val Ala Asn Phe Asn Ile Thr Ser Ser Thr Cys Glu Leu Ser Lys Gln
        290                 295                 300

CTC AAC ATC GCC TAC GAC GTC ACC TAC AGC CTG GCC TGC GTC CGC TGC     1020
Leu Asn Ile Ala Tyr Asp Val Thr Tyr Ser Leu Ala Cys Val Arg Cys
    305                 310                 315

TGC GTC AAC CCT TTC TTG TAC GCC TTC ATC GGC GTC AAG TTC CGC AAC     1068
```

```
                                            -continued

Cys Val Asn Pro Phe Leu Tyr Ala Phe Ile Gly Val Lys Phe Arg Asn
320                 325                 330                 335

GAT CTC TTC AAG CTC TTC AAG GAC CTG GGC TGC CTC AGC CAG GAG CAG       1116
Asp Leu Phe Lys Leu Phe Lys Asp Leu Gly Cys Leu Ser Gln Glu Gln
                340                 345                 350

CTC CGG CAG TGG TCT TCC TGT CGG CAC ATC CGG CGC TCC TCC ATG AGT       1164
Leu Arg Gln Trp Ser Ser Cys Arg His Ile Arg Arg Ser Ser Met Ser
                355                 360                 365

GTG GAG GCC GAG ACC ACC ACC ACC TTC TCC CCA TAGGCGACTC TTCTGCCTGG     1217
Val Glu Ala Glu Thr Thr Thr Thr Phe Ser Pro
                370                 375

ACTAGAGGGA CCTCTCCCAG GGTCCCTGGG GTGGGGATAG GGAGCAGATG CAATGACTCA     1277

GGACATCCCC CCGCCAAAAG CTGCTCAGGG AAAAGCAGCT CTCCCCTCAG AGTGCAAGCC     1337

CTGCTCCAGA AGTTAGCTTC ACCCCAATCC CAGCTACCTC AACCAATGCC GAAAAAGACA     1397

GGGCTGATAA GCTAACACCA GACAGACAAC ACTGGGAAAC AGAGGCTATT GTCCCCTAAA     1457

CCAAAAACTG AAAGTGAAAG TCCAGAAACT GTTCCCACCT GCTGGAGTGA AGGGGCCAAG     1517

GAGGGTGAGT GCAAGGGGCG TGGGAGTGGC CTGAAGAGTC CTCTGAATGA ACCTTCTGGC     1577

CTCCCACAGA CTCAAATGCT CAGACCAGCT CTTCCGAAAA CCAGGCCTTA TCTCCAAGAC     1637

CAGAGATAGT GGGGAGACTT CTTGGCTTGG TGAGGAAAAG CGGACATCAG CAGCTGGTCA     1697

AACAAACTCT CTGAACCCCT CCCTCCATCG TTTTCTTCAC TGTCCTCCAA GCCAGCGGGA     1757

ATGCAGCTGC CACGCCGCCC TAAAAGCACA CTCATCCCCT CACTTGCCGC GTCGCCCTCC     1817

CAGGCTCTCA ACAGGGGAGA GTGTGGTGTT TCCTGCAGGC CAGGCCAGCT GCCTCCGCGT     1877

GATCAAAGCC ACACTCTGGG CTCCAGAGTG GGGATGACAT GCACTCAGCT CTTGGCTCCA     1937

CTGGGATGGG AGGAGAGGAC AAGGGAAATG TCAGGGGCGG GGAGGGTGAC AGTGGCCGCC     1997

CAAGGCCCAC GAGCTTGTTC TTTGTTCTTT GTCACAGGGA CTGAAAACCT CTCCTCATGT     2057

TCTGCTTTCG ATTCGTTAAG AGAGCAACAT TTTACCCACA CACAGATAAA GTTTTCCCTT     2117

GAGGAAACAA CAGCTTTAAA AGAAAAAAAA AAAAAAGAA TTC                       2160

(2) INFORMATION FOR SEQ ID NO: 15:

(i) SEQUENCE CHARACTERISTICS:
        (A) LENGTH: 378 amino acids
        (B) TYPE: amino acid
        (D) TOPOLOGY: linear (ii) MOLECULE TYPE: protein (xi) SEQUENCE DESCRIPTION: SEQ ID NO: 15:

Met Asp Leu Gly Lys Pro Met Lys Ser Val Leu Val Ala Leu Leu
1               5                   10                  15

Val Ile Phe Gln Val Cys Leu Cys Gln Asp Glu Val Thr Asp Tyr
                20                  25                  30

Ile Gly Asp Asn Thr Thr Val Asp Tyr Thr Leu Phe Glu Ser Leu Cys
                35                  40                  45

Ser Lys Lys Asp Val Arg Asn Phe Lys Ala Trp Phe Leu Pro Ile Met
        50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
                100                 105                 110
```

```
Phe Trp Ala Tyr Ser Ala Ala Lys Ser Trp Val Phe Gly Val His Phe
        115                 120                 125
Cys Lys Leu Ile Phe Ala Ile Tyr Lys Met Ser Phe Phe Ser Gly Met
        130                 135                 140
Leu Leu Leu Leu Cys Ile Ser Ile Asp Arg Tyr Val Ala Ile Val Gln
145                 150                 155                 160
Ala Val Ser Ala His Arg His Arg Ala Arg Val Leu Leu Ile Ser Lys
                    165                 170                 175
Leu Ser Cys Val Gly Ile Trp Ile Leu Ala Thr Val Leu Ser Ile Pro
                180                 185                 190
Glu Leu Leu Tyr Ser Asp Leu Gln Arg Ser Ser Glu Gln Ala Met
                195                 200                 205
Arg Cys Ser Leu Ile Thr Glu His Val Glu Ala Phe Ile Thr Ile Gln
        210                 215                 220
Val Ala Gln Met Val Ile Gly Phe Leu Val Pro Leu Leu Ala Met Ser
225                 230                 235                 240
Phe Cys Tyr Leu Val Ile Ile Arg Thr Leu Leu Gln Ala Arg Asn Phe
                245                 250                 255
Glu Arg Asn Lys Ala Ile Lys Val Ile Ile Ala Val Val Val Val Phe
                260                 265                 270
Ile Val Phe Gln Leu Pro Tyr Asn Gly Val Val Leu Ala Gln Thr Val
        275                 280                 285
Ala Asn Phe Asn Ile Thr Ser Ser Thr Cys Glu Leu Ser Lys Gln Leu
        290                 295                 300
Asn Ile Ala Tyr Asp Val Thr Tyr Ser Leu Ala Cys Val Arg Cys Cys
305                 310                 315                 320
Val Asn Pro Phe Leu Tyr Ala Phe Ile Gly Val Lys Phe Arg Asn Asp
                325                 330                 335
Leu Phe Lys Leu Phe Lys Asp Leu Gly Cys Leu Ser Gln Glu Gln Leu
                340                 345                 350
Arg Gln Trp Ser Ser Cys Arg His Ile Arg Arg Ser Ser Met Ser Val
                355                 360                 365
Glu Ala Glu Thr Thr Thr Thr Phe Ser Pro
        370                 375
```

(2) INFORMATION FOR SEQ ID NO: 16:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: intron
        (B) LOCATION: 253..360

(ix) FEATURE:
        (A) NAME/KEY: CDS
        (B) LOCATION: 243..251

(ix) FEATURE:
        (A) NAME/KEY: TATA_signal
        (B) LOCATION: 151..156

(ix) FEATURE:
        (A) NAME/KEY: 5'UTR
        (B) LOCATION: 180..242

(xi) SEQUENCE DESCRIPTION: SEQ ID NO: 16:

```
GGATCCTATG ACCAGCGACT GTCACCCTCT GTCACCTTTC TTCTGCCCTT TATCTCTGAA      60

GGCATTGAAG GGGCCCTGCA TGAGTCAGGG AGGGCTGGGG GGAGGAGCAA GGGTGGGAGG     120

GGCAGGGAAG AGGGTGGCTT CTCCGACAAC TTAAAAGGGG CTTGAACCAC TTCCTCCCCA     180

GACAGGGGTA GTGCGAGGCC GGGCACAGCC TTCCTGTGTG GTTTTACCGC CCAGAGAGCG     240

TC ATG GAC CTG GGTGAGTGAG CCTCTTCATG TGAGAAGGAA CAGTACCAGG            291
   Met Asp Leu
     1

GTCTTGGACA CCCAGACTGA CCCTGTGGAA TGGGGGTGGA GGATGCGGGT GGAGCGCATA     351

GGGGTGCTT                                                             360
```

(2) INFORMATION FOR SEQ ID NO: 17:

(i) SEQUENCE CHARACTERISTICS:
        (A) LENGTH: 3 amino acids
        (B) TYPE: amino acid
        (D) TOPOLOGY: linear (ii) MOLECULE TYPE: protein (xi) SEQUENCE DESCRIPTION: SEQ ID NO: 17:

```
Met Asp Leu
 1
```

(2) INFORMATION FOR SEQ ID NO: 18:

(i) SEQUENCE CHARACTERISTICS:
        (A) LENGTH: 1900 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: intron
        (B) LOCATION: 1..168

(ix) FEATURE:
        (A) NAME/KEY: exon
        (B) LOCATION: 169..1245

(ix) FEATURE:
        (A) NAME/KEY: CDS
        (B) LOCATION: 169..1242

(ix) FEATURE:
        (A) NAME/KEY: 3'UTR
        (B) LOCATION: 1246..1900

(xi) SEQUENCE DESCRIPTION: SEQ ID NO: 18:

```
CTGCAGGGAG CCATGATTGC ACCACTGCAC TCCAGCCTGG CAACAGAGT GAGACCATGT       60

CTCAAGAAAA AAAAAAAGA AGAAACCAC TGCTCTAGGC TAAATCCCAG CCAGAGTTGG       120

AGCCACCCAG CTAAACTGGC CTGTTTTCCC TCATTTCCTT CCCCGAAG GTA TGC CTG     177
                                                         Val Cys Leu
                                                           1

TGT CAA GAT GAG GTC ACG GAC GAT TAC ATC GGA GAC AAC ACC ACA GTG      225
Cys Gln Asp Glu Val Thr Asp Asp Tyr Ile Gly Asp Asn Thr Thr Val
      5                  10                  15

GAC TAC ACT TTG TTC GAG TCT TTG TGC TCC AAG AAG GAC GTG CGG AAC      273
Asp Tyr Thr Leu Phe Glu Ser Leu Cys Ser Lys Lys Asp Val Arg Asn
 20                  25                  30                  35

TTT AAA GCC TGG TTC CTC CCT ATC ATG TAC TCC ATC ATT TGT TTC GTG      321
```

```
                                                       -continued

Phe Lys Ala Trp Phe Leu Pro Ile Met Tyr Ser Ile Ile Cys Phe Val
             40                  45                  50

GGC CTA CTG GGC AAT GGG CTG GTC GTG TTG ACC TAT ATC TAT TTC AAG         369
Gly Leu Leu Gly Asn Gly Leu Val Val Leu Thr Tyr Ile Tyr Phe Lys
             55                  60                  65

AGG CTC AAG ACC ATG ACC GAT ACC TAC CTG CTC AAC CTG GCG GTG GCA         417
Arg Leu Lys Thr Met Thr Asp Thr Tyr Leu Leu Asn Leu Ala Val Ala
         70                  75                  80

GAC ATC CTC TTC CTC CTG ACC CTT CCC TTC TGG GCC TAC AGC GCG GCC         465
Asp Ile Leu Phe Leu Leu Thr Leu Pro Phe Trp Ala Tyr Ser Ala Ala
     85                  90                  95

AAG TCC TGG GTC TTC GGT GTC CAC TTT TGC AAG CTC ATC TTT GCC ATC         513
Lys Ser Trp Val Phe Gly Val His Phe Cys Lys Leu Ile Phe Ala Ile
100                 105                 110                 115

TAC AAG ATG AGC TTC TTC AGT GGC ATG CTC CTA CTT CTT TGC ATC AGC         561
Tyr Lys Met Ser Phe Phe Ser Gly Met Leu Leu Leu Leu Cys Ile Ser
                120                 125                 130

ATT GAC CGC TAC GTG GCC ATC GTC CAG GCT GTC TCA GCT CAC CGC CAC         609
Ile Asp Arg Tyr Val Ala Ile Val Gln Ala Val Ser Ala His Arg His
            135                 140                 145

CGT GCC CGC GTC CTT CTC ATC AGC AAG CTG TCC TGT GTG GGC ATC TGG         657
Arg Ala Arg Val Leu Leu Ile Ser Lys Leu Ser Cys Val Gly Ile Trp
        150                 155                 160

ATA CTA GCC ACA GTG CTC TCC ATC CCA GAG CTC CTG TAC AGT GAC CTC         705
Ile Leu Ala Thr Val Leu Ser Ile Pro Glu Leu Leu Tyr Ser Asp Leu
    165                 170                 175

CAG AGG AGC AGC AGT GAG CAA GCG ATG CGA TGC TCT CTC ATC ACA GAG         753
Gln Arg Ser Ser Ser Glu Gln Ala Met Arg Cys Ser Leu Ile Thr Glu
180                 185                 190                 195

CAT GTG GAG GCC TTT ATC ACC ATC CAG GTG GCC CAG ATG GTG ATC GGC         801
His Val Glu Ala Phe Ile Thr Ile Gln Val Ala Gln Met Val Ile Gly
                200                 205                 210

TTT CTG GTC CCC CTG CTG GCC ATG AGC TTC TGT TAC CTT GTC ATC ATC         849
Phe Leu Val Pro Leu Leu Ala Met Ser Phe Cys Tyr Leu Val Ile Ile
            215                 220                 225

CGC ACC CTG CTC CAG GCA CGC AAC TTT GAG CGC AAC AAG GCC ATC AAG         897
Arg Thr Leu Leu Gln Ala Arg Asn Phe Glu Arg Asn Lys Ala Ile Lys
        230                 235                 240

GTG ATC ATC GCT GTG GTC GTG GTC TTC ATA GTC TTC CAG CTG CCC TAC         945
Val Ile Ile Ala Val Val Val Val Phe Ile Val Phe Gln Leu Pro Tyr
    245                 250                 255

AAT GGG GTG GTC CTG GCC CAG ACG GTG GCC AAC TTC AAC ATC ACC AGT         993
Asn Gly Val Val Leu Ala Gln Thr Val Ala Asn Phe Asn Ile Thr Ser
260                 265                 270                 275

AGC ACC TGT GAG CTC AGT AAG CAA CTC AAC ATC GCC TAC GAC GTC ACC        1041
Ser Thr Cys Glu Leu Ser Lys Gln Leu Asn Ile Ala Tyr Asp Val Thr
                280                 285                 290

TAC AGC CTG GCC TGC GTC CGC TGC TGC GTC AAC CCT TTC TTG TAC GCC        1089
Tyr Ser Leu Ala Cys Val Arg Cys Cys Val Asn Pro Phe Leu Tyr Ala
            295                 300                 305

TTC ATC GGC GTC AAG TTC CGC AAC GAT CTC TTC AAG CTC TTC AAG GAC        1137
Phe Ile Gly Val Lys Phe Arg Asn Asp Leu Phe Lys Leu Phe Lys Asp
        310                 315                 320

CTG GGC TGC CTC AGC CAG GAG CAG CTC CGG CAG TGG TCT TCC TGT CGG        1185
Leu Gly Cys Leu Ser Gln Glu Gln Leu Arg Gln Trp Ser Ser Cys Arg
    325                 330                 335

CAC ATC CGG CGC TCC TCC ATG AGT GTG GAG GCC GAG ACC ACC ACC ACC        1233
His Ile Arg Arg Ser Ser Met Ser Val Glu Ala Glu Thr Thr Thr Thr
340                 345                 350                 355
```

-continued

```
TTC TCC CCA TAGGCGACTC TTCTGCCTGG ACTAGAGGGA CCTCTCCCAG        1282
Phe Ser Pro

GGTCCCTGGG GTGGGGATAG GGAGCAGATG CAATGACTCA GGACATCCCC CCGCCAAAAG 1342

CTGCTCAGGG AAAAGCAGCT CTCCCCTCAG AGTGCAAGCC CTGCTCCAGA AGTTAGCTTC 1402

ACCCCAATCC CAGCTACCTC AACCAATGCC GAAAAAGACA GGGCTGATAA GCTAACACCA 1462

GACAGACAAC ACTGGGAAAC AGAGGCTATT GTCCCCTAAA CCAAAAACTG AAAGTGAAAG 1522

TCCAGAAACT GTTCCCACCT GCTGGAGTGA AGGGGCCAAG GAGGGTGAGT GCAAGGGGCG 1582

TGGGAGTGGC CTGAAGAGTC CTCTGAATGA ACCTTCTGGC CTCCCACAGA CTCAAATGCT 1642

CAGACCAGCT CTTCCGAAAA CCAGGCCTTA TCTCCAAGAC CAGAGATAGT GGGGAGACTT 1702

CTTGGCTTGG TGAGGAAAAG CGGACATCAG CAGCTGGTCA AACAAACTCT CTGAACCCCT 1762

CCCTCCATCG TTTTCTTCAC TGTCCTCCAA GCCAGCGGGA ATGCAGCTGC CACGCCGCCC 1822

TAAAAGCACA CTCATCCCCT CACTTGCCGC GTCGCCCTCC CAGGCTCTCA ACAGGGGAGA 1882

GTGTGGTGTT TCCTGCAG                                            1900
```

(2) INFORMATION FOR SEQ ID NO: 19:

(i) SEQUENCE CHARACTERISTICS:
        (A) LENGTH: 358 amino acids
        (B) TYPE: amino acid
        (D) TOPOLOGY: linear (ii) MOLECULE TYPE: protein (xi) SEQUENCE DESCRIPTION: SEQ ID NO: 19:

```
Val Cys Leu Cys Gln Asp Glu Val Thr Asp Asp Tyr Ile Gly Asp Asn
 1               5                  10                  15

Thr Thr Val Asp Tyr Thr Leu Phe Glu Ser Leu Cys Ser Lys Lys Asp
                20                  25                  30

Val Arg Asn Phe Lys Ala Trp Phe Leu Pro Ile Met Tyr Ser Ile Ile
            35                  40                  45

Cys Phe Val Gly Leu Leu Gly Asn Gly Leu Val Val Leu Thr Tyr Ile
        50                  55                  60

Tyr Phe Lys Arg Leu Lys Thr Met Thr Asp Thr Tyr Leu Leu Asn Leu
65                  70                  75                  80

Ala Val Ala Asp Ile Leu Phe Leu Leu Thr Leu Pro Phe Trp Ala Tyr
                85                  90                  95

Ser Ala Ala Lys Ser Trp Val Phe Gly Val His Phe Cys Lys Leu Ile
            100                 105                 110

Phe Ala Ile Tyr Lys Met Ser Phe Phe Ser Gly Met Leu Leu Leu Leu
        115                 120                 125

Cys Ile Ser Ile Asp Arg Tyr Val Ala Ile Val Gln Ala Val Ser Ala
    130                 135                 140

His Arg His Arg Ala Arg Val Leu Leu Ile Ser Lys Leu Ser Cys Val
145                 150                 155                 160

Gly Ile Trp Ile Leu Ala Thr Val Leu Ser Ile Pro Glu Leu Leu Tyr
                165                 170                 175

Ser Asp Leu Gln Arg Ser Ser Ser Glu Gln Ala Met Arg Cys Ser Leu
            180                 185                 190

Ile Thr Glu His Val Glu Ala Phe Ile Thr Ile Gln Val Ala Gln Met
        195                 200                 205

Val Ile Gly Phe Leu Val Pro Leu Leu Ala Met Ser Phe Cys Tyr Leu
    210                 215                 220
```

```
Val Ile Ile Arg Thr Leu Leu Gln Ala Arg Asn Phe Glu Arg Asn Lys
225                 230                 235                 240

Ala Ile Lys Val Ile Ile Ala Val Val Val Phe Ile Val Phe Gln
                245                 250                 255

Leu Pro Tyr Asn Gly Val Val Leu Ala Gln Thr Val Ala Asn Phe Asn
                260                 265                 270

Ile Thr Ser Ser Thr Cys Glu Leu Ser Lys Gln Leu Asn Ile Ala Tyr
                275                 280                 285

Asp Val Thr Tyr Ser Leu Ala Cys Val Arg Cys Cys Val Asn Pro Phe
290                 295                 300

Leu Tyr Ala Phe Ile Gly Val Lys Phe Arg Asn Asp Leu Phe Lys Leu
305                 310                 315                 320

Phe Lys Asp Leu Gly Cys Leu Ser Gln Glu Gln Leu Arg Gln Trp Ser
                325                 330                 335

Ser Cys Arg His Ile Arg Arg Ser Ser Met Ser Val Glu Ala Glu Thr
                340                 345                 350

Thr Thr Thr Phe Ser Pro
                355
```

(2) INFORMATION FOR SEQ ID NO: 20:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

```
GGYCAATCT                                                                      9
```

(2) INFORMATION FOR SEQ ID NO: 21:

(i) SEQUENCE CHARACTERISTICS:
        (A) LENGTH: 305 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: intron
        (B) LOCATION: 1..219

(ix) FEATURE:
        (A) NAME/KEY: exon
        (B) LOCATION: 220..270

(ix) FEATURE:
        (A) NAME/KEY: CDS
        (B) LOCATION: 220..270

(ix) FEATURE:
        (A) NAME/KEY: intron
        (B) LOCATION: 271..305

(xi) SEQUENCE DESCRIPTION: SEQ ID NO: 21:

```
ACCTGGGAGT GGAGGAGGAC AAGAAGGAGG TGAGGACAGT GTTGCCGGGC AGCAGGCCAG      60

GTGTTCAAAG GCACAATCTG GTTCTGATGT TCTCTTTCAG CAAACACAGT GCCTGGAGCT     120

TGGGAGGAAA GTTCCCAACA GCGTCTCCCC CTCCACTGCT TTCTTTAATA ACAAAGACTT     180

GTCCTGCCAA GCAATAACTT TCTCGCCTTG TCTCCTACA GGG AAA CCA ATG AAA        234
                                            Gly Lys Pro Met Lys
```

```
AGC GTG CTG GTG GTG GCT CTC CTT GTC ATT TTC CAG GTGAGGTCTC      280
Ser Val Leu Val Val Ala Leu Leu Val Ile Phe Gln
             10                  15

TGCCAAGGAA AGCTCTGTTC CTTCT                                     305
```

(2) INFORMATION FOR SEQ ID NO: 22:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO: 22:

```
Gly Lys Pro Met Lys Ser Val Leu Val Val Ala Leu Leu Val Ile Phe
 1               5                  10                  15
Gln
```

(2) INFORMATION FOR SEQ ID NO: 23:

(i) SEQUENCE CHARACTERISTICS:
        (A) LENGTH: 2751 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: intron
        (B) LOCATION: 1..691

(ix) FEATURE:
        (A) NAME/KEY: exon
        (B) LOCATION: 692..1771

(ix) FEATURE:
        (A) NAME/KEY: CDS
        (B) LOCATION: 692..1768

(ix) FEATURE:
        (A) NAME/KEY: polyA_signal
        (B) LOCATION: 2341..2348

(xi) SEQUENCE DESCRIPTION: SEQ ID NO: 23:

```
CTGCAGGGCC AGACGTTTAC ATCTTAACTA GATCCTCCCT GAGTAATTCA TACATGTGCT      60

AACATCGTTA CTTAGATTTA TTTTTTGTTT TGGTTTGGTT TTTTGGCTTT TTAAGATTTT     120

TTTATTCATT GAACGTAAAT GCATACACTG TAGCTATCTT TAGACACATG AGAAGAAGGT     180

ATCAGACCCA TTACAGATGG TTGTGAGCCA CCGTGGTGTT TGCTGGGAAT TGAACCCAGG     240

ACTTTTGGAA GAGCAGTCCG TATTCTTAAC CTATTAGATA TTATTTATGG GTATAAACAT     300

TTTGCCTGCG TGCATAGAAG TACACCACAT GCACAGAGGA GGTCAGAGTT GGGCATCAGA     360

GCCCATGGAA CTAGAGTTAC AGAGAGCCAC GACGCACCGT GTGGGTGCTG GGAACCGAAC     420

CGGCCTTCTC TACCAGAGCT ACACGCACTC TGCTCTTAAC CCCTGAGCCA GTTCTTCAGC     480

CCCACATGCT GAGGCTTAAG AGGTGTGGAT TTCTAGTCAA AGACTCACTT GGGGTTTGAG     540

GGGGAAACTA TAGTTTCCTG GCTCCTCCG TCTAAGATGC TGACCCAAAG GGTCTAAGGT      600

CTGAGAGTCT GCAAGAGAAC AGAAGCCCCG GGCAATGTCC TGACTGTGAG ATCCGGACTG     660

TGAGCTCATC AGGTGCTTCC TTCCCCCGGA G GTG TGC TTC TGC CAA GAT GAG        712
                                  Val Cys Phe Cys Gln Asp Glu
                                   1               5
```

-continued

| | | |
|---|---|---|
| GTC ACG AGT GAC TAC ATC GGC GAG AAT ACC ACG GTG GAC TAC ACC CTG<br>Val Thr Ser Asp Tyr Ile Gly Glu Asn Thr Thr Val Asp Tyr Thr Leu<br>           10                      15                       20 | 760 |
| TAC GAG TCG GTG TGC TTC AAG AAG GAT GTG CGG AAC TTT AAG GCC TGG<br>Tyr Glu Ser Val Cys Phe Lys Lys Asp Val Arg Asn Phe Lys Ala Trp<br>       25                     30                     35 | 808 |
| TTC CTG CCT CTC ATG TAT TCT GTC ATC TGC TTC GTG GGC CTG CTC GGC<br>Phe Leu Pro Leu Met Tyr Ser Val Ile Cys Phe Val Gly Leu Leu Gly<br>40                       45                     50                 55 | 856 |
| AAC GGG CTG GTG ATA CTG ACG TAC ATC TAT TTC AAG AGG CTC AAG ACC<br>Asn Gly Leu Val Ile Leu Thr Tyr Ile Tyr Phe Lys Arg Leu Lys Thr<br>                   60                     65                     70 | 904 |
| ATG ACG GAT ACC TAC CTG CTC AAC CTG GCC GTG GCA GAC ATC CTT TTC<br>Met Thr Asp Thr Tyr Leu Leu Asn Leu Ala Val Ala Asp Ile Leu Phe<br>          75                     80                     85 | 952 |
| CTC CTA ATT CTT CCC TTC TGG GCC TAC AGC GAA GCC AAG TCC TGG ATC<br>Leu Leu Ile Leu Pro Phe Trp Ala Tyr Ser Glu Ala Lys Ser Trp Ile<br>         90                     95                    100 | 1000 |
| TTT GGC GTC TAC CTG TGT AAG GGC ATC TTT GGC ATC TAT AAG TTA AGC<br>Phe Gly Val Tyr Leu Cys Lys Gly Ile Phe Gly Ile Tyr Lys Leu Ser<br>105                    110                   115 | 1048 |
| TTC TTC AGC GGG ATG CTG CTC CTA TGC ATC AGC ATT GAC CGC TAC<br>Phe Phe Ser Gly Met Leu Leu Leu Cys Ile Ser Ile Asp Arg Tyr<br>120                    125                   130                   135 | 1096 |
| GTA GCC ATC GTC CAG GCC GTG TCG CGT CAT CGC CAC CGC GCC CGC GTG<br>Val Ala Ile Val Gln Ala Val Ser Arg His Arg His Arg Ala Arg Val<br>                  140                   145                   150 | 1144 |
| CTT CTC ATC AGC AAG CTG TCC TGT GTG GGC ATC TGG ATG CTG GCC CTC<br>Leu Leu Ile Ser Lys Leu Ser Cys Val Gly Ile Trp Met Leu Ala Leu<br>                155                    160                   165 | 1192 |
| TTC CTC TCC ATC CCG GAG CTG CTC TAC AGC GGC CTC CAG AAG AAC AGC<br>Phe Leu Ser Ile Pro Glu Leu Leu Tyr Ser Gly Leu Gln Lys Asn Ser<br>          170                     175                   180 | 1240 |
| GGC GAG GAC ACG CTG AGA TGC TCA CTG GTC AGT GCC CAA GTG GAG GCC<br>Gly Glu Asp Thr Leu Arg Cys Ser Leu Val Ser Ala Gln Val Glu Ala<br>185                     190                    195 | 1288 |
| TTG ATC ACC ATC CAA GTG GCC CAG ATG GTT TTT GGG TTC CTA GTG CCT<br>Leu Ile Thr Ile Gln Val Ala Gln Met Val Phe Gly Phe Leu Val Pro<br>200                     205                   210                   215 | 1336 |
| ATG CTG GCT ATG AGT TTC TGC TAC CTC ATT ATC ATC CGT ACC TTG CTC<br>Met Leu Ala Met Ser Phe Cys Tyr Leu Ile Ile Ile Arg Thr Leu Leu<br>                220                    225                   230 | 1384 |
| CAG GCA CGC AAC TTT GAG CGG AAC AAG GCC ATC AAG GTG ATC ATT GCC<br>Gln Ala Arg Asn Phe Glu Arg Asn Lys Ala Ile Lys Val Ile Ile Ala<br>                  235                   240                   245 | 1432 |
| GTG GTG GTA GTC TTC ATA GTC TTC CAG CTG CCC TAC AAT GGG GTG GTC<br>Val Val Val Val Phe Ile Val Phe Gln Leu Pro Tyr Asn Gly Val Val<br>          250                     255                   260 | 1480 |
| CTG GCT CAG ACG GTG GCC AAC TTC AAC ATC ACC AAT AGC AGC TGC TGC<br>Leu Ala Gln Thr Val Ala Asn Phe Asn Ile Thr Asn Ser Ser Cys Cys<br>265                     270                   275 | 1528 |
| GAA ACC AGC AAG CAG CTC AAC ATT GCC TAT GAC GTC ACC TAC AGC CTG<br>Glu Thr Ser Lys Gln Leu Asn Ile Ala Tyr Asp Val Thr Tyr Ser Leu<br>280                     285                   290                   295 | 1576 |
| GCC TCC GTC CGC TGC TGC GTC AAC CCT TTC TTG TAT GCC TTC ATC GGC<br>Ala Ser Val Arg Cys Cys Val Asn Pro Phe Leu Tyr Ala Phe Ile Gly<br>                300                    305                   310 | 1624 |
| GTC AAG TTC CGC AGC GAC CTC TTC AAG CTC TTC AAG GAC TTG GGC TGC<br>Val Lys Phe Arg Ser Asp Leu Phe Lys Leu Phe Lys Asp Leu Gly Cys | 1672 |

|  | | | | | | | | | | | | | |
|---|---|---|---|---|---|---|---|---|---|---|---|---|---|
| | | 315 | | | | 320 | | | | | 325 | | |
| CTC | AGC | CAG | GAA | CGG | CTC | CGG | CAC | TGG | TCT | TCC | TGC | CGG | CAT GTA CGG | 1720
| Leu | Ser | Gln | Glu | Arg | Leu | Arg | His | Trp | Ser | Ser | Cys | Arg | His Val Arg |
| | | 330 | | | | 335 | | | | 340 | | | |

```
CTC AGC CAG GAA CGG CTC CGG CAC TGG TCT TCC TGC CGG CAT GTA CGG      1720
Leu Ser Gln Glu Arg Leu Arg His Trp Ser Ser Cys Arg His Val Arg
        330                 335                 340

AAC GCG TCG GTG AGC ATG GAG GCG GAG ACC ACC ACA ACC TTC TCC CCG      1768
Asn Ala Ser Val Ser Met Glu Ala Glu Thr Thr Thr Thr Phe Ser Pro
    345                 350                 355

TAGGGGGCTC CCCTGCCCGG ACTACAAGGA CCTCTCCCAG GAGCCTTAAT GTGGTGCACA    1828

CATGCACAGA CTCTCCATCC ACCGAATTGC TGCTGAGGGA AGAGCAATTC TGGCCAGTCA    1888

GGTTGACATG AGGACCTAAG AAACTGCTTA ACCCCATCCC ACTTATAACT ACCTCAACCA    1948

AAGCTGTAAA AGATATGGCT GAGAAGTTAA CACTCAAGCC AAGACAGCTA TCCCCAAAAC    2008

GACAGCCAAA AGTGAAAGTG AGAGGCTCCA CACTTTCCGG AGTGAGGGAT GTGGGGCCAG    2068

TGAACACCCT GGTTGAGTAG TCTTCGGAGG CCTCTGAATG AACCTGCTTC TAGCTTAGAG    2128

AGATGTCCCG GAGATTCAAG ACAGAGCTTA TCTCCACACT TAGCAAGCAA GCAAGAGATG    2188

ACAGTCTCTC TAAATGCTCC CACAGAGCAC CCCTGCCCCT CCCTTCTGCC TCTCCACCGC    2248

CTTTCCTGAG GTCCAGGCCA CACCATGACG CTGAGGCAGT CCCAGCTGGG GCTCTGGATG    2308

GCAATGACAA GTAGTTGGGT CTCTATGATG GGAATAAAAA GGTAGGGGAA AGGTGACAGG    2368

AAGGAGAGAA GGTGACCCTG CTGGCTGACA GAGGCCAGCA AGCTACTTCT TTGTTCTCTG    2428

TCAGCCAGCC ACTGATACCT TTCCTCATGT TCTGCTTTTG ATTCATATAT CTTTTATGAA    2488

GAAACAAATA AAAAAAAAAT TTTCCCTCGA GGAAACAACT TGGAAAGAAG GGAGGTAAAT    2548

TCCTTGGTTA AATGGCGAGT GAGTGAGTTG TCCCCCCATT CCACCTGAGA GTCCTGCGCC    2608

CCACACCCCT CCGCCCCAGC CTTCCTTTCT CAGCACTCAG AACCATGAGG TCACAGAGCC    2668

TCTCCGGAGA TGCAAACCCA GGAGGCTGCA AGAGGTGGAA AAAGAGCGAA GACAGGATGT    2728

CTGTCTTGCA CATACACCTG CAG                                            2751
```

(2) INFORMATION FOR SEQ ID NO: 24:

(i) SEQUENCE CHARACTERISTICS:
        (A) LENGTH: 359 amino acids
        (B) TYPE: amino acid
        (D) TOPOLOGY: linear (ii) MOLECULE TYPE: protein (xi) SEQUENCE DESCRIPTION: SEQ ID NO: 24:

```
Val Cys Phe Cys Gln Asp Glu Val Thr Ser Asp Tyr Ile Gly Glu Asn
 1               5                  10                  15

Thr Thr Val Asp Tyr Thr Leu Tyr Glu Ser Val Cys Phe Lys Lys Asp
            20                  25                  30

Val Arg Asn Phe Lys Ala Trp Phe Leu Pro Leu Met Tyr Ser Val Ile
        35                  40                  45

Cys Phe Val Gly Leu Leu Gly Asn Gly Leu Val Ile Leu Thr Tyr Ile
    50                  55                  60

Tyr Phe Lys Arg Leu Lys Thr Met Thr Asp Thr Tyr Leu Leu Asn Leu
65                  70                  75                  80

Ala Val Ala Asp Ile Leu Phe Leu Leu Ile Leu Pro Phe Trp Ala Tyr
                85                  90                  95

Ser Glu Ala Lys Ser Trp Ile Phe Gly Val Tyr Leu Cys Lys Gly Ile
            100                 105                 110

Phe Gly Ile Tyr Lys Leu Ser Phe Phe Ser Gly Met Leu Leu Leu Leu
        115                 120                 125
```

```
Cys Ile Ser Ile Asp Arg Tyr Val Ala Ile Val Gln Ala Val Ser Arg
    130                 135                 140
His Arg His Arg Ala Arg Val Leu Leu Ile Ser Lys Leu Ser Cys Val
145                 150                 155                 160
Gly Ile Trp Met Leu Ala Leu Phe Leu Ser Ile Pro Glu Leu Leu Tyr
                165                 170                 175
Ser Gly Leu Gln Lys Asn Ser Gly Glu Asp Thr Leu Arg Cys Ser Leu
            180                 185                 190
Val Ser Ala Gln Val Glu Ala Leu Ile Thr Ile Gln Val Ala Gln Met
        195                 200                 205
Val Phe Gly Phe Leu Val Pro Met Leu Ala Met Ser Phe Cys Tyr Leu
    210                 215                 220
Ile Ile Ile Arg Thr Leu Leu Gln Ala Arg Asn Phe Glu Arg Asn Lys
225                 230                 235                 240
Ala Ile Lys Val Ile Ile Ala Val Val Val Phe Ile Val Phe Gln
                245                 250                 255
Leu Pro Tyr Asn Gly Val Val Leu Ala Gln Thr Val Ala Asn Phe Asn
                260                 265                 270
Ile Thr Asn Ser Ser Cys Cys Glu Thr Ser Lys Gln Leu Asn Ile Ala
                275                 280                 285
Tyr Asp Val Thr Tyr Ser Leu Ala Ser Val Arg Cys Cys Val Asn Pro
    290                 295                 300
Phe Leu Tyr Ala Phe Ile Gly Val Lys Phe Arg Ser Asp Leu Phe Lys
305                 310                 315                 320
Leu Phe Lys Asp Leu Gly Cys Leu Ser Gln Glu Arg Leu Arg His Trp
                325                 330                 335
Ser Ser Cys Arg His Val Arg Asn Ala Ser Val Ser Met Glu Ala Glu
                340                 345                 350
Thr Thr Thr Thr Phe Ser Pro
            355
```

(2) INFORMATION FOR SEQ ID NO: 25:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

```
TGGACTCACT ATTTGATAAA TGAAAAGGGC CTCCACAATG CCATGTGCAA ATTCACTACC    60
```

(2) INFORMATION FOR SEQ ID NO: 26:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

```
AATGCTGATG ACGGTGATGA AGAATATGCT TCCAAAAAAG CCGATGAAGA AGAAGGCGGT    60
AGTGAA                                                               66
```

-continued (2) INFORMATION FOR SEQ ID NO: 27:

(i) SEQUENCE CHARACTERISTICS:
        (A) LENGTH: 2254 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 593..1657

(xi) SEQUENCE DESCRIPTION: SEQ ID NO: 27:

```
AAGCTTCAAA AAGCCTAGAG CTGGCTGGGC GCTGTGGCTC ACGCCTGTAA TCCTAGCATT      60

TTGGGAGGCT GAGGCGGAAG GATAACTGAG GTCAGGAGTT TGAGACCAGC CTGGCTAACA     120

TGATGAAACC CCATCTCTAC TAAAAATACA AAAATTAGCC AGGCATGGTA GTGCACGCTA     180

TAANCCCAGC TATTTGGGAG GCTGAGGCAG GAGAATCGCT TGAACCCCAG GGACAGAGGT     240

TGCAGTGAGC TGAGATCGCA CCACTGCACT CCAGCCTGGG TGACACAGCG AGACTCCATT     300

TAAAAAAAAA AAAATGCCTA GAGCCAAATG CTCACAGAGC CATTTACTGC ATGGCTTTGG     360

GCAAGTCAAA GGAGTCCGCC TCTCCTGTCA GAAGAGTCTG TTGCAGTCTT CATCACAAGA     420

CTGTTGTGGG GATTAAACAA GATGGCAAGT GGGAAGTTGG GAAATGTAGT GTGCACCCAA     480

CCAATATTTG TTTCTTCCTG CCTGCCTACA TATGAGGCCA CACAGAATTC CAACTTTGTT     540

TCTCTGATAA CTAACACAGT TACTTGTTTT TCTTTCTGAT CCAGGCCTTC ACC ATG        596
                                                           Met
                                                             1
```

```
GAT CAG TTC CCT GAA TCA GTG ACA GAA AAC TTT GAG TAC GAT GAT TTG      644
Asp Gln Phe Pro Glu Ser Val Thr Glu Asn Phe Glu Tyr Asp Asp Leu
        5              10              15

GCT GAG GCC TGT TAT ATT GGG GAC ATC GTG GTC TTT GGG ACT GTG TTC      692
Ala Glu Ala Cys Tyr Ile Gly Asp Ile Val Val Phe Gly Thr Val Phe
         20              25              30

CTG TCC ATA TTC TAC TCC GTC ATC TTT GCC ATT GGC CTG GTG GGA AAT      740
Leu Ser Ile Phe Tyr Ser Val Ile Phe Ala Ile Gly Leu Val Gly Asn
 35              40              45

TTG TTG GTA GTG TTT GCC CTC ACC AAC AGC AAG AAG CCC AAG AGT GTC      788
Leu Leu Val Val Phe Ala Leu Thr Asn Ser Lys Lys Pro Lys Ser Val
 50              55              60              65

ACC GAC ATT TAC CTC CTG AAC CTG GCC TTG TCT GAT CTG CTG TTT GTA      836
Thr Asp Ile Tyr Leu Leu Asn Leu Ala Leu Ser Asp Leu Leu Phe Val
             70              75              80

GCC ACT TTG CCC TTC TGG ACT CAC TAT TTG ATA AAT GAA AAG GGC CTC      884
Ala Thr Leu Pro Phe Trp Thr His Tyr Leu Ile Asn Glu Lys Gly Leu
             85              90              95

CAC AAT GCC ATG TGC AAA TTC ACT ACC GCC TTC TTC TTC ATC GGC TTT      932
His Asn Ala Met Cys Lys Phe Thr Thr Ala Phe Phe Phe Ile Gly Phe
            100             105             110

TTT GGA AGC ATA TTC TTC ATC ACC GTC ATC AGC ATT GAT AGG TAC CTG      980
Phe Gly Ser Ile Phe Phe Ile Thr Val Ile Ser Ile Asp Arg Tyr Leu
        115             120             125

GCC ATC GTC CTG GCC GCC AAC TCC ATG AAC AAC CGG ACC GTG CAG CAT     1028
Ala Ile Val Leu Ala Ala Asn Ser Met Asn Asn Arg Thr Val Gln His
130             135             140             145

GGC GTC ACC ATC AGC CTA GGC GTC TGG GCA GCA GCC ATT TTG GTG GCA     1076
Gly Val Thr Ile Ser Leu Gly Val Trp Ala Ala Ala Ile Leu Val Ala
                150             155             160

GCA CCC CAG TTC ATG TTC ACA AAG CAG AAA GAA AAT GAA TGC CTT GGT     1124
```

```
                                                         -continued

Ala Pro Gln Phe Met Phe Thr Lys Gln Lys Glu Asn Glu Cys Leu Gly
            165                 170                 175

GAC TAC CCC GAG GTC CTC CAG GAA ATC TGG CCC GTG CTC CGC AAT GTG    1172
Asp Tyr Pro Glu Val Leu Gln Glu Ile Trp Pro Val Leu Arg Asn Val
            180                 185                 190

GAA ACA AAT TTT CTT GGC TTC CTA CTC CCC CTG CTC ATT ATG AGT TAT    1220
Glu Thr Asn Phe Leu Gly Phe Leu Leu Pro Leu Leu Ile Met Ser Tyr
            195                 200                 205

TGC TAC TTC AGA ATC ATC CAG ACG CTG TTT TCC TGC AAG AAC CAC AAG    1268
Cys Tyr Phe Arg Ile Ile Gln Thr Leu Phe Ser Cys Lys Asn His Lys
210                 215                 220                 225

AAA GCC AAA GCC ATT AAA CTG ATC CTT CTG GTG GTC ATC GTG TTT TTC    1316
Lys Ala Lys Ala Ile Lys Leu Ile Leu Leu Val Val Ile Val Phe Phe
                    230                 235                 240

CTC TTC TGG ACA CCC TAC AAC GTT ATG ATT TTC CTG GAG ACG CTT AAG    1364
Leu Phe Trp Thr Pro Tyr Asn Val Met Ile Phe Leu Glu Thr Leu Lys
                245                 250                 255

CTC TAT GAC TTC TTT CCC AGT TGT GAC ATG AGG AAG GAT CTG AGG CTG    1412
Leu Tyr Asp Phe Phe Pro Ser Cys Asp Met Arg Lys Asp Leu Arg Leu
            260                 265                 270

GCC CTC AGT GTG ACT GAG ACG GTT GCA TTT AGC CAT TGT TGC CTG AAT    1460
Ala Leu Ser Val Thr Glu Thr Val Ala Phe Ser His Cys Cys Leu Asn
            275                 280                 285

CCT CTC ATC TAT GCA TTT GCT GGG GAG AAG TTC AGA AGA TAC CTT TAC    1508
Pro Leu Ile Tyr Ala Phe Ala Gly Glu Lys Phe Arg Arg Tyr Leu Tyr
290                 295                 300                 305

CAC CTG TAT GGG AAA TGC CTG GCT GTC CTG TGT GGG CGC TCA GTC CAC    1556
His Leu Tyr Gly Lys Cys Leu Ala Val Leu Cys Gly Arg Ser Val His
                    310                 315                 320

GTT GAT TTC TCC TCA TCT GAA TCA CAA AGG AGC AGG CAT GGA AGT GTT    1604
Val Asp Phe Ser Ser Ser Glu Ser Gln Arg Ser Arg His Gly Ser Val
                325                 330                 335

CTG AGC AGC AAT TTT ACT TAC CAC ACG AGT GAT GGA GAT GCA TTG CTC    1652
Leu Ser Ser Asn Phe Thr Tyr His Thr Ser Asp Gly Asp Ala Leu Leu
            340                 345                 350

CTT CTC TGAAGGGAAT CCCAAAGCCT TGTGTCTACA GAGAACCTGG AGTTCCTGAA     1708
Leu Leu
    355

CCTGATGCTG ACTAGTGAGG AAAGATTTTT GTTGTTATTT CTTACAGGCA CAAAATGATG  1768

GACCCAATGC ACACAAAACA ACCCTAGAGT GTTGTTGAGA ATTGTGCTCA AAATTTGAAG  1828

AATGAACAAA TTGAACTCTT TGAATGACAA AGAGTAGACA TTTCTCTTAC TGCAAATGTC  1888

ATCAGAACTT TTTGGTTTGC AGATGACAAA AATTCAATCT AGACTAGTTT AGTTAAATGA  1948

GGGTGGTGAA TATTGTTCAT ATTGTGGCAC AAGCAAAAGG GTGTCTGAGC CCTCAAAGTG  2008

AGGGGAAACC AGGCCTGAGC CAAGCTAGAA TTCCCTCTCT CTGACTCTCA AATCTTTTAG  2068

TCATTATAGA TCCCCCAGAC TTTACATGAC ACAGCTTTAT CACCAGAGAG GGACTGTCTC  2128

CCATGTTTCT CTGCGCCCAA GGGCAAAATT CCCAGGGAAG TGCTCTGATA GGCCAAGTTT  2188

GTATCAGGTG CCCATCCCTG GAAGGTGCTG TTATCCATGG GGAAGGGATA TATAAGATGG  2248

AAGCTT                                                            2254

(2) INFORMATION FOR SEQ ID NO: 28:

(i) SEQUENCE CHARACTERISTICS:
        (A) LENGTH: 355 amino acids
        (B) TYPE: amino acid
        (D) TOPOLOGY: linear
```

-continued (ii) MOLECULE TYPE: protein (xi) SEQUENCE DESCRIPTION: SEQ ID NO: 28:

Met Asp Gln Phe Pro Glu Ser Val Thr Glu Asn Phe Glu Tyr Asp Asp
 1               5                  10                  15

Leu Ala Glu Ala Cys Tyr Ile Gly Asp Ile Val Val Phe Gly Thr Val
             20                  25                  30

Phe Leu Ser Ile Phe Tyr Ser Val Ile Phe Ala Ile Gly Leu Val Gly
         35                  40                  45

Asn Leu Leu Val Val Phe Ala Leu Thr Asn Ser Lys Lys Pro Lys Ser
     50                  55                  60

Val Thr Asp Ile Tyr Leu Leu Asn Leu Ala Leu Ser Asp Leu Leu Phe
 65                  70                  75                  80

Val Ala Thr Leu Pro Phe Trp Thr His Tyr Leu Ile Asn Glu Lys Gly
                 85                  90                  95

Leu His Asn Ala Met Cys Lys Phe Thr Thr Ala Phe Phe Phe Ile Gly
            100                 105                 110

Phe Phe Gly Ser Ile Phe Phe Ile Thr Val Ile Ser Ile Asp Arg Tyr
        115                 120                 125

Leu Ala Ile Val Leu Ala Ala Asn Ser Met Asn Asn Arg Thr Val Gln
    130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
        195                 200                 205

Tyr Cys Tyr Phe Arg Ile Ile Gln Thr Leu Phe Ser Cys Lys Asn His
    210                 215                 220

Lys Lys Ala Lys Ala Ile Lys Leu Ile Leu Leu Val Val Ile Val Phe
225                 230                 235                 240

Phe Leu Phe Trp Thr Pro Tyr Asn Val Met Ile Phe Leu Glu Thr Leu
                245                 250                 255

Lys Leu Tyr Asp Phe Phe Pro Ser Cys Asp Met Arg Lys Asp Leu Arg
            260                 265                 270

Leu Ala Leu Ser Val Thr Glu Thr Val Ala Phe Ser His Cys Cys Leu
        275                 280                 285

Asn Pro Leu Ile Tyr Ala Phe Ala Gly Glu Lys Phe Arg Arg Tyr Leu
    290                 295                 300

Tyr His Leu Tyr Gly Lys Cys Leu Ala Val Leu Cys Gly Arg Ser Val
305                 310                 315                 320

His Val Asp Phe Ser Ser Glu Ser Gln Arg Ser Arg His Gly Ser
                325                 330                 335

Val Leu Ser Ser Asn Phe Thr Tyr His Thr Ser Asp Gly Asp Ala Leu
            340                 345                 350

Leu Leu Leu
        355

(2) INFORMATION FOR SEQ ID NO: 29:

(i) SEQUENCE CHARACTERISTICS:
        (A) LENGTH: 20 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO: 29:

TGGACTCACT ATTTGATAAA                                                    20

(2) INFORMATION FOR SEQ ID NO: 30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 30:

AAGATTTGAG AGTCAGAG                                                      18

(2) INFORMATION FOR SEQ ID NO: 31:

(i) SEQUENCE CHARACTERISTICS:
        (A) LENGTH: 3119 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: exon
        (B) LOCATION: 7..80

(ix) FEATURE:
        (A) NAME/KEY: CDS
        (B) LOCATION: 94..1158

(xi) SEQUENCE DESCRIPTION: SEQ ID NO: 31:

GAATTCACTC GTCTCTGGTA AAGTCTGAGC AGGACAGGGT GGCTGACTGG CAGATCCAGA        60

GGTTCCCTTG GCAGTCCACG CCAGGCCTTC ACC ATG GAT CAG TTC CCT GAA TCA       114
                                    Met Asp Gln Phe Pro Glu Ser
                                      1               5

GTG ACA GAA AAC TTT GAG TAC GAT GAT TTG GCT GAG GCC TGT TAT ATT        162
Val Thr Glu Asn Phe Glu Tyr Asp Asp Leu Ala Glu Ala Cys Tyr Ile
         10                  15                  20

GGG GAC ATC GTG GTC TTT GGG ACT GTG TTC CTG TCC ATA TTC TAC TCC        210
Gly Asp Ile Val Val Phe Gly Thr Val Phe Leu Ser Ile Phe Tyr Ser
     25                  30                  35

GTC ATC TTT GCC ATT GGC CTG GTG GGA AAT TTG TTG GTA GTG TTT GCC        258
Val Ile Phe Ala Ile Gly Leu Val Gly Asn Leu Leu Val Val Phe Ala
 40                  45                  50                  55

CTC ACC AAC AGC AAG AAG CCC AAG AGT GTC ACC GAC ATT TAC CTC CTG        306
Leu Thr Asn Ser Lys Lys Pro Lys Ser Val Thr Asp Ile Tyr Leu Leu
                 60                  65                  70

AAC CTG GCC TTG TCT GAT CTG CTG TTT GTA GCC ACT TTG CCC TTC TGG        354
Asn Leu Ala Leu Ser Asp Leu Leu Phe Val Ala Thr Leu Pro Phe Trp
             75                  80                  85

ACT CAC TAT TTG ATA AAT GAA AAG GGC CTC CAC AAT GCC ATG TGC AAA        402
Thr His Tyr Leu Ile Asn Glu Lys Gly Leu His Asn Ala Met Cys Lys
         90                  95                 100

TTC ACT ACC GCC TTC TTC TTC ATC GGC TTT TTT GGA AGC ATA TTC TTC        450
Phe Thr Thr Ala Phe Phe Phe Ile Gly Phe Phe Gly Ser Ile Phe Phe
    105                 110                 115

```
ATC ACC GTC ATC AGC ATT GAT AGG TAC CTG GCC ATC GTC CTG GCC GCC       498
Ile Thr Val Ile Ser Ile Asp Arg Tyr Leu Ala Ile Val Leu Ala Ala
120                 125                 130                 135

AAC TCC ATG AAC AAC CGG ACC GTG CAG CAT GGC GTC ACC ATC AGC CTA       546
Asn Ser Met Asn Asn Arg Thr Val Gln His Gly Val Thr Ile Ser Leu
                140                 145                 150

GGC GTC TGG GCA GCA GCC ATT TTG GTG GCA GCA CCC CAG TTC ATG TTC       594
Gly Val Trp Ala Ala Ala Ile Leu Val Ala Ala Pro Gln Phe Met Phe
            155                 160                 165

ACA AAG CAG AAA GAA AAT GAA TGC CTT GGT GAC TAC CCC GAG GTC CTC       642
Thr Lys Gln Lys Glu Asn Glu Cys Leu Gly Asp Tyr Pro Glu Val Leu
        170                 175                 180

CAG GAA ATC TGG CCC GTG CTC CGC AAT GTG GAA ACA AAT TTT CTT GGC       690
Gln Glu Ile Trp Pro Val Leu Arg Asn Val Glu Thr Asn Phe Leu Gly
    185                 190                 195

TTC CTA CTC CCC CTG CTC ATT ATG AGT TAT TGC TAC TTC AGA ATC ATC       738
Phe Leu Leu Pro Leu Leu Ile Met Ser Tyr Cys Tyr Phe Arg Ile Ile
200                 205                 210                 215

CAG ACG CTG TTT TCC TGC AAG AAC CAC AAG AAA GCC AAA GCC ATT AAA       786
Gln Thr Leu Phe Ser Cys Lys Asn His Lys Lys Ala Lys Ala Ile Lys
                220                 225                 230

CTG ATC CTT CTG GTG GTC ATC GTG TTT TTC CTC TTC TGG ACA CCC TAC       834
Leu Ile Leu Leu Val Val Ile Val Phe Phe Leu Phe Trp Thr Pro Tyr
            235                 240                 245

AAC GTT ATG ATT TTC CTG GAG ACG CTT AAG CTC TAT GAC TTC TTT CCC       882
Asn Val Met Ile Phe Leu Glu Thr Leu Lys Leu Tyr Asp Phe Phe Pro
        250                 255                 260

AGT TGT GAC ATG AGG AAG GAT CTG AGG CTG GCC CTC AGT GTG ACT GAG       930
Ser Cys Asp Met Arg Lys Asp Leu Arg Leu Ala Leu Ser Val Thr Glu
    265                 270                 275

ACG GTT GCA TTT AGC CAT TGT TGC CTG AAT CCT CTC ATC TAT GCA TTT       978
Thr Val Ala Phe Ser His Cys Cys Leu Asn Pro Leu Ile Tyr Ala Phe
280                 285                 290                 295

GCT GGG GAG AAG TTC AGA AGA TAC CTT TAC CAC CTG TAT GGG AAA TGC      1026
Ala Gly Glu Lys Phe Arg Arg Tyr Leu Tyr His Leu Tyr Gly Lys Cys
                300                 305                 310

CTG GCT GTC CTG TGT GGG CGC TCA GTC CAC GTT GAT TTC TCC TCA TCT      1074
Leu Ala Val Leu Cys Gly Arg Ser Val His Val Asp Phe Ser Ser Ser
            315                 320                 325

GAA TCA CAA AGG AGC AGG CAT GGA AGT GTT CTG AGC AGC AAT TTT ACT      1122
Glu Ser Gln Arg Ser Arg His Gly Ser Val Leu Ser Ser Asn Phe Thr
        330                 335                 340

TAC CAC ACG AGT GAT GGA GAT GCA TTG CTC CTT CTC TGAAGGGAAT          1168
Tyr His Thr Ser Asp Gly Asp Ala Leu Leu Leu Leu
    345                 350                 355

CCCAAAGCCT TGTGTCTACA GAGAACCTGG AGTTCCTGAA CCTGATGCTG ACTAGTGAGG    1228

AAAGATTTTT GTTGTTATTT CTTACAGGCA CAAAATGATG GACCCAATGC ACACAAAACA    1288

ACCCTAGAGT GTTGTTGAGA ATTGTGCTCA AAATTTGAAG AATGAACAAA TTGAACTCTT    1348

TGAATGACAA AGAGTAGACA TTTCTCTTAC TGCAAATGTC ATCAGAACTT TTGGTTTGC     1408

AGATGACAAA AATTCAATCT AGACTAGTTT AGTTAAATGA GGGTGGTGAA TATTGTTCAT    1468

ATTGTGGCAC AAGCAAAAGG GTGTCTGAGC CCTCAAAGTG AGGGGAAACC AGGCCTGAGC    1528

CAAGCTAGAA TTCCCTCTCT CTGACTCTCA AATCTTTTAG TCATTATAGA TCCCCCAGAC    1588

TTTACATGAC ACAGCTTTAT CACCAGAGAG GGACTGACAC CCATGTTTCT CTGGCCCCAA    1648

GGGAAAATTC CCAGGGAAGT GCTCTGATAG GCCAAGTTTG TATCAGGTGC CCATCCCTGG    1708

AAGGTGCTGT TATCCATGGG GAAGGGATAT ATAAGATGGA AGCTTCCAGT CCAATCTCAT    1768
```

```
GGAGAAGCAG AAATACATAT TTCCAAGAAG TTGGATGGGT GGGTACTATT CTGATTACAC   1828

AAAACAAATG CCACACATCA CCCTTACCAT GTGCCTGATC CAGCCTCTCC CCTGATTACA   1888

CCAGCCTCGT CTTCATTAAG CCCTCTTCCA TCATGTCCCC AACCTGCAAG GGCTCCCCAC   1948

TGCCTACTGC ATCGAGTCAA AACTCAAATG CTTGGCTTCT CATACGTCCA CCATGGGGTC   2008

CTACCAATAG ATTCCCCATT GCCTCCTCCT TNCCAAAGGA CTCCACCCAT CCTATCAGCC   2068

TGTCTCTTCC ATATGACCTC ATGCATCTCC ACCTGCTCCC AGGCCAGTAA GGGAAATAGA   2128

AAAACCCTGC CCCCAAATAA GAAGGGATGG ATTCCAACCC AACTCCAGTA GCTTGGGACA   2188

AATCAAGCTT CAGTTTCCTG GTCTGTAGAA GAGGGATAAG GTACCTTTCA CATAGAGATC   2248

ATCCTTTCCA GCATGAGGAA CTAGCCACCA ACTCTTGCAG GTCTCAACCC TTTTGTCTGC   2308

CTCTTAGACT TCTGCTTTCC ACACCTGCAC TGCTGTGCTG TGCCCAAGTT GTGGTGCTGA   2368

CAAAGCTTGG AAGAGCCTGC AGGTGCCTTG GCCGCGTGCA TAGCCCAGAC ACAGAAGAGG   2428

CTGGTTCTTA CGATGGCACC CAGTGAGCAC TCCCAAGTCT ACAGAGTGAT AGCCTTCCGT   2488

AACCCAACTC TCCTGGACTG CCTTGAATAT CCCCTCCCAG TCACCTTGTG CAAGCCCCTG   2548

CCCATCTGGG AAAATACCCC ATCATTCATG CTACTGCCAA CCTGGGGAGC CAGGGCTATG   2608

GGAGCAGCTT TTTTTTCCCC CCTAGAAACG TTTGGAACAA TGTAAAACTT TAAAGCTCGA   2668

AAACAATTGT AATAATGCTA AGAAAAAGT CATCCAATCT AACCACATCA ATATTGTCAT    2728

TCCTGTATTC ACCCGTCCAG ACCTTGTTCA CACTCTCACA TGTTTAGAGT TGCAATCGTA   2788

ATGTACAGAT NNNNTTATAA TCTGATTTGT TTTCCTCTTA ACGTTAGACC ACAAATAGTG   2848

CTCGCTTTCT ATGTAGTTTG GTAATTATCA TTTTAGAAGA CTCTACCAGA CTGTGTATTC   2908

ATTGAAGTCA GATGTGGTAA CTGTTAAATT GCTGTGTATC TGATAGCTCT TTGGCAGTCT   2968

ATATGTTTGT ATAATGAATG AGAGAATAAG TCATGTTCCT TCAAGATCAT GTACCCCAAT   3028

TTACTTGCCA TTACTCAATT GATAAACATT TAACTTGTTT CCAATGTTTT AGCAAATACA   3088

TATTTTATAG AACTTCAAAA AAAAAAAAAA A                                  3119

(2) INFORMATION FOR SEQ ID NO: 32:

(i) SEQUENCE CHARACTERISTICS:
        (A) LENGTH: 355 amino acids
        (B) TYPE: amino acid
        (D) TOPOLOGY: linear (ii) MOLECULE TYPE: protein (xi) SEQUENCE DESCRIPTION: SEQ ID NO: 32:

Met Asp Gln Phe Pro Glu Ser Val Thr Glu Asn Phe Glu Tyr Asp Asp
 1               5                  10                  15

Leu Ala Glu Ala Cys Tyr Ile Gly Asp Ile Val Val Phe Gly Thr Val
                20                  25                  30

Phe Leu Ser Ile Phe Tyr Ser Val Ile Phe Ala Ile Gly Leu Val Gly
            35                  40                  45

Asn Leu Leu Val Val Phe Ala Leu Thr Asn Ser Lys Lys Pro Lys Ser
        50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Phe Ile Gly
            100                 105                 110
```

```
Phe Phe Gly Ser Ile Phe Phe Ile Thr Val Ile Ser Ile Asp Arg Tyr
        115                 120                 125
Leu Ala Ile Val Leu Ala Ala Asn Ser Met Asn Asn Arg Thr Val Gln
130                 135                 140
His Gly Val Thr Ile Ser Leu Gly Val Trp Ala Ala Ile Leu Val
145                 150                 155                 160
Ala Ala Pro Gln Phe Met Phe Thr Lys Gln Lys Glu Asn Glu Cys Leu
                165                 170                 175
Gly Asp Tyr Pro Glu Val Leu Gln Glu Ile Trp Pro Val Leu Arg Asn
                180                 185                 190
Val Glu Thr Asn Phe Leu Gly Phe Leu Leu Pro Leu Leu Ile Met Ser
                195                 200                 205
Tyr Cys Tyr Phe Arg Ile Ile Gln Thr Leu Phe Ser Cys Lys Asn His
        210                 215                 220
Lys Lys Ala Lys Ala Ile Lys Leu Ile Leu Leu Val Val Ile Val Phe
225                 230                 235                 240
Phe Leu Phe Trp Thr Pro Tyr Asn Val Met Ile Phe Leu Glu Thr Leu
                245                 250                 255
Lys Leu Tyr Asp Phe Phe Pro Ser Cys Asp Met Arg Lys Asp Leu Arg
                260                 265                 270
Leu Ala Leu Ser Val Thr Glu Thr Val Ala Phe Ser His Cys Cys Leu
        275                 280                 285
Asn Pro Leu Ile Tyr Ala Phe Ala Gly Glu Lys Phe Arg Arg Tyr Leu
                290                 295                 300
Tyr His Leu Tyr Gly Lys Cys Leu Ala Val Leu Cys Gly Arg Ser Val
305                 310                 315                 320
His Val Asp Phe Ser Ser Ser Glu Ser Gln Arg Ser Arg His Gly Ser
                325                 330                 335
Val Leu Ser Ser Asn Phe Thr Tyr His Thr Ser Asp Gly Asp Ala Leu
                340                 345                 350
Leu Leu Leu
        355

(2) INFORMATION FOR SEQ ID NO: 33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 33:

TGGGTGGATA AGAAGCATC TC                                          22

(2) INFORMATION FOR SEQ ID NO: 34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 34:

AACACTCATG CAAGTGAGCA                                            20
```

(2) INFORMATION FOR SEQ ID NO: 35

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 258..719

(xi) SEQUENCE DESCRIPTION: SEQ ID NO: 35:

```
GAATTCTTTT TGTATTCTAA TACAGTTCAA ATCAGTGTGG CTGGTTCATT TCAACTCCTT      60

CACTACCAAA CTAGGAGGCA GGGACTGGCT TCAGTTTTTC TGCCTTCTCT TTTTCACTGA     120

TGACCAGGGT ATAAAGATAT CTGCTGCATC GAACTTTAAA CTTCACATTG TCCTTATTTT     180

TCTTGATCTT GACAGATTCA GCATCCTTTC ATTGGGCTGT GAACAGAAAG TCCAGATTTG     240

GAATCTGCTC TTTGGTG ATG GAC CCA GAA GAA ACT TCA GTT TAT TTG GAT        290
                   Met Asp Pro Glu Glu Thr Ser Val Tyr Leu Asp
                    1               5                        10

TAT TAC TAT GCT ACG AGC CCA AAC TCT GAC ATC AGG GAG ACC CAC TCC       338
Tyr Tyr Tyr Ala Thr Ser Pro Asn Ser Asp Ile Arg Glu Thr His Ser
             15                  20                  25

CAT GTT CCT TAC ACC TCT GTC TTC CTT CCA GTC TTT TAC ACA GCT GTG       386
His Val Pro Tyr Thr Ser Val Phe Leu Pro Val Phe Tyr Thr Ala Val
         30                  35                  40

TTC CTG ACT GGA GTG CTG GGG AAC CTT GTT CTC ATG GGA GCG TTG CAT       434
Phe Leu Thr Gly Val Leu Gly Asn Leu Val Leu Met Gly Ala Leu His
     45                  50                  55

TTC AAA CCC GGC AGC CGA AGA CTG ATC GAC ATC TTT ATC ATC AAT CTG       482
Phe Lys Pro Gly Ser Arg Arg Leu Ile Asp Ile Phe Ile Ile Asn Leu
 60                  65                  70                  75

GCT GCC TCT GAC TTC ATT TTT CTT GTC ACA TTG CCT CTC TGG GTG GAT       530
Ala Ala Ser Asp Phe Ile Phe Leu Val Thr Leu Pro Leu Trp Val Asp
                 80                  85                  90

AAA GAA GCA TCT CTA GGA CTG TGG CGG ACG GGC TCC TTC CTG TGC AAA       578
Lys Glu Ala Ser Leu Gly Leu Trp Arg Thr Gly Ser Phe Leu Cys Lys
             95                 100                 105

GGG AGC TCC TAC ATG ATC TCC GTC AAT ATG CAC TGC AGT GTC CTC CTG       626
Gly Ser Ser Tyr Met Ile Ser Val Asn Met His Cys Ser Val Leu Leu
        110                 115                 120

CTC ACT TGC ATG AGT GTT GAC CGC TAC CTG GCC ATT GTG TGG CCA GTC       674
Leu Thr Cys Met Ser Val Asp Arg Tyr Leu Ala Ile Val Trp Pro Val
    125                 130                 135

GTA TCC AGG AAA TTC AGA AGG ACA GAC TGT GCA TAT GTA GTC TGT G         720
Val Ser Arg Lys Phe Arg Arg Thr Asp Cys Ala Tyr Val Val Cys
140                 145                 150
```

(2) INFORMATION FOR SEQ ID NO: 36:

(i) SEQUENCE CHARACTERISTICS:
        (A) LENGTH: 154 amino acids
        (B) TYPE: amino acid
        (D) TOPOLOGY: linear (ii) MOLECULE TYPE: protein (xi) SEQUENCE DESCRIPTION: SEQ ID NO: 36:

```
Met Asp Pro Glu Glu Thr Ser Val Tyr Leu Asp Tyr Tyr Tyr Ala Thr
 1               5                  10                  15
```

Ser Pro Asn Ser Asp Ile Arg Glu Thr His Ser His Val Pro Tyr Thr
            20                  25                  30

Ser Val Phe Leu Pro Val Phe Tyr Thr Ala Val Phe Leu Thr Gly Val
        35                  40                  45

Leu Gly Asn Leu Val Leu Met Gly Ala Leu His Phe Lys Pro Gly Ser
    50                  55                  60

Arg Arg Leu Ile Asp Ile Phe Ile Ile Asn Leu Ala Ala Ser Asp Phe
65                  70                  75                  80

Ile Phe Leu Val Thr Leu Pro Leu Trp Val Asp Lys Glu Ala Ser Leu
                85                  90                  95

Gly Leu Trp Arg Thr Gly Ser Phe Leu Cys Lys Gly Ser Ser Tyr Met
            100                 105                 110

Ile Ser Val Asn Met His Cys Ser Val Leu Leu Leu Thr Cys Met Ser
        115                 120                 125

Val Asp Arg Tyr Leu Ala Ile Val Trp Pro Val Val Ser Arg Lys Phe
    130                 135                 140

Arg Arg Thr Asp Cys Ala Tyr Val Val Cys
145                 150

(2) INFORMATION FOR SEQ ID NO: 37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 37:

CTACACGTAC CGGGACTATG A                                              21

(2) INFORMATION FOR SEQ ID NO: 38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 38:

AGAAGACGCT GGCGTACATG                                                2 0

(2) INFORMATION FOR SEQ ID NO: 39:

(i) SEQUENCE CHARACTERISTICS:
        (A) LENGTH: 1872 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 202..1341

(xi) SEQUENCE DESCRIPTION: SEQ ID NO: 39:

CTGCAGGAGA CAGGCTTCCT CCAGGGTCTG GAGAACCCAG AGGCAGCTCC TCCTGAGTGC     60

TGGGAAGGAC TCTGGGCATC TTCAGCCCTT CTTACTCTCT GAGGCTCAAG CCAGAAATTC    120

-continued

```
AGGCTGCTTG CAGAGTGGGT GACAGAGCCA CGGAGCTGGT GTCCCTGGGA CCCTCTGCCC    180

GTCTTCTCTC CACTCCCCAG C ATG GAG GAA GGT GGT GAT TTT GAC AAC TAC      231
                         Met Glu Glu Gly Gly Asp Phe Asp Asn Tyr
                           1               5                  10

TAT GGG GCA GAC AAC CAG TCT GAG TGT GAG TAC ACA GAC TGG AAA TCC      279
Tyr Gly Ala Asp Asn Gln Ser Glu Cys Glu Tyr Thr Asp Trp Lys Ser
             15                  20                  25

TCG GGG GCC CTC ATC CCT GCC ATC TAC ATG TTG GTC TTC CTC CTG GGC      327
Ser Gly Ala Leu Ile Pro Ala Ile Tyr Met Leu Val Phe Leu Leu Gly
         30                  35                  40

ACC ACG GGA AAC GGT CTG GTG CTC TGG ACC GTG TTT CGG AGC AGC CGG      375
Thr Thr Gly Asn Gly Leu Val Leu Trp Thr Val Phe Arg Ser Ser Arg
     45                  50                  55

GAG AAG AGG CGC TCA GCT GAT ATC TTC ATT GCT AGC CTG GCG GTG GCT      423
Glu Lys Arg Arg Ser Ala Asp Ile Phe Ile Ala Ser Leu Ala Val Ala
 60                  65                  70

GAC CTG ACC TTC GTG GTG ACG CTG CCC CTG TGG GCT ACC TAC ACG TAC      471
Asp Leu Thr Phe Val Val Thr Leu Pro Leu Trp Ala Thr Tyr Thr Tyr
 75                  80                  85                  90

CGG GAC TAT GAC TGG CCC TTT GGG ACC TTC TTC TGC AAG CTC AGC AGC      519
Arg Asp Tyr Asp Trp Pro Phe Gly Thr Phe Phe Cys Lys Leu Ser Ser
                 95                 100                 105

TAC CTC ATC TTC GTC AAC ATG TAC GCC AGC GTC TTC TGC CTC ACC GGC      567
Tyr Leu Ile Phe Val Asn Met Tyr Ala Ser Val Phe Cys Leu Thr Gly
             110                 115                 120

CTC AGC TTC GAC CGC TAC CTG GCC ATC GTG AGG CCA GTG GCC AAT GCT      615
Leu Ser Phe Asp Arg Tyr Leu Ala Ile Val Arg Pro Val Ala Asn Ala
         125                 130                 135

CGG CTG AGG CTG CGG GTC AGC GGG GCC GTG GCC ACG GCA GTT CTT TGG      663
Arg Leu Arg Leu Arg Val Ser Gly Ala Val Ala Thr Ala Val Leu Trp
     140                 145                 150

GTG CTG GCC GCC CTC CTG GCC ATG CCT GTC ATG GTG TTA CGC ACC ACC      711
Val Leu Ala Ala Leu Leu Ala Met Pro Val Met Val Leu Arg Thr Thr
155                 160                 165                 170

GGG GAC TTG GAG AAC ACC ACT AAG GTG CAG TGC TAC ATG GAC TAC TCC      759
Gly Asp Leu Glu Asn Thr Thr Lys Val Gln Cys Tyr Met Asp Tyr Ser
                 175                 180                 185

ATG GTG GCC ACT GTG AGC TCA GAG TGG GCC TGG GAG GTG GGC CTT GGG      807
Met Val Ala Thr Val Ser Ser Glu Trp Ala Trp Glu Val Gly Leu Gly
             190                 195                 200

GTC TCG TCC ACC ACC GTG GGC TTT GTG GTG CCC TTC ACC ATC ATG CTG      855
Val Ser Ser Thr Thr Val Gly Phe Val Val Pro Phe Thr Ile Met Leu
         205                 210                 215

ACC TGT TAC TTC TTC ATC GCC CAA ACC ATC GCT GGC CAC TTC CGC AAG      903
Thr Cys Tyr Phe Phe Ile Ala Gln Thr Ile Ala Gly His Phe Arg Lys
     220                 225                 230

GAA CGC ATC GAG GGC CTG CGG AAG CGG CGC CGG CTG CTC AGC ATC ATC      951
Glu Arg Ile Glu Gly Leu Arg Lys Arg Arg Arg Leu Leu Ser Ile Ile
235                 240                 245                 250

GTG GTG CTG GTG GTG ACC TTT GCC CTG TGC TGG ATG CCC TAC CAC CTG      999
Val Val Leu Val Val Thr Phe Ala Leu Cys Trp Met Pro Tyr His Leu
                 255                 260                 265

GTG AAG ACG CTG TAC ATG CTG GGC AGC CTG CTG CAC TGG CCC TGT GAC     1047
Val Lys Thr Leu Tyr Met Leu Gly Ser Leu Leu His Trp Pro Cys Asp
             270                 275                 280

TTT GAC CTC TTC CTC ATG AAC ATC TTC CCC TAC TGC ACC TGC ATC AGC     1095
Phe Asp Leu Phe Leu Met Asn Ile Phe Pro Tyr Cys Thr Cys Ile Ser
         285                 290                 295

TAC GTC AAC AGC TGC CTC AAC CCC TTC CTC TAT GCC TTT TTC GAC CCC     1143
```

```
                                                           -continued

Tyr Val Asn Ser Cys Leu Asn Pro Phe Leu Tyr Ala Phe Phe Asp Pro
        300                 305                 310

CGC TTC CGC CAG GCC TGC ACC TCC ATG CTC TGC TGT GGC CAG AGC AGG        1191
Arg Phe Arg Gln Ala Cys Thr Ser Met Leu Cys Cys Gly Gln Ser Arg
315                 320                 325                 330

TGC GCA GGC ACC TCC CAC AGC AGC AGT GGG GAG AAG TCA GCC AGC TAC        1239
Cys Ala Gly Thr Ser His Ser Ser Ser Gly Glu Lys Ser Ala Ser Tyr
                335                 340                 345

TCT TCG GGG CAC AGC CAG GGG CCC GGC CCC AAC ATG GGC AAG GGT GGA        1287
Ser Ser Gly His Ser Gln Gly Pro Gly Pro Asn Met Gly Lys Gly Gly
        350                 355                 360

GAA CAG ATG CAC GAG AAA TCC ATC CCC TAC AGC CAG GAG ACC CTT GTG        1335
Glu Gln Met His Glu Lys Ser Ile Pro Tyr Ser Gln Glu Thr Leu Val
365                 370                 375

GTT GAC TAGGGCTGGG AGCAGAGAGA AGCCTGGCGC CCTCGGCCCT CCCCGGCCTT        1391
Val Asp
    380

TGCCCTTGCT TTCTGAAAAT CAGGTAGTGT GGCTACTCCC TTGTCCTATG CACATCCTTT        1451

AACTGTCCCC TGATTCTGCC CGCCCTGTCC TCCTCTACTG CTTTATTCTT TCTCAGAGGT        1511

TTGTGGTTTA GGGGAAAGAG ACTGGGCTCT ACAGACCTGA CCCTGCACAA GCCATTTAAT        1571

CTCACTCAGC CTCAGTTTCT CCATTGGTAT GAAATGGGGG AAAGTCATAT TGATCCTAAA        1631

ATGTTGAAGC CTGAGTCTGG ACGCAGTAAA AGCTTGTTTC CCTCTGCTGC TTTCTTAGAT        1691

CTGCAATCGT CTTTCCTCCC CTCTTTCCTT GTAGTTTTTC CCCNCACNAC TCTCTGCACG        1751

TGCCGCTCNT TATCCCNGCT TCTGGCACCA ATCCCCTCCT ACAGCTCGTC CCCCTCNCTC        1811

GATCCATCCT TCTCGCCTGT CTACTTTCTT GTTCTGAAGG GCTACTAAGG GTTAAGGATC        1871

C                                                                       1872

(2) INFORMATION FOR SEQ ID NO: 40:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO: 40:

Met Glu Glu Gly Gly Asp Phe Asp Asn Tyr Tyr Gly Ala Asp Asn Gln
1               5                   10                  15

Ser Glu Cys Glu Tyr Thr Asp Trp Lys Ser Ser Gly Ala Leu Ile Pro
                20                  25                  30

Ala Ile Tyr Met Leu Val Phe Leu Leu Gly Thr Thr Gly Asn Gly Leu
            35                  40                  45

Val Leu Trp Thr Val Phe Arg Ser Ser Arg Glu Lys Arg Arg Ser Ala
        50                  55                  60

Asp Ile Phe Ile Ala Ser Leu Ala Val Ala Asp Leu Thr Phe Val Val
65                  70                  75                  80

Thr Leu Pro Leu Trp Ala Thr Tyr Thr Tyr Arg Asp Tyr Asp Trp Pro
                85                  90                  95

Phe Gly Thr Phe Phe Cys Lys Leu Ser Ser Tyr Leu Ile Phe Val Asn
            100                 105                 110

Met Tyr Ala Ser Val Phe Cys Leu Thr Gly Leu Ser Phe Asp Arg Tyr
        115                 120                 125

Leu Ala Ile Val Arg Pro Val Ala Asn Ala Arg Leu Arg Leu Arg Val
    130                 135                 140
```

-continued

```
Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
            180                 185                 190

Ser Glu Trp Ala Trp Glu Val Gly Leu Gly Val Ser Ser Thr Thr Val
        195                 200                 205

Gly Phe Val Val Pro Phe Thr Ile Met Leu Thr Cys Tyr Phe Phe Ile
    210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
                260                 265                 270

Leu Gly Ser Leu Leu His Trp Pro Cys Asp Phe Asp Leu Phe Leu Met
            275                 280                 285

Asn Ile Phe Pro Tyr Cys Thr Cys Ile Ser Tyr Val Asn Ser Cys Leu
290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
                340                 345                 350

Gly Pro Gly Pro Asn Met Gly Lys Gly Gly Glu Gln Met His Glu Lys
            355                 360                 365

Ser Ile Pro Tyr Ser Gln Glu Thr Leu Val Val Asp
            370                 375                 380
```

(2) INFORMATION FOR SEQ ID NO: 41:

(i) SEQUENCE CHARACTERISTICS:
        (A) LENGTH: 2098 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 551..1681

(xi) SEQUENCE DESCRIPTION: SEQ ID NO: 41:

```
AGTTTCCTGG GAGCGGCCGT GGTTGTGGTG GTGGTGGGAC AGTGTGCAGC CATGAAAGAA      60

GGTGCAAAGG AATCTCCAAA GAAAGCCTGA CCAGCGTAAA AGTTGGGAG GCTTTGTCCT      120

TGTCACTTGT CCACTAAACT CCTCCCCTCC CTGTTATCCT GGTTGACCCT GGGCATCTCT     180

GGGGACAGTA GGCAGGTGAT TGGGAAAGTT AATGGGATTG AGGGGCTGAG GCTGGCAGG     240

GGGCAAAAAG ACTGGCCTTT CAAGGGGTGC AGCATTGGTA GGAACTCTGT TTGGTTCTGG     300

GCTTTAGGGT CTCCTAAGGG AGGAGACTGA AAAGGTCTGG AAATGCTGCT GCTGCTGTGG    360

TCACTGTATA TTTTGCAATT GGGTCTGTGG ACAGGAAGGG GCCGCATGAC CCAGTTAGGA     420

AACTAGTCTT TGTACTCAAC CAGATCCCTT TAAGTTGTCA GTCTGCAGCG ATGGGGGCAG     480
```

```
TATATTTCAG GGGGACCTCT GATGCTGCTG ACCCTGGAGA TAGACTAGAG TTCTCAGCCT    540

AGGTGTGTCC ATG GCG TCA GGA AAC CCT TGG TCC TCT ACT CTC ATG CGT      589
           Met Ala Ser Gly Asn Pro Trp Ser Ser Thr Leu Met Arg
            1               5                  10

GTG TCC GCC CTC ACT CTC CAG GTC CTC CCG ACG GCC ATG AAC ACT ACA     637
Val Ser Ala Leu Thr Leu Gln Val Leu Pro Thr Ala Met Asn Thr Thr
        15              20                  25

TCT TCT GCA GCA CCC CCC TCA CTA GGT GTA GAG TTC ATC TCT CTG CTG     685
Ser Ser Ala Ala Pro Pro Ser Leu Gly Val Glu Phe Ile Ser Leu Leu
 30              35                  40                      45

GCT ATC ATC CTG CTG TCA GTG GCG CTG GCT GTG GGG CTT CCC GGC AAC     733
Ala Ile Ile Leu Leu Ser Val Ala Leu Ala Val Gly Leu Pro Gly Asn
                 50                  55                  60

AGC TTT GTG GTG TGG AGT ATC CTG AAA AGG ATG CAG AAG CGC TCT GTC     781
Ser Phe Val Val Trp Ser Ile Leu Lys Arg Met Gln Lys Arg Ser Val
             65                  70                  75

ACT GCC CTG ATG GTG CTG AAC CTG GCC CTG GCC GAC CTG GCC GTA TTG     829
Thr Ala Leu Met Val Leu Asn Leu Ala Leu Ala Asp Leu Ala Val Leu
         80                  85                  90

CTC ACT GCT CCC TTT TTC CTT CAC TTC CTG GCC CAA GGC ACC TGG AGT     877
Leu Thr Ala Pro Phe Phe Leu His Phe Leu Ala Gln Gly Thr Trp Ser
     95                 100                 105

TTT GGA CTG GCT GGT TGC CGC CTG TGT CAC TAT GTC TGC GGA GTC AGC     925
Phe Gly Leu Ala Gly Cys Arg Leu Cys His Tyr Val Cys Gly Val Ser
110             115                 120                 125

ATG TAC GCC AGC GTC CTG CTT ATC ACG GCC ATG AGT CTA GAC CGC TCA     973
Met Tyr Ala Ser Val Leu Leu Ile Thr Ala Met Ser Leu Asp Arg Ser
                130                 135                 140

CTG GCG GTG GCC CGC CCC TTT GTG TCC CAG AAG CTA CGC ACC AAG GCG    1021
Leu Ala Val Ala Arg Pro Phe Val Ser Gln Lys Leu Arg Thr Lys Ala
            145                 150                 155

ATG GCC CGG CGG GTG CTG GCA GGC ATC TGG GTG TTG TCC TTT CTG CTG    1069
Met Ala Arg Arg Val Leu Ala Gly Ile Trp Val Leu Ser Phe Leu Leu
        160                 165                 170

GCC ACA CCC GTC CTC GCG TAC CGC ACA GTA GTG CCC TGG AAA ACG AAC    1117
Ala Thr Pro Val Leu Ala Tyr Arg Thr Val Val Pro Trp Lys Thr Asn
    175                 180                 185

ATG AGC CTG TGC TTC CCG CGG TAC CCC AGC GAA GGG CAC CGG GCC TTC    1165
Met Ser Leu Cys Phe Pro Arg Tyr Pro Ser Glu Gly His Arg Ala Phe
190             195                 200                 205

CAT CTA ATC TTC GAG GCT GTC ACG GGC TTC CTG CTG CCC TTC CTG GCT    1213
His Leu Ile Phe Glu Ala Val Thr Gly Phe Leu Leu Pro Phe Leu Ala
                210                 215                 220

GTG GTG GCC AGC TAC TCG GAC ATA GGG CGT CGG CTA CAG GCC CGG CGC    1261
Val Val Ala Ser Tyr Ser Asp Ile Gly Arg Arg Leu Gln Ala Arg Arg
            225                 230                 235

TTC CGC CGC AGC CGC CGC ACC GGC CGC CTG GTG GTG CTC ATC ATC CTG    1309
Phe Arg Arg Ser Arg Arg Thr Gly Arg Leu Val Val Leu Ile Ile Leu
        240                 245                 250

ACC TTC GCC GCC TTC TGG CTG CCC TAC CAC GTG GTG AAC CTG GCT GAG    1357
Thr Phe Ala Ala Phe Trp Leu Pro Tyr His Val Val Asn Leu Ala Glu
    255                 260                 265

GCC CGC CGC GCG CTG GCC GGC CAG GCC GCC GGG TTA GGG CTC GTG GGG    1405
Ala Arg Arg Ala Leu Ala Gly Gln Ala Ala Gly Leu Gly Leu Val Gly
270                 275                 280                 285

AAG CGG CTG AGC CTG GCC CGC AAC GTG CTC ATC GCA CTC GCC TTC CTG    1453
Lys Arg Leu Ser Leu Ala Arg Asn Val Leu Ile Ala Leu Ala Phe Leu
                290                 295                 300

AGC AGC AGC GTG AAC CCC GTG CTG TAC GCG TGC GCC GGC GGC GGC CTG    1501
Ser Ser Ser Val Asn Pro Val Leu Tyr Ala Cys Ala Gly Gly Gly Leu
```

```
Ser Ser Ser Val Asn Pro Val Leu Tyr Ala Cys Ala Gly Gly Gly Leu
        305                 310                 315

CTG CGC TCG GCG GGC GTG GGC TTC GTC GCC AAG CTG CTG GAG GGC ACG          1549
Leu Arg Ser Ala Gly Val Gly Phe Val Ala Lys Leu Leu Glu Gly Thr
        320                 325                 330

GGC TCC GAG GCG TCC AGC ACG CGC CGC GGG GGC AGC CTG GGC CAG ACC          1597
Gly Ser Glu Ala Ser Ser Thr Arg Arg Gly Gly Ser Leu Gly Gln Thr
        335                 340                 345

GCT AGG AGC GGC CCC GCC GCT CTG GAG CCC GGC CCT TCC GAG AGC CTC          1645
Ala Arg Ser Gly Pro Ala Ala Leu Glu Pro Gly Pro Ser Glu Ser Leu
350                 355                 360                 365

ACT GCC TCC AGC CCT CTC AAG TTA AAC GAA CTG AAC TAGGCCTGGT               1691
Thr Ala Ser Ser Pro Leu Lys Leu Asn Glu Leu Asn
                370                 375

GGAAGGAGGC GCACTTTCCT CCTGGCAGAA TCGTAGCTCT GAGCCAGTTC AGTACCTGGA        1751

GGAGGAGCAG GGGCGTGGAG GGCGTGGAGG GCGTGGGAGC GTGGGAGGCG GGAGTGGAGT        1811

GGAAGAAGAG GGAGAGATGG AGCAAAGTGA GGGCCGAGTG AGAGCGTGCT CCAGCCTGGC        1871

TCCCACAGGC AGCTTTAACC ATTAAAACTG AAGTCTGAAA TTTGGTCAAC CTTGTGAGTG        1931

GGGTACATGT GCTGTGGGTA TCGGGGTGCT CGTGGGCGCC CTGGTGGGGC CCCTCTCGGT        1991

AGTTGAGAGT CACGTCCTTT AGTTCCCCAT GATTTACAAT TTTGGAAGGG ACACAAAGAA        2051

ACATAGACTG CCCCCATCCC AGATGATTCC GAGTACATAG TCTGCAG                      2098

(2) INFORMATION FOR SEQ ID NO: 42:

(i) SEQUENCE CHARACTERISTICS:
        (A) LENGTH: 377 amino acids
        (B) TYPE: amino acid
        (D) TOPOLOGY: linear (ii) MOLECULE TYPE: protein (xi) SEQUENCE DESCRIPTION: SEQ ID NO: 42:

Met Ala Ser Gly Asn Pro Trp Ser Ser Thr Leu Met Arg Val Ser Ala
1               5                   10                  15

Leu Thr Leu Gln Val Leu Pro Thr Ala Met Asn Thr Ser Ser Ala
            20                  25                  30

Ala Pro Pro Ser Leu Gly Val Glu Phe Ile Ser Leu Leu Ala Ile Ile
        35                  40                  45

Leu Leu Ser Val Ala Leu Ala Val Gly Leu Pro Gly Asn Ser Phe Val
    50                  55                  60

Val Trp Ser Ile Leu Lys Arg Met Gln Lys Arg Ser Val Thr Ala Leu
65                  70                  75                  80

Met Val Leu Asn Leu Ala Leu Ala Asp Leu Ala Val Leu Leu Thr Ala
                85                  90                  95

Pro Phe Phe Leu His Phe Leu Ala Gln Gly Thr Trp Ser Phe Gly Leu
            100                 105                 110

Ala Gly Cys Arg Leu Cys His Tyr Val Cys Gly Val Ser Met Tyr Ala
        115                 120                 125

Ser Val Leu Leu Ile Thr Ala Met Ser Leu Asp Arg Ser Leu Ala Val
    130                 135                 140

Ala Arg Pro Phe Val Ser Gln Lys Leu Arg Thr Lys Ala Met Ala Arg
145                 150                 155                 160

Arg Val Leu Ala Gly Ile Trp Val Leu Ser Phe Leu Leu Ala Thr Pro
                165                 170                 175

Val Leu Ala Tyr Arg Thr Val Val Pro Trp Lys Thr Asn Met Ser Leu
```

-continued

```
                      180                 185                 190
Cys Phe Pro Arg Tyr Pro Ser Glu Gly His Arg Ala Phe His Leu Ile
            195                 200                 205

Phe Glu Ala Val Thr Gly Phe Leu Leu Pro Phe Leu Ala Val Val Ala
    210                 215                 220

Ser Tyr Ser Asp Ile Gly Arg Arg Leu Gln Ala Arg Arg Phe Arg Arg
225                 230                 235                 240

Ser Arg Arg Thr Gly Arg Leu Val Val Leu Ile Ile Leu Thr Phe Ala
                245                 250                 255

Ala Phe Trp Leu Pro Tyr His Val Val Asn Leu Ala Glu Ala Arg Arg
            260                 265                 270

Ala Leu Ala Gly Gln Ala Gly Leu Gly Leu Val Gly Lys Arg Leu
            275                 280                 285

Ser Leu Ala Arg Asn Val Leu Ile Ala Leu Ala Phe Leu Ser Ser Ser
        290                 295                 300

Val Asn Pro Val Leu Tyr Ala Cys Ala Gly Gly Leu Leu Arg Ser
305                 310                 315                 320

Ala Gly Val Gly Phe Val Ala Lys Leu Leu Glu Gly Thr Gly Ser Glu
                325                 330                 335

Ala Ser Ser Thr Arg Arg Gly Gly Ser Leu Gly Gln Thr Ala Arg Ser
            340                 345                 350

Gly Pro Ala Ala Leu Glu Pro Gly Pro Ser Glu Ser Leu Thr Ala Ser
            355                 360                 365

Ser Pro Leu Lys Leu Asn Glu Leu Asn
        370                 375
```

(2) INFORMATION FOR SEQ ID NO: 43:

(i) SEQUENCE CHARACTERISTICS:
        (A) LENGTH: 1901 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 701..1717

(xi) SEQUENCE DESCRIPTION: SEQ ID NO: 43:

```
GGATCCAGAA AGCCCCCAAG AGAGATGCTG AAACTCTCAG GTGGGTAAAA AGAGTAGACC     60

TCTGACGTCC CAGGGTACAG CCCTTGCTGC CATCCTGGGG GCACCCTCCT AAGTGCCAGG    120

GGCAAGCCAT GGTCAGGGGA AGCAGAAAGC GGTGACACCC CGGCCACTGC ACCTGTGGGC    180

AGGTGGGTCA GGGAGGGTCC AGGCACTCAG GATGAACAGA ACTCACCTGC AAGGCTTGG     240

GCTGAGGAGG AGCTGGAATC CTGGAGACAC ACTGCCCCCG CCCCTCACCA CCCCTGTCAC    300

TCAGACAGCA CACCTCAGAG GCAGAACAGA AAACCCAGAG CCTCACCCAG GCAAGGCTCA    360

CGTCCCATTC CCCGCCATGG CACTGACCCG GTCCTCCCAG CTCTGAGGAG CCTCAGATCT    420

CCTGGGTGGC AGGGGTGCAG CTGCATAGCG CCGAAATTCC AAGCCCTGGT TCTGCGTTTG    480

CCTTGTGCTG AAGTTCAGAA TGCCTCTGAC GCTCACGCAC ACCAAATGGA CAAGGAGGTC    540

CCCTCAGCAG CCCCGTGGGC GGTGCTGAGC TTGAAAGTGG GAGGTTCTGA AGGCATTGGA    600

GGCCTGACTT CTGGACTTCA GAGAGCGTGA AGCTGCCTAG ATCGCAAGCT CATTGTGAAC    660

TGTTTGCTTG TTCCCTCCAG GCTCTGACTC CAGCCAAAGC ATG AAT GGC CTT GAA      715
                                               Met Asn Gly Leu Glu
```

```
                            1              5
GTG GCT CCC CCA GGT CTG ATC ACC AAC TTC TCC CTG GCC ACG GCA GAG      763
Val Ala Pro Pro Gly Leu Ile Thr Asn Phe Ser Leu Ala Thr Ala Glu
             10              15             20

CAA TGT GGC CAG GAG ACG CCA CTG GAG AAC ATG CTG TTC GCC TCC TTC      811
Gln Cys Gly Gln Glu Thr Pro Leu Glu Asn Met Leu Phe Ala Ser Phe
         25              30              35

TAC CTT CTG GAT TTT ATC CTG GCT TTA GTT GGC AAT ACC CTG GCT CTG      859
Tyr Leu Leu Asp Phe Ile Leu Ala Leu Val Gly Asn Thr Leu Ala Leu
         40              45              50

TGG CTT TTC ATC CGA GAC CAC AAG TCC GGG ACC CCG GCC AAC GTG TTC      907
Trp Leu Phe Ile Arg Asp His Lys Ser Gly Thr Pro Ala Asn Val Phe
     55              60              65

CTG ATG CAT CTG GCC GTG GCC GAC TTG TCG TGC GTG CTG GTC CTG CCC      955
Leu Met His Leu Ala Val Ala Asp Leu Ser Cys Val Leu Val Leu Pro
 70              75              80              85

ACC CGC CTG GTC TAC CAC TTC TCT GGG AAC CAC TGG CCA TTT GGG GAA     1003
Thr Arg Leu Val Tyr His Phe Ser Gly Asn His Trp Pro Phe Gly Glu
             90              95             100

ATC GCA TGC CGT CTC ACC GGC TTC CTC TTC TAC CTC AAC ATG TAC GCC     1051
Ile Ala Cys Arg Leu Thr Gly Phe Leu Phe Tyr Leu Asn Met Tyr Ala
         105             110             115

AGC ATC TAC TTC CTC ACC TGC ATC AGC GCC GAC CGT TTC CTG GCC ATT     1099
Ser Ile Tyr Phe Leu Thr Cys Ile Ser Ala Asp Arg Phe Leu Ala Ile
         120             125             130

GTG CAC CCG GTC AAG TCC CTC AAG CTC CGC AGG CCC CTC TAC GCA CAC     1147
Val His Pro Val Lys Ser Leu Lys Leu Arg Arg Pro Leu Tyr Ala His
     135             140             145

CTG GCC TGT GCC TTC CTG TGG GTG GTG GTG GCT GTG GCC ATG GCC CCG     1195
Leu Ala Cys Ala Phe Leu Trp Val Val Val Ala Val Ala Met Ala Pro
150             155             160             165

CTG CTG GTG AGC CCA CAG ACC GTG CAG ACC AAC CAC ACG GTG GTC TGC     1243
Leu Leu Val Ser Pro Gln Thr Val Gln Thr Asn His Thr Val Val Cys
             170             175             180

CTG CAG CTG TAC CGG GAG AAG GCC TCC CAC CAT GCC CTG GTG TCC CTG     1291
Leu Gln Leu Tyr Arg Glu Lys Ala Ser His His Ala Leu Val Ser Leu
         185             190             195

GCA GTG GCC TTC ACC TTC CCG TTC ATC ACC ACG GTC ACC TGC TAC CTG     1339
Ala Val Ala Phe Thr Phe Pro Phe Ile Thr Thr Val Thr Cys Tyr Leu
         200             205             210

CTG ATC ATC CGC AGC CTG CGG CAG GGC CTG CGT GTG GAG AAG CGC CTC     1387
Leu Ile Ile Arg Ser Leu Arg Gln Gly Leu Arg Val Glu Lys Arg Leu
     215             220             225

AAG ACC AAG GCA GTG CGC ATG ATC GCC ATA GTG CTG GCC ATC TTC CTG     1435
Lys Thr Lys Ala Val Arg Met Ile Ala Ile Val Leu Ala Ile Phe Leu
230             235             240             245

GTC TGC TTC GTG CCC TAC CAC GTC AAC CGC TCC GTC TAC GTG CTG CAC     1483
Val Cys Phe Val Pro Tyr His Val Asn Arg Ser Val Tyr Val Leu His
             250             255             260

TAC CGC AGC CAT GGG GCC TCC TGC GCC ACC CAG CGC ATC CTG GCC CTG     1531
Tyr Arg Ser His Gly Ala Ser Cys Ala Thr Gln Arg Ile Leu Ala Leu
         265             270             275

GCA AAC CGC ATC ACC TCC TGC CTC ACC AGC CTC AAC GGG GCA CTC GAC     1579
Ala Asn Arg Ile Thr Ser Cys Leu Thr Ser Leu Asn Gly Ala Leu Asp
         280             285             290

CCC ATC ATG TAT TTC TTC GTG GCT GAG AAG TTC CGC CAC GCC CTG TGC     1627
Pro Ile Met Tyr Phe Phe Val Ala Glu Lys Phe Arg His Ala Leu Cys
         295             300             305

AAC TTG CTC TGT GGC AAA AGG CTC AAG GGC CCG CCC CCC AGC TTC GAA     1675
```

```
Asn Leu Leu Cys Gly Lys Arg Leu Lys Gly Pro Pro Ser Phe Glu
310                 315                 320                 325

GGG AAA ACC AAC GAG AGC TCG CTG AGT GCC AAG TCA GAG CTG          1717
Gly Lys Thr Asn Glu Ser Ser Leu Ser Ala Lys Ser Glu Leu
                330                 335

TGAGCGGGGG GCGCCGTCCA GCGCGAGCGC AGACTGTTTA GGACTCAGCA GACCCAGCAA 1777

GAGGCATCTG CCCTTTCCCC AGCCACCTCC CCGGCAAGCA ACCTGAAATC TCAGCAGATG 1837

CCCACCATTT CTCTAGATCG CCTAGTCTCA ACCCATAAAA AGGAAGAACT GACAAAGGGG 1897

ATCC                                                             1901
```

(2) INFORMATION FOR SEQ ID NO: 44:

(i) SEQUENCE CHARACTERISTICS:
        (A) LENGTH: 339 amino acids
        (B) TYPE: amino acid
        (D) TOPOLOGY: linear (ii) MOLECULE TYPE: protein (xi) SEQUENCE DESCRIPTION: SEQ ID NO: 44:

```
Met Asn Gly Leu Glu Val Ala Pro Pro Gly Leu Ile Thr Asn Phe Ser
1               5                   10                  15

Leu Ala Thr Ala Glu Gln Cys Gly Gln Glu Thr Pro Leu Glu Asn Met
                20                  25                  30

Leu Phe Ala Ser Phe Tyr Leu Leu Asp Phe Ile Leu Ala Leu Val Gly
            35                  40                  45

Asn Thr Leu Ala Leu Trp Leu Phe Ile Arg Asp His Lys Ser Gly Thr
        50                  55                  60

Pro Ala Asn Val Phe Leu Met His Leu Ala Val Ala Asp Leu Ser Cys
65                  70                  75                  80

Val Leu Val Leu Pro Thr Arg Leu Val Tyr His Phe Ser Gly Asn His
                85                  90                  95

Trp Pro Phe Gly Glu Ile Ala Cys Arg Leu Thr Gly Phe Leu Phe Tyr
                100                 105                 110

Leu Asn Met Tyr Ala Ser Ile Tyr Phe Leu Thr Cys Ile Ser Ala Asp
            115                 120                 125

Arg Phe Leu Ala Ile Val His Pro Val Lys Ser Leu Lys Leu Arg Arg
        130                 135                 140

Pro Leu Tyr Ala His Leu Ala Cys Ala Phe Leu Trp Val Val Val Ala
145                 150                 155                 160

Val Ala Met Ala Pro Leu Leu Val Ser Pro Gln Thr Val Gln Thr Asn
                165                 170                 175

His Thr Val Val Cys Leu Gln Leu Tyr Arg Glu Lys Ala Ser His His
            180                 185                 190

Ala Leu Val Ser Leu Ala Val Ala Phe Thr Phe Pro Phe Ile Thr Thr
        195                 200                 205

Val Thr Cys Tyr Leu Leu Ile Ile Arg Ser Leu Arg Gln Gly Leu Arg
210                 215                 220

Val Glu Lys Arg Leu Lys Thr Lys Ala Val Arg Met Ile Ala Ile Val
225                 230                 235                 240

Leu Ala Ile Phe Leu Val Cys Phe Val Pro Tyr His Val Asn Arg Ser
                245                 250                 255

Val Tyr Val Leu His Tyr Arg Ser His Gly Ala Ser Cys Ala Thr Gln
            260                 265                 270

Arg Ile Leu Ala Leu Ala Asn Arg Ile Thr Ser Cys Leu Thr Ser Leu
```

```
                275                 280                 285
Asn Gly Ala Leu Asp Pro Ile Met Tyr Phe Phe Val Ala Glu Lys Phe
        290                 295                 300

Arg His Ala Leu Cys Asn Leu Leu Cys Gly Lys Arg Leu Lys Gly Pro
305                 310                 315                 320

Pro Pro Ser Phe Glu Gly Lys Thr Asn Glu Ser Ser Leu Ser Ala Lys
                325                 330                 335

Ser Glu Leu (2) INFORMATION FOR SEQ ID NO: 45:

(i) SEQUENCE CHARACTERISTICS:
        (A) LENGTH: 1317 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 201..1211

(xi) SEQUENCE DESCRIPTION: SEQ ID NO: 45:
```

| | |
|---|---|
| GAGTTGTAGG ATTCTACATT AATTCTCTTG TGCCCTTAGC CCACTACTTC AGAATTTCCT | 60 |
| GAAGAAAGCA AGCCTGAATT GGTTTTTTAA ATTGCTTTAA AAATTTTTTT TAACTGGGTT | 120 |
| AATGCTTGCT GAATTGGAAG TGAATGTCCA TTCCTTTGCC TCTTTTGCAG ATATACACTT | 180 |

```
CAGATAACTA CACCGAGGAA ATG GGC TCA GGG GAC TAT GAC TCC ATG AAG      230
                     Met Gly Ser Gly Asp Tyr Asp Ser Met Lys
                      1               5                  10

GAA CCC TGT TTC CGT GAA GAA AAT GCT AAT TTC AAT AAA ATC TTC CTG    278
Glu Pro Cys Phe Arg Glu Glu Asn Ala Asn Phe Asn Lys Ile Phe Leu
                15                  20                  25

CCC ACC ATC TAC TCC ATC ATC TTC TTA ACT GGC ATT GTG GGC AAT GGA   326
Pro Thr Ile Tyr Ser Ile Ile Phe Leu Thr Gly Ile Val Gly Asn Gly
            30                  35                  40

TTG GTC ATC CTG GTC ATG GGT TAC CAG AAG AAA CTG AGA AGC ATG ACG   374
Leu Val Ile Leu Val Met Gly Tyr Gln Lys Lys Leu Arg Ser Met Thr
        45                  50                  55

GAC AAG TAC AGG CTG CAC CTG TCA GTG GCC GAC CTC CTC TTT GTC ATC   422
Asp Lys Tyr Arg Leu His Leu Ser Val Ala Asp Leu Leu Phe Val Ile
60                  65                  70

ACG CTT CCC TTC TGG GCA GTT GAT GCC GTG GCA AAC TGG TAC TTT GGG   470
Thr Leu Pro Phe Trp Ala Val Asp Ala Val Ala Asn Trp Tyr Phe Gly
75                  80                  85                  90

AAC TTC CTA TGC AAG GCA GTC CAT GTC ATC TAC ACA GTC AAC CTC TAC   518
Asn Phe Leu Cys Lys Ala Val His Val Ile Tyr Thr Val Asn Leu Tyr
            95                  100                 105

AGC AGT GTC CTC ATC CTG GCC TTC ATC AGT CTG GAC CGC TAC CTG GCC   566
Ser Ser Val Leu Ile Leu Ala Phe Ile Ser Leu Asp Arg Tyr Leu Ala
        110                 115                 120

ATC GTC CAC GCC ACC AAC AGT CAG AGG CCA AGG AAG CTG TTG GCT GAA   614
Ile Val His Ala Thr Asn Ser Gln Arg Pro Arg Lys Leu Leu Ala Glu
    125                 130                 135

AAG GTG GTC TAT GTT GGC GTC TGG ATC CCT GCC CTC CTG CTG ACT ATT   662
Lys Val Val Tyr Val Gly Val Trp Ile Pro Ala Leu Leu Leu Thr Ile
    140                 145                 150

CCC GAC TTC ATC TTT GCC AAC GTC AGT GAG GCA GAT GAC AGA TAT ATC   710
Pro Asp Phe Ile Phe Ala Asn Val Ser Glu Ala Asp Asp Arg Tyr Ile
155                 160                 165                 170
```

```
TGT GAC CGC TTC TAC CCC AAT GAC TTG TGG GTG GTT GTG TTC CAG TTT        758
Cys Asp Arg Phe Tyr Pro Asn Asp Leu Trp Val Val Val Phe Gln Phe
            175                 180                 185

CAG CAC ATC ATG GTT GGC CTT ATC CTG CCT GGT ATT GTC ATC CTG TCC        806
Gln His Ile Met Val Gly Leu Ile Leu Pro Gly Ile Val Ile Leu Ser
            190                 195                 200

TGC TAT TGC ATT ATC ATC TCC AAG CTG TCA CAC TCC AAG GGC CAC CAG        854
Cys Tyr Cys Ile Ile Ile Ser Lys Leu Ser His Ser Lys Gly His Gln
            205                 210                 215

AAG CGC AAG GCC CTC AAG ACC ACA GTC ATC CTC ATC CTG GCT TTC TTC        902
Lys Arg Lys Ala Leu Lys Thr Thr Val Ile Leu Ile Leu Ala Phe Phe
            220                 225                 230

GCC TGT TGG CTG CCT TAC TAC ATT GGG ATC AGC ATC GAC TCC TTC ATC        950
Ala Cys Trp Leu Pro Tyr Tyr Ile Gly Ile Ser Ile Asp Ser Phe Ile
235                 240                 245                 250

CTC CTG GAA ATC ATC AAG CAA GGG TGT GAG TTT GAG AAC ACT GTG CAC        998
Leu Leu Glu Ile Ile Lys Gln Gly Cys Glu Phe Glu Asn Thr Val His
            255                 260                 265

AAG TGG ATT TCC ATC ACC GAG GCC CTA GCT TTC TTC CAC TGT TGT CTG       1046
Lys Trp Ile Ser Ile Thr Glu Ala Leu Ala Phe Phe His Cys Cys Leu
            270                 275                 280

AAC CCC ATC CTC TAT GCT TTC CTT GGA GCC AAA TTT AAA ACC TCT GCC       1094
Asn Pro Ile Leu Tyr Ala Phe Leu Gly Ala Lys Phe Lys Thr Ser Ala
            285                 290                 295

CAG CAC GCA CTC ACC TCT GTG AGC AGA GGG TCC AGC CTC AAG ATC CTC       1142
Gln His Ala Leu Thr Ser Val Ser Arg Gly Ser Ser Leu Lys Ile Leu
            300                 305                 310

TCC AAA GGA AAG CGA GGT GGA CAT TCA TCT GTT TCC ACT GAG TCT GAG       1190
Ser Lys Gly Lys Arg Gly Gly His Ser Ser Val Ser Thr Glu Ser Glu
315                 320                 325                 330

TCT TCA AGT TTT CAC TCC AGC TAACACAGAT GTAAAAGACT TTTTTTATAC          1241
Ser Ser Ser Phe His Ser Ser
            335

GATAAATAAC CTTTTTTTAA GTTACACATT TTTCAGATAT AAAAGACTGA CCAATATTGA     1301

AAAAAAAAAA AAAAAA                                                     1317
```

(2) INFORMATION FOR SEQ ID NO: 46:

(i) SEQUENCE CHARACTERISTICS:
        (A) LENGTH: 337 amino acids
        (B) TYPE: amino acid
        (D) TOPOLOGY: linear (ii) MOLECULE TYPE: protein (xi) SEQUENCE DESCRIPTION: SEQ ID NO: 46:

```
Met Gly Ser Gly Asp Tyr Asp Ser Met Lys Glu Pro Cys Phe Arg Glu
 1               5                  10                  15

Glu Asn Ala Asn Phe Asn Lys Ile Phe Leu Pro Thr Ile Tyr Ser Ile
                20                  25                  30

Ile Phe Leu Thr Gly Ile Val Gly Asn Gly Leu Val Ile Leu Val Met
                35                  40                  45

Gly Tyr Gln Lys Lys Leu Arg Ser Met Thr Asp Lys Tyr Arg Leu His
            50                  55                  60

Leu Ser Val Ala Asp Leu Leu Phe Val Ile Thr Leu Pro Phe Trp Ala
65                  70                  75                  80

Val Asp Ala Val Ala Asn Trp Tyr Phe Gly Asn Phe Leu Cys Lys Ala
                85                  90                  95
```

```
Val His Val Ile Tyr Thr Val Asn Leu Tyr Ser Ser Val Leu Ile Leu
        100                 105                 110

Ala Phe Ile Ser Leu Asp Arg Tyr Leu Ala Ile Val His Ala Thr Asn
        115                 120                 125

Ser Gln Arg Pro Arg Lys Leu Leu Ala Glu Lys Val Val Tyr Val Gly
        130                 135                 140

Val Trp Ile Pro Ala Leu Leu Leu Thr Ile Pro Asp Phe Ile Phe Ala
145                 150                 155                 160

Asn Val Ser Glu Ala Asp Asp Arg Tyr Ile Cys Asp Arg Phe Tyr Pro
                165                 170                 175

Asn Asp Leu Trp Val Val Phe Gln Phe Gln His Ile Met Val Gly
                180             185                 190

Leu Ile Leu Pro Gly Ile Val Ile Leu Ser Cys Tyr Cys Ile Ile Ile
                195                 200                 205

Ser Lys Leu Ser His Ser Lys Gly His Gln Lys Arg Lys Ala Leu Lys
        210                 215                 220

Thr Thr Val Ile Leu Ile Leu Ala Phe Phe Ala Cys Trp Leu Pro Tyr
225                 230                 235                 240

Tyr Ile Gly Ile Ser Ile Asp Ser Phe Ile Leu Leu Glu Ile Ile Lys
                245                 250                 255

Gln Gly Cys Glu Phe Glu Asn Thr Val His Lys Trp Ile Ser Ile Thr
                260                 265                 270

Glu Ala Leu Ala Phe Phe His Cys Cys Leu Asn Pro Ile Leu Tyr Ala
            275                 280                 285

Phe Leu Gly Ala Lys Phe Lys Thr Ser Ala Gln His Ala Leu Thr Ser
        290                 295                 300

Val Ser Arg Gly Ser Ser Leu Lys Ile Leu Ser Lys Gly Lys Arg Gly
305                 310                 315                 320

Gly His Ser Ser Val Ser Thr Glu Ser Glu Ser Ser Ser Phe His Ser
                325                 330                 335

Ser (2) INFORMATION FOR SEQ ID NO: 47:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 47:

GTTGGATCCA TGATTGCACC ACTGCA                                    26

(2) INFORMATION FOR SEQ ID NO: 48:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 48:

CGCGCTGTAG GCCCAGGCTT TAAAGTTCC                                 29

(2) INFORMATION FOR SEQ ID NO: 49:
```

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 49:

TTTAAAGCCT GGGCCTACAG CGCGGCCAA                                29

(2) INFORMATION FOR SEQ ID NO: 50:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 50:

GTCACTGTAC AGGAGCTTGC AAAAGTGGA                                29

(2) INFORMATION FOR SEQ ID NO: 51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 51:

TTTTGCAAGC TCCTGTACAG TGACCTCCAG                               30

(2) INFORMATION FOR SEQ ID NO: 52:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 52:

CTGGGCCAGG ACGATAAAGG CCTCCACATG                               30

(2) INFORMATION FOR SEQ ID NO: 53:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 53:

GAGGCCTTTA TCGTCCTGGC CCAGACGGT                                29

(2) INFORMATION FOR SEQ ID NO: 54:

(i) SEQUENCE CHARACTERISTICS:
        (A) LENGTH: 27 base pairs
        (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO: 54:

TCAGAATTCA GGTGACGTCG TAGGCGA                                          27

(2) INFORMATION FOR SEQ ID NO: 55:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 55:

ACTGAATTCT ATGGGGAGAA GGTGG                                            25

(2) INFORMATION FOR SEQ ID NO: 56:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 56:

GGTGAATTCA GGCTTTAAAG TTCCGCAC                                         28

(2) INFORMATION FOR SEQ ID NO: 57:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 57:

CTGGATCCAT GGAGGAAGGT GGT                                              23

(2) INFORMATION FOR SEQ ID NO: 58:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 58:

ATAGTCCCGG TACGTGGCCC CCGAGGATTT                                       30

(2) INFORMATION FOR SEQ ID NO: 59:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 59:

AAATCCTCGG GGGCCACGTA CCGGGACTAT                                30

(2) INFORMATION FOR SEQ ID NO: 60:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 60:

CCCGGTGGTG CGTAAGAGGT AGCTGCTGAG CT                              32

(2) INFORMATION FOR SEQ ID NO: 61:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 61:

CTCAGCAGCT ACCTCTTACG CACCACCGGG GAC                             33

(2) INFORMATION FOR SEQ ID NO: 62:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 62:

GTACAGCGTC TTCACAAGCC CACGGTGGTG G                               31

(2) INFORMATION FOR SEQ ID NO: 63:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 63:

ACCACCGTGG GCTTTGTGAA AGACGCTGTA CAT                             33

(2) INFORMATION FOR SEQ ID NO: 64:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 64:

AGGAATTCTA GAAGAGGTCA AAGTCACA                                   28

(2) INFORMATION FOR SEQ ID NO: 65:

(i) SEQUENCE CHARACTERISTICS:
        (A) LENGTH: 2085 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 177..1310

(xi) SEQUENCE DESCRIPTION: SEQ ID NO: 65:

```
CGGACATGGA CTGCTATCTG CGTCGCCTCA AACAGGAGCT GATGTCCATG AAGGAGGTGG      60

GGGATGGCTT GCAGGATCAG ATGAACTGCA TGATGGGCGC AGACTGGGCT AGCTGGAGAG     120

AGACAAGAAC CAAAAGCACA GCCTTCCTGT GTGATTTCTA CAGCCCCCAG AGCACC         176

ATG GAC CCA GGG AAA CCC AGG AAA AAC GTG CTG GTG GTG GCT CTC CTT      224
Met Asp Pro Gly Lys Pro Arg Lys Asn Val Leu Val Val Ala Leu Leu
  1               5                  10                  15

GTC ATT TTC CAG GTG TGC TTC TGC CAA GAT GAG GTC ACC GAT GAC TAC      272
Val Ile Phe Gln Val Cys Phe Cys Gln Asp Glu Val Thr Asp Asp Tyr
             20                  25                  30

ATC GGC GAG AAT ACC ACG GTG GAC TAC ACC CTG TAC GAG TCG GTG TGC      320
Ile Gly Glu Asn Thr Thr Val Asp Tyr Thr Leu Tyr Glu Ser Val Cys
         35                  40                  45

TTC AAG AAG GAT GTG CGG AAC TTT AAG GCC TGG TTC CTG CCT CTC ATG      368
Phe Lys Lys Asp Val Arg Asn Phe Lys Ala Trp Phe Leu Pro Leu Met
     50                  55                  60

TAT TCT GTC ATC TGC TTC GTG GGC CTG CTC GGC AAC GGG CTG GTG ATA      416
Tyr Ser Val Ile Cys Phe Val Gly Leu Leu Gly Asn Gly Leu Val Ile
 65                  70                  75                  80

CTG ACG TAC ATC TAT TTC AAG AGG CTC AAG ACC ATG ACG GAT ACC TAC      464
Leu Thr Tyr Ile Tyr Phe Lys Arg Leu Lys Thr Met Thr Asp Thr Tyr
                 85                  90                  95

CTG CTC AAC CTG GCC GTG GCA GAC ATC CTT TTC CTC CTA ATT CTT CCC      512
Leu Leu Asn Leu Ala Val Ala Asp Ile Leu Phe Leu Leu Ile Leu Pro
            100                 105                 110

TTC TGG GCC TAC AGC GAA GCC AAG TCC TGG ATC TTT GGC GTC TAC CTG      560
Phe Trp Ala Tyr Ser Glu Ala Lys Ser Trp Ile Phe Gly Val Tyr Leu
        115                 120                 125

TGT AAG GGC ATC TTT GGC ATC TAT AAG TTA AGC TTC TTC AGC GGG ATG      608
Cys Lys Gly Ile Phe Gly Ile Tyr Lys Leu Ser Phe Phe Ser Gly Met
    130                 135                 140

CTG CTG CTC CTA TGC ATC AGC ATT GAC CGC TAC GTA GCC ATC GTC CAG      656
Leu Leu Leu Leu Cys Ile Ser Ile Asp Arg Tyr Val Ala Ile Val Gln
145                 150                 155                 160

GCC GTG TCG CGT CAT CGC CAC CGC GCC CGC GTG CTT CTC ATC AGC AAG      704
Ala Val Ser Arg His Arg His Arg Ala Arg Val Leu Leu Ile Ser Lys
                165                 170                 175

CTG TCC TGT GTG GGC ATC TGG ATG CTG GCC CTC TTC CTC TCC ATC CCG      752
Leu Ser Cys Val Gly Ile Trp Met Leu Ala Leu Phe Leu Ser Ile Pro
            180                 185                 190

GAG CTG CTC TAC AGC GGC CTC CAG AAG AAC AGC GGC GAG GAC ACG CTG      800
Glu Leu Leu Tyr Ser Gly Leu Gln Lys Asn Ser Gly Glu Asp Thr Leu
        195                 200                 205

AGA TGC TCA CTG GTC AGT GCC CAA GTG GAG GCC TTG ATC ACC ATC CAA      848
Arg Cys Ser Leu Val Ser Ala Gln Val Glu Ala Leu Ile Thr Ile Gln
    210                 215                 220
```

```
GTG GCC CAG ATG GTT TTT GGG TTC CTA GTG CCT ATG CTG GCT ATG AGT      896
Val Ala Gln Met Val Phe Gly Phe Leu Val Pro Met Leu Ala Met Ser
225                 230                 235                 240

TTC TGC TAC CTC ATT ATC ATC CGT ACC TTG CTC CAG GCA CGC AAC TTT      944
Phe Cys Tyr Leu Ile Ile Ile Arg Thr Leu Leu Gln Ala Arg Asn Phe
                245                 250                 255

GAG CGG AAC AAG GCC ATC AAG GTG ATC ATT GCC GTG GTG GTA GTC TTC      992
Glu Arg Asn Lys Ala Ile Lys Val Ile Ile Ala Val Val Val Val Phe
            260                 265                 270

ATA GTC TTC CAG CTG CCC TAC AAT GGG GTG GTC CTG GCT CAG ACG GTG     1040
Ile Val Phe Gln Leu Pro Tyr Asn Gly Val Val Leu Ala Gln Thr Val
        275                 280                 285

GCC AAC TTC AAC ATC ACC AAT AGC AGC TGC GAA ACC AGC AAG CAG CTC     1088
Ala Asn Phe Asn Ile Thr Asn Ser Ser Cys Glu Thr Ser Lys Gln Leu
    290                 295                 300

AAC ATT GCC TAT GAC GTC ACC TAC AGC CTG GCC TCC GTC CGC TGC TGC     1136
Asn Ile Ala Tyr Asp Val Thr Tyr Ser Leu Ala Ser Val Arg Cys Cys
305                 310                 315                 320

GTC AAC CCT TTC TTG TAT GCC TTC ATC GGC GTC AAG TTC CGC AGC GAC     1184
Val Asn Pro Phe Leu Tyr Ala Phe Ile Gly Val Lys Phe Arg Ser Asp
                325                 330                 335

CTC TTC AAG CTC TTC AAG GAC TTG GGC TGC CTC AGC CAG GAA CGG CTC     1232
Leu Phe Lys Leu Phe Lys Asp Leu Gly Cys Leu Ser Gln Glu Arg Leu
            340                 345                 350

CGG CAC TGG TCT TCC TGC CGG CAT GTA CGG AAC GCG TCG GTG AGC ATG     1280
Arg His Trp Ser Ser Cys Arg His Val Arg Asn Ala Ser Val Ser Met
        355                 360                 365

GAG GCG GAG ACC ACC ACA ACC TTC TCC CCG TAGGGGCTC CCCTGCCCGG        1330
Glu Ala Glu Thr Thr Thr Thr Phe Ser Pro
    370                 375

ACTACAAGGA CCTCTCCCAG GAGCCTTAAT GTGGTGCACA CATGCACAGA CTCTCCATCC   1390

ACCGAATTGC TGCTGAGGGA AGAGCAATTC TGGCCAGTCA GGTTGACATG AGGACCTAAG   1450

AAACTGCTTA ACCCCATCCC ACTTATAACT ACCTCAACCA AAGCTGTAAA AGATATGGCT   1510

GAGAAGTTAA CACTCAAGCC AAGACAGCTA TCCCCAAAAC GACAGCCAAA AGTGAAAGTG   1570

AGAGGCTCCA CACTTTCCGG AGTGAGGGAT GTGGGGCCAG TGAACACCCT GGTTGAGTAG   1630

TCTTCGGAGG CCTCTGAATG AACCTGCTTC TAGCTTAGAG AGATGTCCCG GAGATTCAAG   1690

ACAGAGCTTA TCTCCACACT TAGCAAGCAA GCAAGAGATG ACAGTCTCTC TAAATGCTCC   1750

CACAGAGCAC CCCTGCCCCT CCCTTCTGCC TCTCCACCGC CTTTCCTGAG GTCCAGGCCA   1810

CACCATGACG CTGAGGCAGT CCCAGCTGGG GCTCTGGATG GCAATGACAA GTAGTTGGGT   1870

CTCTATGATG GGAATAAAAA GGTAGGGGAA AGGTGACAGG AAGGAGAGAA GGTGACCCTG   1930

CTGGCTGACA GAGGCCAGCA AGCTACTTCT TTGTTCTCTG TCAGCCAGCC ACTGATACCT   1990

TTCCTCATGT TCTGCTTTTG ATTCATATAT CTTTTATGAA GAAACAAATA AAAAAAAAT    2050

TTTCCCTCGA GGAAACAACT TGGAAAAAAA AAAA                               2085
```

(2) INFORMATION FOR SEQ ID NO: 66:

(i) SEQUENCE CHARACTERISTICS:
        (A) LENGTH: 378 amino acids
        (B) TYPE: amino acid
        (D) TOPOLOGY: linear (ii) MOLECULE TYPE: protein (xi) SEQUENCE DESCRIPTION: SEQ ID NO: 66:

-continued

```
Met Asp Pro Gly Lys Pro Arg Lys Asn Val Leu Val Val Ala Leu Leu
 1               5                  10                  15

Val Ile Phe Gln Val Cys Phe Cys Gln Asp Glu Val Thr Asp Asp Tyr
                 20                  25                  30

Ile Gly Glu Asn Thr Thr Val Asp Tyr Thr Leu Tyr Glu Ser Val Cys
             35                  40                  45

Phe Lys Lys Asp Val Arg Asn Phe Lys Ala Trp Phe Leu Pro Leu Met
         50                  55                  60

Tyr Ser Val Ile Cys Phe Val Gly Leu Leu Gly Asn Gly Leu Val Ile
 65                  70                  75                  80

Leu Thr Tyr Ile Tyr Phe Lys Arg Leu Lys Thr Met Thr Asp Thr Tyr
                     85                  90                  95

Leu Leu Asn Leu Ala Val Ala Asp Ile Leu Phe Leu Leu Ile Leu Pro
             100                 105                 110

Phe Trp Ala Tyr Ser Glu Ala Lys Ser Trp Ile Phe Gly Val Tyr Leu
         115                 120                 125

Cys Lys Gly Ile Phe Gly Ile Tyr Lys Leu Ser Phe Phe Ser Gly Met
         130                 135                 140

Leu Leu Leu Leu Cys Ile Ser Ile Asp Arg Tyr Val Ala Ile Val Gln
145                 150                 155                 160

Ala Val Ser Arg His Arg His Arg Ala Arg Val Leu Leu Ile Ser Lys
                 165                 170                 175

Leu Ser Cys Val Gly Ile Trp Met Leu Ala Leu Phe Leu Ser Ile Pro
             180                 185                 190

Glu Leu Leu Tyr Ser Gly Leu Gln Lys Asn Ser Gly Glu Asp Thr Leu
             195                 200                 205

Arg Cys Ser Leu Val Ser Ala Gln Val Glu Ala Leu Ile Thr Ile Gln
    210                 215                 220

Val Ala Gln Met Val Phe Gly Phe Leu Val Pro Met Leu Ala Met Ser
225                 230                 235                 240

Phe Cys Tyr Leu Ile Ile Ile Arg Thr Leu Leu Gln Ala Arg Asn Phe
             245                 250                 255

Glu Arg Asn Lys Ala Ile Lys Val Ile Ile Ala Val Val Val Val Phe
             260                 265                 270

Ile Val Phe Gln Leu Pro Tyr Asn Gly Val Val Leu Ala Gln Thr Val
             275                 280                 285

Ala Asn Phe Asn Ile Thr Asn Ser Ser Cys Glu Thr Ser Lys Gln Leu
    290                 295                 300

Asn Ile Ala Tyr Asp Val Thr Tyr Ser Leu Ala Ser Val Arg Cys Cys
305                 310                 315                 320

Val Asn Pro Phe Leu Tyr Ala Phe Ile Gly Val Lys Phe Arg Ser Asp
                 325                 330                 335

Leu Phe Lys Leu Phe Lys Asp Leu Gly Cys Leu Ser Gln Glu Arg Leu
             340                 345                 350

Arg His Trp Ser Ser Cys Arg His Val Arg Asn Ala Ser Val Ser Met
             355                 360                 365

Glu Ala Glu Thr Thr Thr Thr Phe Ser Pro
    370                 375
```